(12) United States Patent
McGarraugh et al.

(10) Patent No.: US 7,920,907 B2
(45) Date of Patent: Apr. 5, 2011

(54) ANALYTE MONITORING SYSTEM AND METHOD

(75) Inventors: Geoffrey V. McGarraugh, Oakland, CA (US); Benjamin J. Feldman, Oakland, CA (US); Thomas A. Peyser, Menlo Park, CA (US); John C. Mazza, Pleasanton, CA (US); Timothy T. Goodnow, Pleasanton, CA (US); Kerstin Rebrin, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/759,927

(22) Filed: Jun. 7, 2007

(65) Prior Publication Data

US 2008/0058625 A1 Mar. 6, 2008

Related U.S. Application Data

(60) Provisional application No. 60/804,170, filed on Jun. 7, 2006, provisional application No. 60/804,169, filed on Jun. 7, 2006.

(51) Int. Cl.
*A61B 5/00* (2006.01)
(52) U.S. Cl. ........................ 600/347; 600/365
(58) Field of Classification Search ................ None
See application file for complete search history.

(56) References Cited

U.S. PATENT DOCUMENTS

| | | | |
|---|---|---|---|
| 2,402,306 A | 6/1946 | Turkel | |
| 3,132,123 A | 5/1964 | Harris, Jr. et al. | |
| 3,210,578 A | 10/1965 | Sherer | |
| 3,219,533 A | 11/1965 | Mullins | |
| 3,260,656 A | 7/1966 | Ross, Jr. | |
| 3,282,875 A | 11/1966 | Connolly et al. | |
| 3,304,413 A | 2/1967 | Lehmann et al. | |
| 3,310,606 A | 3/1967 | Fritz | |
| 3,381,371 A | 5/1968 | Russell | |
| 3,397,191 A | 8/1968 | Beckerbauer | |
| 3,581,062 A | 5/1971 | Aston | |
| 3,635,926 A | 1/1972 | Gresham et al. | |
| 3,651,318 A | 3/1972 | Czekajewski | |
| 3,653,841 A | 4/1972 | Klein | |
| 3,698,386 A | 10/1972 | Fried | |
| 3,719,564 A | 3/1973 | Lilly, Jr. et al. | |
| 3,768,014 A | 10/1973 | Smith et al. | |
| 3,775,182 A | 11/1973 | Patton et al. | |
| 3,776,832 A | 12/1973 | Oswin et al. | |

(Continued)

FOREIGN PATENT DOCUMENTS

DE 4401400 7/1995

(Continued)

OTHER PUBLICATIONS

Guerci et al "Clinical Performance of CGMS Patients in Type I Diabetes Patients Treated by Continuous Subcutaneous Insulin Infusion Using Insulin Analogs," Diabetes Care, vol. 26, pp. 582-589, 2003.*

(Continued)

*Primary Examiner* — Charles A Marmor, II
*Assistant Examiner* — Michael D'Angelo
(74) *Attorney, Agent, or Firm* — Jackson & Co., LLP

(57) ABSTRACT

Devices and methods for monitoring an analyte are provided. Embodiments include continuous analyte sensors having a high degree of accuracy.

23 Claims, 9 Drawing Sheets

U.S. PATENT DOCUMENTS

| | | |
|---|---|---|
| 3,785,939 A | 1/1974 | Hsu |
| 3,826,244 A | 7/1974 | Salcman et al. |
| 3,837,339 A | 9/1974 | Aisenberg et al. |
| 3,851,018 A | 11/1974 | Kelly |
| 3,898,984 A | 8/1975 | Mandel et al. |
| 3,919,051 A | 11/1975 | Koch et al. |
| 3,926,760 A | 12/1975 | Allen et al. |
| 3,929,971 A | 12/1975 | Roy |
| 3,930,889 A | 1/1976 | Ruggiero et al. |
| 3,933,593 A | 1/1976 | Sternberg |
| 3,943,918 A | 3/1976 | Lewis |
| 3,949,388 A | 4/1976 | Fuller |
| 3,957,613 A | 5/1976 | Macur |
| 3,964,974 A | 6/1976 | Banauch et al. |
| 3,966,580 A | 6/1976 | Janata et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,032,729 A | 6/1977 | Koistinen |
| 4,036,749 A | 7/1977 | Anderson |
| 4,040,908 A | 8/1977 | Clark, Jr. |
| 4,052,754 A | 10/1977 | Homsy |
| 4,055,175 A | 10/1977 | Clemens et al. |
| 4,059,406 A | 11/1977 | Fleet |
| 4,059,708 A | 11/1977 | Heiss, Jr. et al. |
| 4,073,713 A | 2/1978 | Newman |
| 4,076,596 A | 2/1978 | Connery et al. |
| 4,076,656 A | 2/1978 | White et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,146,029 A | 3/1979 | Ellinwood, Jr. |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,193,982 A | 3/1980 | Avrameas et al. |
| 4,197,840 A | 4/1980 | Beck et al. |
| 4,206,755 A | 6/1980 | Klein |
| 4,215,703 A | 8/1980 | Willson |
| 4,224,125 A | 9/1980 | Nakamura et al. |
| 4,240,438 A | 12/1980 | Updike et al. |
| 4,240,889 A | 12/1980 | Yoda et al. |
| 4,241,438 A | 12/1980 | Kern |
| 4,245,634 A | 1/1981 | Albisser et al. |
| 4,247,297 A | 1/1981 | Berti et al. |
| 4,253,469 A | 3/1981 | Aslan |
| 4,255,500 A | 3/1981 | Hooke |
| 4,259,540 A | 3/1981 | Sabia |
| 4,271,449 A | 6/1981 | Grogan |
| 4,275,225 A | 6/1981 | Krespan |
| 4,282,872 A | 8/1981 | Franetzki et al. |
| 4,294,258 A | 10/1981 | Bernard |
| 4,318,784 A | 3/1982 | Higgins et al. |
| 4,324,257 A | 4/1982 | Albarda et al. |
| 4,327,725 A | 5/1982 | Cortese et al. |
| 4,331,869 A | 5/1982 | Rollo |
| 4,335,255 A | 6/1982 | Krespan |
| 4,340,458 A | 7/1982 | Lerner et al. |
| 4,344,438 A | 8/1982 | Schultz |
| 4,345,603 A | 8/1982 | Schulman |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,357,282 A | 11/1982 | Anderson et al. |
| 4,360,019 A | 11/1982 | Portner et al. |
| 4,365,637 A | 12/1982 | Johnson |
| 4,366,033 A | 12/1982 | Richter et al. |
| 4,374,013 A | 2/1983 | Enfors |
| 4,375,399 A | 3/1983 | Havas et al. |
| 4,384,586 A | 5/1983 | Christiansen |
| 4,388,166 A | 6/1983 | Suzuki et al. |
| 4,390,621 A | 6/1983 | Bauer |
| 4,392,933 A | 7/1983 | Nakamura et al. |
| 4,401,122 A | 8/1983 | Clark, Jr. |
| 4,403,984 A | 9/1983 | Ash et al. |
| 4,404,066 A | 9/1983 | Johnson |
| 4,407,288 A | 10/1983 | Langer et al. |
| 4,407,959 A | 10/1983 | Tsuji et al. |
| 4,415,666 A | 11/1983 | D'Orazio et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,431,507 A | 2/1984 | Nankai et al. |
| 4,436,094 A | 3/1984 | Cerami |
| 4,440,175 A | 4/1984 | Wilkins |
| 4,442,841 A | 4/1984 | Uehara et al. |
| 4,443,218 A | 4/1984 | DeCant, Jr. et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,476,003 A | 10/1984 | Frank et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,499,249 A | 2/1985 | Nakagawa et al. |
| 4,506,680 A | 3/1985 | Stokes |
| 4,509,531 A | 4/1985 | Ward |
| 4,512,348 A | 4/1985 | Uchigaki et al. |
| RE31,916 E | 6/1985 | Oswin et al. |
| 4,522,690 A | 6/1985 | Venkatsetty |
| 4,524,114 A | 6/1985 | Samuels et al. |
| 4,526,661 A | 7/1985 | Steckhan et al. |
| 4,526,948 A | 7/1985 | Resnick |
| 4,527,240 A | 7/1985 | Kvitash |
| 4,530,696 A | 7/1985 | Bisera et al. |
| 4,534,356 A | 8/1985 | Papadakis |
| 4,534,825 A | 8/1985 | Koning et al. |
| 4,538,616 A | 9/1985 | Rogoff |
| 4,543,955 A | 10/1985 | Schroeppel |
| 4,544,869 A | 10/1985 | Pittaway |
| 4,545,382 A | 10/1985 | Higgins et al. |
| 4,552,840 A | 11/1985 | Riffer |
| 4,554,927 A | 11/1985 | Fussell |
| 4,560,534 A | 12/1985 | Kung et al. |
| 4,561,443 A | 12/1985 | Hogrefe et al. |
| 4,569,589 A | 2/1986 | Neufeld |
| 4,571,292 A | 2/1986 | Liu et al. |
| 4,573,994 A | 3/1986 | Fischell et al. |
| 4,577,642 A | 3/1986 | Stokes |
| 4,581,336 A | 4/1986 | Malloy et al. |
| 4,595,011 A | 6/1986 | Phillips |
| 4,595,479 A | 6/1986 | Kimura et al. |
| 4,614,760 A | 9/1986 | Homan et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| RE32,361 E | 2/1987 | Duggan |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,663,824 A | 5/1987 | Kenmochi |
| 4,671,288 A | 6/1987 | Gough |
| 4,674,652 A | 6/1987 | Aten et al. |
| 4,679,562 A | 7/1987 | Luksha |

| | | |
|---|---|---|
| 4,680,268 A | 7/1987 | Clark, Jr. |
| 4,681,111 A | 7/1987 | Silvian |
| 4,682,602 A | 7/1987 | Prohaska |
| 4,684,537 A | 8/1987 | Graetzel et al. |
| 4,685,463 A | 8/1987 | Williams |
| 4,686,624 A | 8/1987 | Blum et al. |
| 4,698,582 A | 10/1987 | Braun et al. |
| 4,703,756 A | 11/1987 | Gough et al. |
| 4,711,245 A | 12/1987 | Higgins et al. |
| 4,711,251 A | 12/1987 | Stokes |
| 4,714,462 A | 12/1987 | DiDomenico |
| 4,717,673 A | 1/1988 | Wrighton et al. |
| 4,718,893 A | 1/1988 | Dorman |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,051 A | 3/1988 | Fischell |
| 4,731,726 A | 3/1988 | Allen, III |
| 4,747,828 A | 5/1988 | Tseo |
| 4,749,985 A | 6/1988 | Corsberg |
| 4,750,496 A | 6/1988 | Reinhart |
| 4,753,652 A | 6/1988 | Langer et al. |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,787,398 A | 11/1988 | Garcia et al. |
| 4,795,707 A | 1/1989 | Niiyama et al. |
| 4,796,634 A | 1/1989 | Huntsman et al. |
| 4,803,243 A | 2/1989 | Fujimoto et al. |
| 4,803,625 A | 2/1989 | Fu et al. |
| 4,803,726 A | 2/1989 | Levine et al. |
| 4,805,624 A | 2/1989 | Yao et al. |
| 4,805,625 A | 2/1989 | Wyler |
| 4,810,470 A | 3/1989 | Burkhardt et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,826,810 A | 5/1989 | Aoki |
| 4,830,959 A | 5/1989 | McNeil et al. |
| 4,832,034 A | 5/1989 | Pizziconi |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,838,887 A | 6/1989 | Idriss |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,849,458 A | 7/1989 | Reed et al. |
| 4,852,573 A | 8/1989 | Kennedy |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,883,057 A | 11/1989 | Broderick |
| 4,889,744 A | 12/1989 | Quaid |
| 4,890,620 A | 1/1990 | Gough |
| 4,890,621 A | 1/1990 | Hakky |
| 4,894,137 A | 1/1990 | Takizawa et al. |
| 4,896,142 A | 1/1990 | Aycox et al. |
| 4,897,162 A | 1/1990 | Lewandowski et al. |
| 4,897,173 A | 1/1990 | Nankai et al. |
| 4,897,457 A | 1/1990 | Nakamura et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,407 A | 5/1990 | Dorman |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,955,861 A | 9/1990 | Enegren et al. |
| 4,957,115 A | 9/1990 | Selker |
| 4,958,632 A | 9/1990 | Duggan |
| 4,963,595 A | 10/1990 | Ward et al. |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,984,929 A | 1/1991 | Rock et al. |
| 4,986,271 A | 1/1991 | Wilkins |
| 4,986,671 A | 1/1991 | Sun et al. |
| 4,990,845 A | 2/1991 | Gord |
| 4,991,582 A | 2/1991 | Byers et al. |
| 4,992,794 A | 2/1991 | Brouwers |
| 4,994,068 A | 2/1991 | Hufnagle |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,002,572 A | 3/1991 | Picha |
| 5,007,427 A | 4/1991 | Suzuki et al. |
| 5,007,929 A | 4/1991 | Quaid |
| 5,016,172 A | 5/1991 | Dessertine |
| 5,016,201 A | 5/1991 | Bryan et al. |
| 5,016,631 A | 5/1991 | Hogrefe et al. |
| 5,019,974 A | 5/1991 | Beckers |
| 5,027,499 A | 7/1991 | Prohaska |
| 5,030,333 A | 7/1991 | Clark, Jr. |
| 5,034,112 A | 7/1991 | Murase et al. |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,047,044 A | 9/1991 | Smith et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,059,654 A | 10/1991 | Hou et al. |
| 5,063,081 A | 11/1991 | Cozzette et al. |
| 5,067,491 A | 11/1991 | Taylor et al. |
| 5,068,536 A | 11/1991 | Rosenthal |
| 5,070,535 A | 12/1991 | Hochmair et al. |
| 5,073,500 A | 12/1991 | Saito et al. |
| 5,074,977 A | 12/1991 | Cheung et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,088,981 A | 2/1992 | Howson et al. |

| | | | | | | |
|---|---|---|---|---|---|---|
| 5,089,112 A | 2/1992 | Skotheim et al. | | 5,264,105 A | 11/1993 | Gregg et al. |
| 5,094,951 A | 3/1992 | Rosenberg | | 5,264,106 A | 11/1993 | McAleer et al. |
| 5,095,904 A | 3/1992 | Seligman et al. | | 5,265,888 A | 11/1993 | Yamamoto et al. |
| 5,096,560 A | 3/1992 | Takai et al. | | 5,266,179 A | 11/1993 | Nankai et al. |
| 5,096,836 A | 3/1992 | Macho et al. | | 5,269,212 A | 12/1993 | Peters et al. |
| 5,097,834 A | 3/1992 | Skrabal | | 5,269,891 A | 12/1993 | Colin |
| 5,101,814 A | 4/1992 | Palti | | 5,271,736 A | 12/1993 | Picha |
| 5,106,365 A | 4/1992 | Hernandez | | 5,271,815 A | 12/1993 | Wong |
| 5,108,564 A | 4/1992 | Szuminsky et al. | | 5,272,060 A | 12/1993 | Hamamoto et al. |
| 5,108,889 A | 4/1992 | Smith et al. | | 5,275,159 A | 1/1994 | Griebel |
| 5,109,850 A | 5/1992 | Blanco et al. | | 5,276,610 A | 1/1994 | Maeda et al. |
| 5,111,539 A | 5/1992 | Hiruta et al. | | 5,278,079 A | 1/1994 | Gubinski et al. |
| 5,111,818 A | 5/1992 | Suzuji et al. | | 5,279,294 A | 1/1994 | Anderson et al. |
| 5,114,678 A | 5/1992 | Crawford et al. | | 5,281,319 A | 1/1994 | Kaneko et al. |
| 5,120,420 A | 6/1992 | Nankai et al. | | 5,282,848 A | 2/1994 | Schmitt |
| 5,120,421 A | 6/1992 | Glass et al. | | 5,282,950 A | 2/1994 | Dietze et al. |
| 5,122,925 A | 6/1992 | Inpyn | | 5,284,140 A | 2/1994 | Allen et al. |
| 5,126,034 A | 6/1992 | Carter et al. | | 5,284,156 A | 2/1994 | Schramm et al. |
| 5,126,247 A | 6/1992 | Palmer et al. | | 5,284,570 A | 2/1994 | Savage et al. |
| 5,130,009 A | 7/1992 | Marsoner et al. | | 5,284,748 A | 2/1994 | Mroczkowski et al. |
| 5,131,441 A | 7/1992 | Simpson et al. | | 5,285,513 A | 2/1994 | Kaufman et al. |
| 5,133,856 A | 7/1992 | Yamaguchi et al. | | 5,285,792 A | 2/1994 | Sjoquist et al. |
| 5,134,391 A | 7/1992 | Okada | | 5,286,362 A | 2/1994 | Hoenes et al. |
| 5,135,003 A | 8/1992 | Souma | | 5,286,364 A | 2/1994 | Yacynych et al. |
| 5,137,028 A | 8/1992 | Nishimura | | 5,288,636 A | 2/1994 | Pollmann et al. |
| 5,139,023 A | 8/1992 | Stanley et al. | | 5,291,887 A | 3/1994 | Stanley et al. |
| 5,140,393 A | 8/1992 | Hijikihigawa et al. | | 5,293,546 A | 3/1994 | Tadros et al. |
| 5,140,985 A | 8/1992 | Schroeder et al. | | 5,293,877 A | 3/1994 | O'Hara et al. |
| 5,141,868 A | 8/1992 | Shanks et al. | | 5,299,571 A | 4/1994 | Mastrototaro |
| 5,147,725 A | 9/1992 | Pinchuk | | 5,304,127 A | 4/1994 | Kawahara et al. |
| 5,153,827 A | 10/1992 | Coutre et al. | | 5,304,468 A | 4/1994 | Phillips et al. |
| 5,161,532 A | 11/1992 | Joseph | | 5,307,263 A | 4/1994 | Brown |
| 5,165,407 A | 11/1992 | Wilson et al. | | 5,309,919 A | 5/1994 | Snell et al. |
| 5,168,046 A | 12/1992 | Hamamoto et al. | | 5,310,469 A | 5/1994 | Cunningham et al. |
| 5,171,689 A | 12/1992 | Kawaguri et al. | | 5,310,885 A | 5/1994 | Maier et al. |
| 5,174,291 A | 12/1992 | Schoonen et al. | | 5,312,361 A | 5/1994 | Zadini et al. |
| 5,176,644 A | 1/1993 | Srisathapat et al. | | 5,314,450 A | 5/1994 | Thompson |
| 5,176,662 A | 1/1993 | Bartholomew et al. | | 5,314,471 A | 5/1994 | Brauker et al. |
| 5,182,707 A | 1/1993 | Cooper et al. | | 5,316,008 A | 5/1994 | Suga et al. |
| 5,184,359 A | 2/1993 | Tsukumura et al. | | 5,318,521 A | 6/1994 | Slettenmark |
| 5,185,256 A | 2/1993 | Nankai et al. | | 5,320,098 A | 6/1994 | Davidson |
| 5,190,041 A | 3/1993 | Palti | | 5,320,725 A | 6/1994 | Gregg et al. |
| 5,192,415 A | 3/1993 | Yoshioka et al. | | 5,322,063 A | 6/1994 | Allen et al. |
| 5,192,416 A | 3/1993 | Wang et al. | | 5,324,303 A | 6/1994 | Strong et al. |
| 5,193,539 A | 3/1993 | Schulman et al. | | 5,324,316 A | 6/1994 | Schulman et al. |
| 5,193,540 A | 3/1993 | Schulman et al. | | 5,326,356 A | 7/1994 | Della Valle et al. |
| 5,197,322 A | 3/1993 | Indravudh | | 5,326,449 A | 7/1994 | Cunningham |
| 5,198,192 A | 3/1993 | Saito et al. | | 5,328,460 A | 7/1994 | Lord et al. |
| 5,198,367 A | 3/1993 | Aizawa et al. | | 5,330,521 A | 7/1994 | Cohen |
| 5,198,771 A | 3/1993 | Fidler et al. | | 5,330,634 A | 7/1994 | Wong et al. |
| 5,200,051 A | 4/1993 | Cozzette et al. | | 5,331,555 A | 7/1994 | Hashimoto et al. |
| 5,202,261 A | 4/1993 | Musho et al. | | 5,331,966 A | 7/1994 | Bennett et al. |
| 5,205,920 A | 4/1993 | Oyama et al. | | 5,337,258 A | 8/1994 | Dennis |
| 5,206,145 A | 4/1993 | Cattell | | 5,337,747 A | 8/1994 | Neftel |
| 5,208,147 A | 5/1993 | Kagenow et al. | | 5,340,722 A | 8/1994 | Wolfbeis et al. |
| 5,208,154 A | 5/1993 | Weaver et al. | | 5,342,409 A | 8/1994 | Mullett |
| 5,209,229 A | 5/1993 | Gilli | | 5,342,789 A | 8/1994 | Chick et al. |
| 5,215,887 A | 6/1993 | Saito | | 5,343,869 A | 9/1994 | Pross et al. |
| 5,216,597 A | 6/1993 | Beckers | | 5,344,454 A | 9/1994 | Clarke et al. |
| 5,217,442 A | 6/1993 | Davis | | 5,348,788 A | 9/1994 | White |
| 5,217,595 A | 6/1993 | Smith et al. | | 5,350,407 A | 9/1994 | McClure et al. |
| 5,227,042 A | 7/1993 | Zawodzinski et al. | | 5,352,348 A | 10/1994 | Young et al. |
| 5,229,282 A | 7/1993 | Yoshioka et al. | | 5,352,351 A | 10/1994 | White |
| 5,231,988 A | 8/1993 | Wernicke et al. | | 5,354,319 A | 10/1994 | Wyborny et al. |
| 5,232,668 A | 8/1993 | Grant et al. | | 5,354,449 A | 10/1994 | Band et al. |
| 5,235,003 A | 8/1993 | Ward et al. | | 5,356,348 A | 10/1994 | Bellio et al. |
| 5,243,983 A | 9/1993 | Tarr et al. | | 5,356,786 A | 10/1994 | Heller et al. |
| 5,246,867 A | 9/1993 | Lakowicz et al. | | 5,358,514 A | 10/1994 | Schulman et al. |
| 5,249,576 A | 10/1993 | Goldberger et al. | | 5,360,404 A | 11/1994 | Novacek et al. |
| 5,250,439 A | 10/1993 | Musho et al. | | 5,364,797 A | 11/1994 | Olson et al. |
| 5,251,126 A | 10/1993 | Kahn et al. | | 5,366,609 A | 11/1994 | White et al. |
| 5,257,971 A | 11/1993 | Lord et al. | | 5,368,028 A | 11/1994 | Palti |
| 5,257,980 A | 11/1993 | Van Antwerp et al. | | 5,368,224 A | 11/1994 | Richardson et al. |
| 5,259,769 A | 11/1993 | Cruise et al. | | 5,368,562 A | 11/1994 | Blomquist et al. |
| 5,261,401 A | 11/1993 | Baker et al. | | 5,370,622 A | 12/1994 | Livingston et al. |
| 5,262,035 A | 11/1993 | Gregg et al. | | 5,371,687 A | 12/1994 | Holmes, II et al. |
| 5,262,305 A | 11/1993 | Heller et al. | | 5,371,734 A | 12/1994 | Fischer |
| 5,264,103 A | 11/1993 | Yoshioka et al. | | 5,372,133 A | 12/1994 | Hogen |
| 5,264,104 A | 11/1993 | Gregg et al. | | 5,372,427 A | 12/1994 | Padovani et al. |

| Patent | Date | Inventor |
|---|---|---|
| 5,372,719 A | 12/1994 | Afejan et al. |
| 5,375,604 A | 12/1994 | Kelly et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |
| 5,380,422 A | 1/1995 | Negishis et al. |
| 5,380,536 A | 1/1995 | Hubbell et al. |
| 5,382,346 A | 1/1995 | Uenoyama et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,397,848 A | 3/1995 | Yang et al. |
| 5,399,823 A | 3/1995 | McCusker |
| 5,400,782 A | 3/1995 | Beaubiah |
| 5,408,999 A | 4/1995 | Singh et al. |
| 5,410,471 A | 4/1995 | Alyfuku et al. |
| 5,410,474 A | 4/1995 | Fox |
| 5,411,536 A | 5/1995 | Armstrong |
| 5,411,647 A | 5/1995 | Johnson et al. |
| 5,411,866 A | 5/1995 | Luong |
| 5,413,690 A | 5/1995 | Kost et al. |
| 5,422,246 A | 6/1995 | Koopal et al. |
| 5,425,361 A | 6/1995 | Fenzlein et al. |
| 5,426,032 A | 6/1995 | Phillips |
| 5,429,129 A | 7/1995 | Lovejoy et al. |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Diebold et al. |
| 5,438,984 A | 8/1995 | Schoendorfer |
| 5,445,611 A | 8/1995 | Eppstein et al. |
| 5,445,920 A | 8/1995 | Saito |
| 5,451,260 A | 9/1995 | Versteeg et al. |
| 5,452,173 A | 9/1995 | Brannon et al. |
| 5,453,199 A | 9/1995 | Afejan et al. |
| 5,453,278 A | 9/1995 | Chan et al. |
| 5,456,692 A | 10/1995 | Smith, Jr. et al. |
| 5,456,940 A | 10/1995 | Funderburk |
| 5,458,140 A | 10/1995 | Eppstein et al. |
| 5,460,618 A | 10/1995 | Harreld |
| 5,462,051 A | 10/1995 | Oka et al. |
| 5,462,064 A | 10/1995 | D'Angelo et al. |
| 5,462,525 A | 10/1995 | Srisathapat et al. |
| 5,462,645 A | 10/1995 | Albery et al. |
| 5,466,218 A | 11/1995 | Srisathapat et al. |
| 5,469,846 A | 11/1995 | Khan |
| 5,472,317 A | 12/1995 | Field et al. |
| 5,474,552 A | 12/1995 | Palti |
| 5,476,460 A | 12/1995 | Montalvo |
| 5,476,776 A | 12/1995 | Wilkins |
| 5,477,855 A | 12/1995 | Schindler et al. |
| 5,482,008 A | 1/1996 | Stafford et al. |
| 5,482,473 A | 1/1996 | Lord et al. |
| 5,484,404 A | 1/1996 | Schulman et al. |
| 5,487,751 A | 1/1996 | Radons et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,665 A | 3/1996 | Jhuboo et al. |
| 5,501,956 A | 3/1996 | Wada et al. |
| 5,502,396 A | 3/1996 | Desarzens et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,513,636 A | 5/1996 | Palti |
| 5,514,103 A | 5/1996 | Srisathapat et al. |
| 5,514,253 A | 5/1996 | Davis et al. |
| 5,514,718 A | 5/1996 | Lewis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,679 A | 7/1996 | Schulman et al. |
| 5,531,878 A | 7/1996 | Vadgama et al. |
| 5,538,007 A | 7/1996 | Gorman |
| 5,538,511 A | 7/1996 | Van Antwerp et al. |
| 5,540,828 A | 7/1996 | Yacynych |
| 5,544,651 A | 8/1996 | Wilk |
| 5,545,152 A | 8/1996 | Funderburk et al. |
| 5,545,191 A | 8/1996 | Mann et al. |
| 5,545,220 A | 8/1996 | Andrews et al. |
| 5,545,223 A | 8/1996 | Neuenfeldt et al. |
| 5,549,113 A | 8/1996 | Halleck et al. |
| 5,549,115 A | 8/1996 | Morgan et al. |
| 5,549,675 A | 8/1996 | Neuenfeldt et al. |
| 5,551,427 A | 9/1996 | Altman |
| 5,551,953 A | 9/1996 | Lattin et al. |
| 5,552,027 A | 9/1996 | Birkle et al. |
| 5,553,616 A | 9/1996 | Ham et al. |
| 5,554,166 A | 9/1996 | Lange et al. |
| 5,556,524 A | 9/1996 | Albers |
| 5,558,640 A | 9/1996 | Pfeiler et al. |
| 5,560,357 A | 10/1996 | Faupei et al. |
| 5,562,713 A | 10/1996 | Silvian |
| 5,564,439 A | 10/1996 | Picha |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,569,212 A | 10/1996 | Brown |
| 5,569,462 A | 10/1996 | Martinson et al. |
| 5,571,395 A | 11/1996 | Park et al. |
| 5,571,682 A | 11/1996 | Jacobs et al. |
| 5,573,506 A | 11/1996 | Vasko |
| 5,573,647 A | 11/1996 | Maley et al. |
| 5,575,895 A | 11/1996 | Ikeda et al. |
| 5,575,930 A | 11/1996 | Tietje-Girault et al. |
| 5,580,527 A | 12/1996 | Bell et al. |
| 5,580,794 A | 12/1996 | Allen |
| 5,582,184 A | 12/1996 | Erickson et al. |
| 5,582,593 A | 12/1996 | Hultman |
| 5,582,697 A | 12/1996 | Ikeda et al. |
| 5,582,698 A | 12/1996 | Flaherty et al. |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,589,045 A | 12/1996 | Hyodo |
| 5,589,326 A | 12/1996 | Deng et al. |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,594,906 A | 1/1997 | Holmes, II et al. |
| 5,596,150 A | 1/1997 | Arndy et al. |
| 5,596,994 A | 1/1997 | Bro |
| 5,601,435 A | 2/1997 | Quy |
| 5,601,694 A | 2/1997 | Maley et al. |
| 5,605,152 A | 2/1997 | Slate et al. |
| 5,607,565 A | 3/1997 | Azarnia et al. |
| 5,609,575 A | 3/1997 | Larson et al. |
| 5,611,900 A | 3/1997 | Worden et al. |
| 5,615,671 A | 4/1997 | Schoonen et al. |
| 5,616,222 A | 4/1997 | Maley et al. |
| 5,617,851 A | 4/1997 | Lipkovker |
| 5,623,925 A | 4/1997 | Swenson et al. |
| 5,624,537 A | 4/1997 | Turner et al. |
| 5,628,309 A | 5/1997 | Brown |
| 5,628,310 A | 5/1997 | Rao et al. |
| 5,628,890 A | 5/1997 | Carter et al. |
| 5,629,981 A | 5/1997 | Nerlikar |
| 5,637,095 A | 6/1997 | Nason et al. |
| 5,640,764 A | 6/1997 | Strojnik |
| 5,640,954 A | 6/1997 | Pfeiffer et al. |

| Patent No. | Date | Inventor(s) |
|---|---|---|
| 5,642,365 A | 6/1997 | Murakami et al. |
| 5,643,212 A | 7/1997 | Coutre et al. |
| 5,647,853 A | 7/1997 | Feldmann et al. |
| 5,650,062 A | 7/1997 | Ikeda et al. |
| 5,651,767 A | 7/1997 | Schulman et al. |
| 5,651,869 A | 7/1997 | Yoshioka et al. |
| 5,653,239 A | 8/1997 | Pompei et al. |
| 5,653,735 A | 8/1997 | Chen et al. |
| 5,653,756 A | 8/1997 | Clarke et al. |
| 5,653,863 A | 8/1997 | Genshaw et al. |
| 5,658,250 A | 8/1997 | Blomquist et al. |
| 5,658,330 A | 8/1997 | Carlisle et al. |
| 5,660,163 A | 8/1997 | Schulman et al. |
| 5,662,694 A | 9/1997 | Lidman et al. |
| 5,665,065 A | 9/1997 | Colman et al. |
| 5,665,222 A | 9/1997 | Heller et al. |
| 5,667,983 A | 9/1997 | Abel et al. |
| 5,670,031 A | 9/1997 | Hintsche et al. |
| 5,676,820 A | 10/1997 | Wang et al. |
| 5,678,571 A | 10/1997 | Brown |
| 5,679,690 A | 10/1997 | Andre et al. |
| 5,680,858 A | 10/1997 | Hansen et al. |
| 5,682,233 A | 10/1997 | Brinda |
| 5,682,884 A | 11/1997 | Hill et al. |
| 5,686,717 A | 11/1997 | Knowles et al. |
| 5,686,829 A | 11/1997 | Girault |
| 5,695,473 A | 12/1997 | Olsen |
| 5,695,623 A | 12/1997 | Michel et al. |
| 5,695,949 A | 12/1997 | Galen et al. |
| 5,701,894 A | 12/1997 | Cherry et al. |
| 5,704,354 A | 1/1998 | Preidel et al. |
| 5,704,922 A | 1/1998 | Brown |
| 5,706,807 A | 1/1998 | Picha |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff |
| 5,711,861 A | 1/1998 | Ward et al. |
| 5,711,862 A | 1/1998 | Sakoda et al. |
| 5,711,868 A | 1/1998 | Maley et al. |
| 5,713,353 A | 2/1998 | Castano |
| 5,713,888 A | 2/1998 | Neuenfeldt et al. |
| 5,714,123 A | 2/1998 | Sohrab |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,727,548 A | 3/1998 | Hill et al. |
| 5,728,074 A | 3/1998 | Castellano et al. |
| 5,730,124 A | 3/1998 | Yamauchi |
| 5,730,654 A | 3/1998 | Brown |
| 5,733,336 A | 3/1998 | Neuenfeldt et al. |
| 5,735,273 A | 4/1998 | Kurnik et al. |
| 5,735,285 A | 4/1998 | Albert et al. |
| 5,741,211 A | 4/1998 | Renirie et al. |
| 5,741,330 A | 4/1998 | Brauker et al. |
| 5,741,634 A | 4/1998 | Nozoe et al. |
| 5,741,688 A | 4/1998 | Oxenboll et al. |
| 5,743,262 A | 4/1998 | Lepper, Jr. et al. |
| 5,746,217 A | 5/1998 | Erickson et al. |
| 5,748,103 A | 5/1998 | Flach et al. |
| 5,749,832 A | 5/1998 | Vadgama et al. |
| 5,749,907 A | 5/1998 | Mann |
| 5,750,926 A | 5/1998 | Schulman et al. |
| 5,756,632 A | 5/1998 | Ward et al. |
| 5,770,028 A | 6/1998 | Maley et al. |
| 5,771,001 A | 6/1998 | Cobb |
| 5,771,890 A | 6/1998 | Tamada |
| 5,771,891 A | 6/1998 | Gozani |
| 5,772,586 A | 6/1998 | Heinonen et al. |
| 5,777,060 A | 7/1998 | Van Antwerp |
| 5,779,665 A | 7/1998 | Mastrototaro et al. |
| 5,781,455 A | 7/1998 | Hyodo |
| 5,782,814 A | 7/1998 | Brown et al. |
| 5,782,912 A | 7/1998 | Brauker et al. |
| 5,785,681 A | 7/1998 | Indravudh |
| 5,786,439 A | 7/1998 | Van Antwerp et al. |
| 5,786,584 A | 7/1998 | Button et al. |
| 5,787,900 A | 8/1998 | Butler et al. |
| 5,788,678 A | 8/1998 | Van Antwerp |
| 5,791,344 A | 8/1998 | Schulman et al. |
| 5,792,117 A | 8/1998 | Brown |
| 5,795,774 A | 8/1998 | Matsumoto et al. |
| 5,798,065 A | 8/1998 | Picha |
| 5,800,387 A | 9/1998 | Duffy et al. |
| 5,800,420 A | 9/1998 | Gross et al. |
| 5,800,529 A | 9/1998 | Brauker et al. |
| 5,804,048 A | 9/1998 | Wong et al. |
| 5,806,517 A | 9/1998 | Gerhardt et al. |
| 5,807,315 A | 9/1998 | Van Antwerp et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,183 A | 10/1998 | Kurnik et al. |
| 5,827,184 A | 10/1998 | Netherly et al. |
| 5,828,943 A | 10/1998 | Brown |
| 5,830,341 A | 11/1998 | Gilmartin |
| 5,832,448 A | 11/1998 | Brown |
| 5,833,603 A | 11/1998 | Kovacs et al. |
| 5,834,224 A | 11/1998 | Ruger et al. |
| 5,836,887 A | 11/1998 | Oka et al. |
| 5,836,989 A | 11/1998 | Shelton |
| 5,837,454 A | 11/1998 | Cozzette et al. |
| 5,837,546 A | 11/1998 | Allen et al. |
| 5,837,728 A | 11/1998 | Purcell |
| 5,840,020 A | 11/1998 | Heinonen et al. |
| 5,840,148 A | 11/1998 | Campbell et al. |
| 5,840,240 A | 11/1998 | Stenoien et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,857,967 A | 1/1999 | Frid et al. |
| 5,857,983 A | 1/1999 | Douglas et al. |
| 5,860,917 A | 1/1999 | Comanor et al. |
| 5,861,009 A | 1/1999 | Armstrong et al. |
| 5,861,019 A | 1/1999 | Sun et al. |
| 5,862,803 A | 1/1999 | Besson et al. |
| 5,871,465 A | 2/1999 | Vasko |
| 5,871,514 A | 2/1999 | Wiklund et al. |
| 5,872,713 A | 2/1999 | Douglas et al. |
| 5,872,820 A | 2/1999 | Upadrasta |
| 5,876,484 A | 3/1999 | Raskin et al. |
| 5,879,163 A | 3/1999 | Brown et al. |
| 5,879,311 A | 3/1999 | Duchon et al. |
| 5,879,373 A | 3/1999 | Roper et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,885,245 A | 3/1999 | Lynch et al. |
| 5,887,133 A | 3/1999 | Brown et al. |
| 5,895,235 A | 4/1999 | Droz |
| 5,895,371 A | 4/1999 | Levitas et al. |
| 5,897,493 A | 4/1999 | Brown |
| 5,897,578 A | 4/1999 | Wiklund et al. |
| 5,898,025 A | 4/1999 | Burg et al. |
| 5,899,855 A | 5/1999 | Brown |
| 5,899,931 A | 5/1999 | Deschamp et al. |
| 5,904,708 A | 5/1999 | Goedeke |
| 5,913,310 A | 6/1999 | Brown |
| 5,913,827 A | 6/1999 | Gorman |
| 5,913,998 A | 6/1999 | Butler et al. |
| 5,914,026 A | 6/1999 | Blubaugh, Jr. et al. |
| 5,916,445 A | 6/1999 | Hjerten et al. |
| 5,917,346 A | 6/1999 | Gord |
| 5,918,603 A | 7/1999 | Brown |

| | | | | | | |
|---|---|---|---|---|---|---|
| 5,919,215 A | 7/1999 | Wiklund et al. | 6,041,253 A | 3/2000 | Kost et al. | |
| 5,925,021 A | 7/1999 | Castellano et al. | 6,043,437 A | 3/2000 | Schulman et al. | |
| 5,928,130 A | 7/1999 | Schmidt | 6,048,691 A | 4/2000 | Maracas | |
| 5,931,791 A | 8/1999 | Saltzstein et al. | 6,049,727 A | 4/2000 | Crothall | |
| 5,931,814 A | 8/1999 | Alex et al. | 6,051,372 A | 4/2000 | Bayerl et al. | |
| 5,933,136 A | 8/1999 | Brown | 6,056,718 A | 5/2000 | Funderburk et al. | |
| 5,935,099 A | 8/1999 | Peterson et al. | 6,057,377 A | 5/2000 | Sasaki et al. | |
| 5,935,785 A | 8/1999 | Reber et al. | 6,059,946 A | 5/2000 | Yukawa et al. | |
| 5,940,801 A | 8/1999 | Brown | 6,063,459 A | 5/2000 | Velte | |
| 5,942,979 A | 8/1999 | Luppino | 6,063,637 A | 5/2000 | Arnold et al. | |
| 5,944,661 A | 8/1999 | Swette et al. | 6,066,083 A | 5/2000 | Slater et al. | |
| 5,945,345 A | 8/1999 | Blatt et al. | 6,066,243 A | 5/2000 | Anderson et al. | |
| 5,947,749 A | 9/1999 | Rathburn | 6,066,448 A | 5/2000 | Wohlstadter et al. | |
| 5,947,921 A | 9/1999 | Johnson et al. | 6,067,474 A | 5/2000 | Schulman et al. | |
| 5,948,512 A | 9/1999 | Kubota et al. | 6,068,615 A | 5/2000 | Brown et al. | |
| 5,950,632 A | 9/1999 | Reber et al. | 6,071,249 A | 6/2000 | Cunningham et al. | |
| 5,951,300 A | 9/1999 | Brown | 6,071,251 A | 6/2000 | Cunningham et al. | |
| 5,951,492 A | 9/1999 | Douglas et al. | 6,071,294 A | 6/2000 | Simons et al. | |
| 5,951,521 A | 9/1999 | Mastrototaro et al. | 6,071,391 A | 6/2000 | Gotoh et al. | |
| 5,951,836 A | 9/1999 | McAleer et al. | 6,071,406 A | 6/2000 | Tsou | |
| 5,954,643 A | 9/1999 | Van Antwerp | 6,073,049 A | 6/2000 | Alt et al. | |
| 5,954,685 A | 9/1999 | Tierney | 6,081,735 A | 6/2000 | Diab et al. | |
| 5,954,700 A | 9/1999 | Kovelman | 6,081,736 A | 6/2000 | Colvin et al. | |
| 5,954,954 A | 9/1999 | Houck et al. | 6,083,523 A | 7/2000 | Dionne et al. | |
| 5,956,501 A | 9/1999 | Brown | 6,083,710 A * | 7/2000 | Heller et al. | 600/347 |
| 5,957,854 A | 9/1999 | Besson et al. | 6,088,608 A | 7/2000 | Schulman et al. | |
| 5,957,890 A | 9/1999 | Mann et al. | 6,091,975 A | 7/2000 | Daddona et al. | |
| 5,957,903 A | 9/1999 | Mirzaee et al. | 6,091,976 A | 7/2000 | Pfeiffer et al. | |
| 5,957,958 A | 9/1999 | Schulman et al. | 6,093,156 A | 7/2000 | Cunningham et al. | |
| 5,959,050 A | 9/1999 | Mosbach et al. | 6,093,167 A | 7/2000 | Houben et al. | |
| 5,960,403 A | 9/1999 | Brown | 6,093,172 A | 7/2000 | Funderburk et al. | |
| 5,961,451 A | 10/1999 | Reber et al. | 6,097,831 A | 8/2000 | Wieck et al. | |
| 5,963,132 A | 10/1999 | Yoakum | 6,099,484 A | 8/2000 | Douglas et al. | |
| 5,964,804 A | 10/1999 | Brauker et al. | 6,101,478 A | 8/2000 | Brown | |
| 5,964,993 A | 10/1999 | Blubaugh, Jr. et al. | 6,103,033 A | 8/2000 | Say et al. | |
| 5,965,380 A | 10/1999 | Heller et al. | 6,103,533 A | 8/2000 | Hassard et al. | |
| 5,968,839 A | 10/1999 | Blatt et al. | 6,106,780 A | 8/2000 | Douglas et al. | |
| 5,971,922 A | 10/1999 | Arita et al. | 6,107,083 A | 8/2000 | Collins et al. | |
| 5,971,941 A | 10/1999 | Simons et al. | 6,110,148 A | 8/2000 | Brown et al. | |
| 5,974,124 A | 10/1999 | Schlueter, Jr. et al. | 6,110,152 A | 8/2000 | Kovelman | |
| 5,976,085 A | 11/1999 | Kimball et al. | 6,113,537 A | 9/2000 | Castano | |
| 5,977,476 A | 11/1999 | Guha et al. | 6,113,578 A | 9/2000 | Brown | |
| 5,981,294 A | 11/1999 | Blatt et al. | 6,115,634 A | 9/2000 | Donders et al. | |
| 5,985,129 A | 11/1999 | Gough et al. | 6,117,290 A | 9/2000 | Say et al. | |
| 5,987,352 A | 11/1999 | Klein et al. | 6,119,028 A | 9/2000 | Schulman et al. | |
| 5,987,353 A | 11/1999 | Khatchatrian et al. | 6,120,676 A | 9/2000 | Heller et al. | |
| 5,989,409 A | 11/1999 | Kurnik et al. | 6,121,009 A | 9/2000 | Heller et al. | |
| 5,994,476 A | 11/1999 | Shin et al. | 6,121,611 A | 9/2000 | Lindsay et al. | |
| 5,995,860 A | 11/1999 | Sun et al. | 6,122,351 A | 9/2000 | Schlueter, Jr. et al. | |
| 5,997,475 A | 12/1999 | Bortz | 6,122,536 A | 9/2000 | Sun et al. | |
| 5,997,476 A | 12/1999 | Brown | 6,123,827 A | 9/2000 | Wong et al. | |
| 5,999,848 A | 12/1999 | Gord et al. | 6,125,978 A | 10/2000 | Ando et al. | |
| 5,999,849 A | 12/1999 | Gord et al. | 6,134,461 A | 10/2000 | Say et al. | |
| 6,001,067 A | 12/1999 | Shults et al. | 6,134,504 A | 10/2000 | Douglas et al. | |
| 6,001,471 A | 12/1999 | Bries et al. | 6,135,978 A | 10/2000 | Houben et al. | |
| 6,002,954 A | 12/1999 | Van Antwerp et al. | 6,139,718 A | 10/2000 | Kurnik et al. | |
| 6,002,961 A | 12/1999 | Mitragotri et al. | 6,141,573 A | 10/2000 | Kurnik et al. | |
| 6,004,441 A | 12/1999 | Fujiwara et al. | 6,142,939 A | 11/2000 | Eppstein et al. | |
| 6,007,845 A | 12/1999 | Domb | 6,142,972 A | 11/2000 | Cheikh | |
| 6,011,984 A | 1/2000 | Van Antwerp et al. | 6,143,164 A | 11/2000 | Heller et al. | |
| 6,013,113 A | 1/2000 | Mika | 6,144,837 A | 11/2000 | Quy | |
| 6,014,577 A | 1/2000 | Henning et al. | 6,144,869 A | 11/2000 | Berner et al. | |
| 6,015,390 A | 1/2000 | Krag | 6,144,871 A | 11/2000 | Saito et al. | |
| 6,016,448 A | 1/2000 | Busacker et al. | 6,144,922 A | 11/2000 | Douglas et al. | |
| 6,017,435 A | 1/2000 | Hassard et al. | 6,148,094 A | 11/2000 | Kinsella | |
| 6,018,678 A | 1/2000 | Mitragotri et al. | 6,150,128 A | 11/2000 | Uretsky | |
| 6,023,629 A | 2/2000 | Tamada | 6,151,586 A | 11/2000 | Brown | |
| 6,024,699 A | 2/2000 | Surwit et al. | 6,153,062 A | 11/2000 | Saito et al. | |
| 6,026,320 A | 2/2000 | Carlson et al. | 6,153,069 A | 11/2000 | Pottgen et al. | |
| 6,027,445 A | 2/2000 | Von Bahr | 6,154,675 A | 11/2000 | Juran et al. | |
| 6,027,459 A | 2/2000 | Shain et al. | 6,154,676 A | 11/2000 | Levine | |
| 6,027,692 A | 2/2000 | Galen et al. | 6,159,147 A | 12/2000 | Lichter et al. | |
| 6,032,059 A | 2/2000 | Henning et al. | 6,161,095 A | 12/2000 | Brown | |
| 6,032,199 A | 2/2000 | Lim et al. | 6,162,611 A | 12/2000 | Heller et al. | |
| 6,033,866 A | 3/2000 | Guo et al. | 6,162,639 A | 12/2000 | Douglas | |
| 6,034,622 A | 3/2000 | Levine | 6,167,362 A | 12/2000 | Brown et al. | |
| 6,035,237 A | 3/2000 | Schulman et al. | 6,167,614 B1 | 1/2001 | Tuttle et al. | |
| 6,036,924 A | 3/2000 | Simons et al. | 6,168,563 B1 | 1/2001 | Brown | |
| 6,040,194 A | 3/2000 | Chick et al. | 6,168,568 B1 | 1/2001 | Gavriely | |

| Patent No. | Date | Inventor |
|---|---|---|
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,187,062 B1 | 2/2001 | Oweis et al. |
| 6,189,536 B1 | 2/2001 | Martinez et al. |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,200,772 B1 | 3/2001 | Vadgama et al. |
| 6,201,979 B1 | 3/2001 | Kurnik et al. |
| 6,201,980 B1 | 3/2001 | Darrow et al. |
| 6,201,993 B1 | 3/2001 | Kruse et al. |
| 6,206,841 B1 | 3/2001 | Cunningham et al. |
| 6,206,856 B1 | 3/2001 | Mahurkar |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,212,424 B1 | 4/2001 | Robinson |
| 6,214,185 B1 | 4/2001 | Offenbacher et al. |
| 6,219,565 B1 | 4/2001 | Cupp et al. |
| 6,219,574 B1 | 4/2001 | Cormier et al. |
| 6,223,083 B1 | 4/2001 | Rosar |
| 6,223,471 B1 | 5/2001 | Barber |
| 6,224,745 B1 | 5/2001 | Baltruschat |
| 6,230,059 B1 | 5/2001 | Duffin |
| 6,231,879 B1 | 5/2001 | Li et al. |
| 6,232,130 B1 | 5/2001 | Wolf |
| 6,232,370 B1 | 5/2001 | Kubota et al. |
| 6,232,783 B1 | 5/2001 | Merrill |
| 6,233,080 B1 | 5/2001 | Brenner et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,704 B1 | 6/2001 | Peterson et al. |
| 6,241,862 B1 | 6/2001 | McAleer et al. |
| 6,241,863 B1 | 6/2001 | Monbouquette |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,251,280 B1 | 6/2001 | Dai et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,522 B1 | 7/2001 | Schultz |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,264,825 B1 | 7/2001 | Blackburn et al. |
| 6,266,645 B1 | 7/2001 | Simpson |
| 6,267,724 B1 | 7/2001 | Taylor |
| 6,268,161 B1 | 7/2001 | Han et al. |
| 6,268,913 B1 | 7/2001 | Rising |
| 6,270,445 B1 | 8/2001 | Dean, Jr. et al. |
| 6,272,364 B1 | 8/2001 | Kurnik |
| 6,272,480 B1 | 8/2001 | Tresp et al. |
| 6,274,285 B1 | 8/2001 | Gries et al. |
| 6,274,686 B1 | 8/2001 | Mosbach et al. |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,761 B1 | 9/2001 | Joao |
| 6,283,943 B1 | 9/2001 | Dy et al. |
| 6,284,126 B1 | 9/2001 | Kurnik et al. |
| 6,284,478 B1 | 9/2001 | Heller et al. |
| 6,285,897 B1 | 9/2001 | Kilcoyne et al. |
| 6,289,238 B1 | 9/2001 | Besson et al. |
| 6,293,925 B1 | 9/2001 | Safabash et al. |
| 6,294,281 B1 | 9/2001 | Heller |
| 6,295,463 B1 | 9/2001 | Stenzler |
| 6,295,506 B1 | 9/2001 | Heinonen et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,300,002 B1 | 10/2001 | Webb et al. |
| 6,301,499 B1 | 10/2001 | Carlson et al. |
| 6,302,855 B1 | 10/2001 | Knobbe et al. |
| 6,304,766 B1 | 10/2001 | Colvin, Jr. et al. |
| 6,306,104 B1 | 10/2001 | Cunningham et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,309,884 B1 | 10/2001 | Cooper et al. |
| 6,310,110 B1 | 10/2001 | Markowitz et al. |
| 6,315,721 B2 | 11/2001 | Schulman et al. |
| 6,315,738 B1 | 11/2001 | Nishikawa et al. |
| 6,319,540 B1 | 11/2001 | Van Antwerp et al. |
| 6,319,566 B1 | 11/2001 | Polanyi et al. |
| 6,320,357 B1 | 11/2001 | Peters et al. |
| 6,324,428 B1 | 11/2001 | Weinberg et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,340,588 B1 | 1/2002 | Nova et al. |
| 6,341,232 B1 | 1/2002 | Conn et al. |
| 6,343,225 B1 | 1/2002 | Clark, Jr. |
| 6,348,640 B1 | 2/2002 | Navot et al. |
| 6,352,505 B1 | 3/2002 | Bortz |
| 6,356,776 B1 | 3/2002 | Berner et al. |
| 6,358,237 B1 | 3/2002 | Paukovits et al. |
| 6,359,444 B1 | 3/2002 | Grimes |
| 6,360,888 B1 | 3/2002 | McIvor et al. |
| 6,363,282 B1 | 3/2002 | Nichols et al. |
| 6,365,670 B1 | 4/2002 | Fry |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,272 B1 | 4/2002 | Porumbescu |
| 6,368,274 B1 | 4/2002 | Van Antwerp et al. |
| 6,370,410 B2 | 4/2002 | Kurnik et al. |
| 6,377,828 B1 | 4/2002 | Chaiken et al. |
| 6,379,301 B1 | 4/2002 | Worthington et al. |
| 6,379,317 B1 | 4/2002 | Kintzig et al. |
| 6,383,767 B1 | 5/2002 | Polak |
| 6,387,048 B1 | 5/2002 | Schulman et al. |
| 6,391,643 B1 | 5/2002 | Chen et al. |
| 6,393,318 B1 | 5/2002 | Conn et al. |
| 6,398,562 B1 | 6/2002 | Butler et al. |
| 6,398,727 B1 | 6/2002 | Bui et al. |
| 6,402,689 B1 | 6/2002 | Scarantino et al. |
| 6,402,691 B1 | 6/2002 | Peddicord et al. |
| 6,405,066 B1 | 6/2002 | Essenpreis et al. |
| 6,406,066 B1 | 6/2002 | Uegane |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,416,471 B1 | 7/2002 | Kumar et al. |
| 6,416,651 B1 | 7/2002 | Millar |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,424,867 B1 | 7/2002 | Snell et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,441,747 B1 | 8/2002 | Khair et al. |
| 6,442,433 B1 | 8/2002 | Linberg |
| 6,442,637 B1 | 8/2002 | Hawkins et al. |
| 6,443,942 B2 | 9/2002 | Van Antwerp et al. |

| Patent | Date | Inventor |
|---|---|---|
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,462,162 B2 | 10/2002 | Van Antwerp et al. |
| 6,464,687 B1 | 10/2002 | Ishikawa et al. |
| 6,464,848 B1 | 10/2002 | Matsumoto |
| 6,464,849 B1 | 10/2002 | Say et al. |
| 6,466,810 B1 | 10/2002 | Ward et al. |
| 6,468,222 B1 | 10/2002 | Mault et al. |
| 6,469,526 B1 | 10/2002 | Franklin |
| 6,471,645 B1 | 10/2002 | Warkentin et al. |
| 6,471,689 B1 | 10/2002 | Joseph et al. |
| 6,472,122 B1 | 10/2002 | Schulman et al. |
| 6,475,180 B2 | 11/2002 | Peterson et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,478,736 B1 | 11/2002 | Mault |
| 6,480,730 B2 | 11/2002 | Darrow et al. |
| 6,481,440 B2 | 11/2002 | Gielen et al. |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,485,465 B2 | 11/2002 | Moberg et al. |
| 6,487,429 B2 | 11/2002 | Hockersmith et al. |
| 6,494,830 B1 | 12/2002 | Wessel |
| 6,496,728 B2 | 12/2002 | Li et al. |
| 6,498,043 B1 | 12/2002 | Schulman et al. |
| 6,498,941 B1 | 12/2002 | Jackson |
| 6,505,059 B1 | 1/2003 | Kollias et al. |
| 6,510,329 B2 | 1/2003 | Heckel |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,528,584 B2 | 3/2003 | Kennedy et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,534,711 B1 | 3/2003 | Pollack |
| 6,535,753 B1 | 3/2003 | Raskas |
| 6,537,243 B1 | 3/2003 | Henning et al. |
| 6,537,318 B1 | 3/2003 | Ita et al. |
| 6,540,675 B2 | 4/2003 | Aceti et al. |
| 6,541,107 B1 | 4/2003 | Zhong et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,549,796 B2 | 4/2003 | Sohrab |
| 6,551,276 B1 | 4/2003 | Mann et al. |
| 6,551,494 B1 | 4/2003 | Heller et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 * | 5/2003 | Heller et al. ............... 600/347 |
| 6,561,978 B1 | 5/2003 | Conn et al. |
| 6,562,001 B2 * | 5/2003 | Lebel et al. ............... 604/65 |
| 6,564,105 B2 | 5/2003 | Starkweather et al. |
| 6,565,509 B1 | 5/2003 | Say et al. |
| 6,569,521 B1 | 5/2003 | Sheridan et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,576,101 B1 | 6/2003 | Heller et al. |
| 6,576,117 B1 | 6/2003 | Iketaki et al. |
| 6,577,893 B1 | 6/2003 | Besson et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,588,644 B2 | 7/2003 | Simon |
| 6,589,205 B1 | 7/2003 | Meadows |
| 6,589,229 B1 | 7/2003 | Connelly et al. |
| 6,591,125 B1 * | 7/2003 | Buse et al. ............... 600/347 |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,072 B2 | 8/2003 | Struys et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,658 B1 | 8/2003 | Heller et al. |
| 6,610,012 B2 | 8/2003 | Mault |
| 6,612,306 B1 | 9/2003 | Mault |
| 6,612,984 B1 | 9/2003 | Kerr |
| 6,613,379 B2 | 9/2003 | Ward et al. |
| 6,615,078 B1 | 9/2003 | Burson et al. |
| 6,616,819 B1 | 9/2003 | Liamos et al. |
| 6,618,603 B2 | 9/2003 | Varalli et al. |
| 6,618,934 B1 | 9/2003 | Feldman et al. |
| 6,620,106 B2 | 9/2003 | Mault |
| 6,627,058 B1 | 9/2003 | Chan |
| 6,629,776 B2 | 10/2003 | Bell et al. |
| 6,629,934 B2 | 10/2003 | Mault et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,638,772 B1 | 10/2003 | Douglas et al. |
| 6,641,533 B2 | 11/2003 | Causey, III et al. |
| 6,642,015 B2 | 11/2003 | Vachon et al. |
| 6,644,321 B1 | 11/2003 | Behm |
| 6,645,142 B2 | 11/2003 | Braig et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,596 B1 | 1/2004 | Sayler et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,683,535 B1 | 1/2004 | Utke |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,689,091 B2 | 2/2004 | Bui et al. |
| 6,689,265 B2 | 2/2004 | Heller et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,704,587 B1 | 3/2004 | Kumar et al. |
| 6,705,833 B2 | 3/2004 | Tam et al. |
| 6,708,049 B1 | 3/2004 | Berson et al. |
| 6,711,423 B2 | 3/2004 | Colvin, Jr. |
| 6,721,587 B2 | 4/2004 | Gough |
| 6,723,046 B2 | 4/2004 | Lichtenstein et al. |
| 6,728,560 B2 | 4/2004 | Kollias et al. |

| | | |
|---|---|---|
| 6,730,200 B1 | 5/2004 | Stewart et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,773,565 B2 | 8/2004 | Kunimoto et al. |
| 6,780,297 B2 | 8/2004 | Matsumoto |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,793,802 B2 | 9/2004 | Lee et al. |
| 6,794,195 B2 | 9/2004 | Colvin, Jr. |
| 6,799,149 B2 | 9/2004 | Hartlaub |
| 6,800,451 B2 | 10/2004 | Daniloff et al. |
| 6,801,041 B2 | 10/2004 | Karinka et al. |
| 6,801,420 B2 | 10/2004 | Talbot et al. |
| 6,802,957 B2 | 10/2004 | Jung et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,516 B2 | 11/2004 | Ujhelyi et al. |
| 6,813,519 B2 | 11/2004 | Lebel et al. |
| 6,815,186 B2 | 11/2004 | Clark, Jr. |
| 6,816,742 B2 | 11/2004 | Kim et al. |
| 6,835,553 B2 | 12/2004 | Han et al. |
| RE38,681 E | 1/2005 | Kurnik et al. |
| 6,837,858 B2 | 1/2005 | Cunningham et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,855,115 B2 | 2/2005 | Fonseca et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,869,413 B2 | 3/2005 | Langley et al. |
| 6,872,200 B2 | 3/2005 | Mann et al. |
| 6,873,268 B2 | 3/2005 | Lebel et al. |
| 6,875,386 B1 | 4/2005 | Ward et al. |
| 6,879,849 B2 | 4/2005 | Begic |
| 6,881,551 B2 | 4/2005 | Heller et al. |
| 6,882,940 B2 | 4/2005 | Potts et al. |
| 6,885,883 B2 | 4/2005 | Parris et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| 6,922,584 B2 | 7/2005 | Wang et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,932,084 B2 | 8/2005 | Estes et al. |
| 6,932,894 B2 | 8/2005 | Mao et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,942,518 B2 | 9/2005 | Liamos et al. |
| 6,946,996 B2 | 9/2005 | Koyama |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,952,604 B2 | 10/2005 | DeNuzzio et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,965,791 B1 | 11/2005 | Hitchcock et al. |
| 6,968,294 B2 | 11/2005 | Gutta et al. |
| 6,968,375 B1 | 11/2005 | Brown |
| 6,971,274 B2 | 12/2005 | Olin |
| 6,973,706 B2 | 12/2005 | Say et al. |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,016,721 B2 | 3/2006 | Lee et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,034,677 B2 | 4/2006 | Steinthal et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bagulla et al. |
| 7,052,472 B1 | 5/2006 | Miller et al. |
| 7,052,483 B2 | 5/2006 | Wojcik |
| 7,056,302 B2 | 6/2006 | Douglas |
| 7,060,059 B2 | 6/2006 | Keith et al. |
| 7,070,580 B2 | 7/2006 | Nielsen |
| 7,072,718 B2 | 7/2006 | VonArx et al. |
| 7,072,802 B2 | 7/2006 | Hartlaub |
| 7,074,307 B2 | 7/2006 | Simpson et al. |
| 7,081,195 B2 | 7/2006 | Simpson et al. |
| 7,082,334 B2 | 7/2006 | Boute et al. |
| 7,098,803 B2 | 8/2006 | Mann et al. |
| 7,108,778 B2 | 9/2006 | Simpson et al. |
| 7,109,878 B2 | 9/2006 | Mann et al. |
| 7,110,803 B2 | 9/2006 | Shults et al. |
| 7,113,821 B1 | 9/2006 | Sun et al. |
| 7,115,884 B1 | 10/2006 | Walt et al. |
| 7,118,667 B2 | 10/2006 | Lee |
| 7,133,710 B2 | 11/2006 | Acosta et al. |
| 7,134,999 B2 | 11/2006 | Brauker et al. |

| Patent No. | Date | Inventor |
|---|---|---|
| 7,136,689 B2 | 11/2006 | Shults et al. |
| 7,137,964 B2 | 11/2006 | Flaherty |
| 7,150,975 B2 | 12/2006 | Tamada et al. |
| 7,163,511 B2 | 1/2007 | Conn et al. |
| 7,166,074 B2 | 1/2007 | Reghabit et al. |
| 7,169,289 B2 | 1/2007 | Shulein et al. |
| 7,171,274 B2 | 1/2007 | Starkweather et al. |
| 7,177,690 B2 | 2/2007 | Woods et al. |
| 7,183,068 B2 | 2/2007 | Burson et al. |
| 7,183,102 B2 | 2/2007 | Monfre et al. |
| 7,187,528 B2 | 3/2007 | Talbot et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,215,991 B2 | 5/2007 | Besson et al. |
| 7,225,535 B2 | 6/2007 | Feldman et al. |
| 7,226,978 B2 | 6/2007 | Tapsak et al. |
| 7,228,163 B2 | 6/2007 | Ackerman |
| 7,233,817 B2 | 6/2007 | Yen |
| 7,248,929 B2 | 7/2007 | Meadows et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,396 B2 | 6/2008 | Samuels et al. |
| 7,399,277 B2 | 7/2008 | Saidara et al. |
| 7,402,153 B2 | 7/2008 | Steil et al. |
| 7,406,105 B2 | 7/2008 | DelMain et al. |
| 7,424,318 B2 | 9/2008 | Brister et al. |
| 7,426,408 B2 | 9/2008 | DeNuzzio et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2001/0051768 A1 | 12/2001 | Schulman et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0009810 A1 | 1/2002 | O'Connor et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019330 A1 | 2/2002 | Murray et al. |
| 2002/0019586 A1 | 2/2002 | Teller et al. |
| 2002/0019748 A1 | 2/2002 | Brown |
| 2002/0022883 A1 | 2/2002 | Burg |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065453 A1 | 5/2002 | Lesho et al. |
| 2002/0068858 A1 | 6/2002 | Braig et al. |
| 2002/0068860 A1 | 6/2002 | Clark, Jr. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0084196 A1 | 7/2002 | Liamos et al. |
| 2002/0087056 A1 | 7/2002 | Aceti et al. |
| 2002/0091312 A1 | 7/2002 | Berner et al. |
| 2002/0099282 A1 | 7/2002 | Knobbe et al. |
| 2002/0099997 A1 | 7/2002 | Piret |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0111547 A1 | 8/2002 | Knobbe et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0161286 A1 | 10/2002 | Gerber et al. |
| 2002/0161288 A1 | 10/2002 | Shin et al. |
| 2002/0177764 A1 | 11/2002 | Sohrab |
| 2002/0182241 A1 | 12/2002 | Boerenstein et al. |
| 2002/0188185 A1 | 12/2002 | Sohrab |
| 2002/0193885 A1 | 12/2002 | Legeay et al. |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023182 A1 | 1/2003 | Mault et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0059631 A1 | 3/2003 | Al-Lamee |
| 2003/0065254 A1 | 4/2003 | Schulman et al. |

| | | |
|---|---|---|
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181794 A1 | 9/2003 | Rini et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0188427 A1 | 10/2003 | Say et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199744 A1 | 10/2003 | Buse et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225437 A1 | 12/2003 | Ferguson |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0018486 A1 | 1/2004 | Dunn et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039256 A1 | 2/2004 | Kawatahara et al. |
| 2004/0039298 A1 | 2/2004 | Abreu |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064068 A1 | 4/2004 | DeNuzzio et al. |
| 2004/0068230 A1 | 4/2004 | Estes et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0074785 A1 | 4/2004 | Holker |
| 2004/0078219 A1 | 4/2004 | Kaylor |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0173472 A1 | 9/2004 | Jung et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0204687 A1 | 10/2004 | Mogensen et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0114068 A1 | 5/2005 | Chey et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0139489 A1 | 6/2005 | Oliver et al. |

| | | | | | | |
|---|---|---|---|---|---|---|
| 2005/0143635 A1 | 6/2005 | Kamath et al. | | 2006/0183984 A1 | 8/2006 | Dobbles et al. |
| 2005/0143636 A1 | 6/2005 | Zhang et al. | | 2006/0183985 A1 | 8/2006 | Brister et al. |
| 2005/0143675 A1 | 6/2005 | Neel et al. | | 2006/0189856 A1 | 8/2006 | Petisce et al. |
| 2005/0148003 A1 | 7/2005 | Kieth et al. | | 2006/0189863 A1 | 8/2006 | Heller et al. |
| 2005/0154271 A1 | 7/2005 | Rasdal et al. | | 2006/0195029 A1 | 8/2006 | Shults et al. |
| 2005/0161346 A1 | 7/2005 | Simpson et al. | | 2006/0198864 A1 | 9/2006 | Shults et al. |
| 2005/0171503 A1 | 8/2005 | Van Den Berghe et al. | | 2006/0200019 A1 | 9/2006 | Petisce et al. |
| 2005/0171513 A1 | 8/2005 | Mann et al. | | 2006/0200020 A1 | 9/2006 | Brister et al. |
| 2005/0173245 A1 | 8/2005 | Feldman et al. | | 2006/0200022 A1 | 9/2006 | Brauker et al. |
| 2005/0176136 A1 | 8/2005 | Burd et al. | | 2006/0211921 A1 | 9/2006 | Brauker et al. |
| 2005/0177036 A1 | 8/2005 | Shults et al. | | 2006/0222566 A1 | 10/2006 | Brauker et al. |
| 2005/0181012 A1 | 8/2005 | Saint et al. | | 2006/0224108 A1 | 10/2006 | Brauker et al. |
| 2005/0182306 A1 | 8/2005 | Sloan | | 2006/0224109 A1 | 10/2006 | Steil et al. |
| 2005/0182451 A1 | 8/2005 | Griffin et al. | | 2006/0226985 A1 | 10/2006 | Goodnow et al. |
| 2005/0187720 A1 | 8/2005 | Goode, Jr. et al. | | 2006/0247508 A1 | 11/2006 | Fennell |
| 2005/0192557 A1 | 9/2005 | Brauker et al. | | 2006/0247985 A1 | 11/2006 | Liamos et al. |
| 2005/0195930 A1 | 9/2005 | Spital et al. | | 2006/0258761 A1 | 11/2006 | Boock et al. |
| 2005/0199494 A1 | 9/2005 | Say et al. | | 2006/0258929 A1 | 11/2006 | Goode, Jr. et al. |
| 2005/0203360 A1 | 9/2005 | Brauker et al. | | 2006/0270922 A1 | 11/2006 | Brauker et al. |
| 2005/0203707 A1 | 9/2005 | Tsutsui et al. | | 2006/0270923 A1 | 11/2006 | Brauker et al. |
| 2005/0211571 A1 | 9/2005 | Schulein et al. | | 2006/0281985 A1 | 12/2006 | Ward et al. |
| 2005/0214892 A1 | 9/2005 | Kovatchev et al. | | 2007/0016381 A1 | 1/2007 | Kamath et al. |
| 2005/0215871 A1 | 9/2005 | Feldman et al. | | 2007/0017805 A1 | 1/2007 | Hodges et al. |
| 2005/0215872 A1 | 9/2005 | Berner et al. | | 2007/0027381 A1 | 2/2007 | Stafford |
| 2005/0239154 A1 | 10/2005 | Feldman et al. | | 2007/0027384 A1 | 2/2007 | Brister et al. |
| 2005/0239156 A1 | 10/2005 | Drucker et al. | | 2007/0027385 A1 | 2/2007 | Brister et al. |
| 2005/0241957 A1 | 11/2005 | Mao et al. | | 2007/0032706 A1 | 2/2007 | Kamath et al. |
| 2005/0242479 A1 | 11/2005 | Petisce et al. | | 2007/0032717 A1 | 2/2007 | Brister et al. |
| 2005/0245795 A1 | 11/2005 | Goode, Jr. et al. | | 2007/0032718 A1 | 2/2007 | Shults et al. |
| 2005/0245799 A1 | 11/2005 | Brauker et al. | | 2007/0038044 A1 | 2/2007 | Dobbles et al. |
| 2005/0251083 A1 | 11/2005 | Carr-Brendel et al. | | 2007/0045902 A1 | 3/2007 | Brauker et al. |
| 2005/0261563 A1 | 11/2005 | Zhou et al. | | 2007/0049873 A1 | 3/2007 | Hansen et al. |
| 2005/0261660 A1 | 11/2005 | Choi | | 2007/0060814 A1 | 3/2007 | Stafford |
| 2005/0267780 A1 | 12/2005 | Ray et al. | | 2007/0066873 A1 | 3/2007 | Kamath et al. |
| 2005/0271546 A1 | 12/2005 | Gerber et al. | | 2007/0073129 A1 | 3/2007 | Shah et al. |
| 2005/0271547 A1 | 12/2005 | Gerber et al. | | 2007/0078320 A1 | 4/2007 | Stafford |
| 2005/0272640 A1 | 12/2005 | Doyle, III et al. | | 2007/0078321 A1 | 4/2007 | Mazza et al. |
| 2005/0272985 A1 | 12/2005 | Kotulla et al. | | 2007/0078322 A1 | 4/2007 | Stafford |
| 2005/0277164 A1 | 12/2005 | Drucker et al. | | 2007/0093704 A1 | 4/2007 | Brister et al. |
| 2005/0287620 A1 | 12/2005 | Heller et al. | | 2007/0106135 A1 | 5/2007 | Sloan et al. |
| 2006/0001538 A1 | 1/2006 | Kraft et al. | | 2007/0149873 A1 | 6/2007 | Say et al. |
| 2006/0001550 A1 | 1/2006 | Mann et al. | | 2007/0149874 A1 | 6/2007 | Say et al. |
| 2006/0001551 A1 | 1/2006 | Kraft et al. | | 2007/0149875 A1* | 6/2007 | Ouyang et al. ................ 600/347 |
| 2006/0003398 A1 | 1/2006 | Heller et al. | | 2007/0151869 A1 | 7/2007 | Heller et al. |
| 2006/0004271 A1 | 1/2006 | Peyser et al. | | 2007/0161879 A1 | 7/2007 | Say et al. |
| 2006/0007017 A1 | 1/2006 | Mann et al. | | 2007/0161880 A1 | 7/2007 | Say et al. |
| 2006/0010098 A1 | 1/2006 | Goodnow et al. | | 2007/0163880 A1 | 7/2007 | Woo et al. |
| 2006/0015020 A1 | 1/2006 | Neale et al. | | 2007/0173706 A1 | 7/2007 | Neinast et al. |
| 2006/0015024 A1 | 1/2006 | Brister et al. | | 2007/0179370 A1 | 8/2007 | Say et al. |
| 2006/0016700 A1 | 1/2006 | Brister et al. | | 2007/0179372 A1 | 8/2007 | Say et al. |
| 2006/0019327 A1 | 1/2006 | Brister et al. | | 2007/0191699 A1 | 8/2007 | Say et al. |
| 2006/0020186 A1 | 1/2006 | Brister et al. | | 2007/0191700 A1 | 8/2007 | Say et al. |
| 2006/0020187 A1 | 1/2006 | Brister et al. | | 2007/0191701 A1 | 8/2007 | Feldman et al. |
| 2006/0020188 A1 | 1/2006 | Kamath et al. | | 2007/0197889 A1 | 8/2007 | Brister et al. |
| 2006/0020189 A1 | 1/2006 | Brister et al. | | 2007/0197890 A1 | 8/2007 | Boock et al. |
| 2006/0020190 A1 | 1/2006 | Kamath et al. | | 2007/0203407 A1 | 8/2007 | Hoss et al. |
| 2006/0020191 A1 | 1/2006 | Brister et al. | | 2007/0203408 A1 | 8/2007 | Say et al. |
| 2006/0020192 A1 | 1/2006 | Brister et al. | | 2007/0203410 A1 | 8/2007 | Say et al. |
| 2006/0025663 A1 | 2/2006 | Talbot et al. | | 2007/0203411 A1 | 8/2007 | Say et al. |
| 2006/0031094 A1 | 2/2006 | Cohen et al. | | 2007/0203966 A1 | 8/2007 | Brauker et al. |
| 2006/0036139 A1 | 2/2006 | Brister et al. | | 2007/0208244 A1 | 9/2007 | Brauker et al. |
| 2006/0036140 A1 | 2/2006 | Brister et al. | | 2007/0208245 A1 | 9/2007 | Brauker et al. |
| 2006/0036141 A1 | 2/2006 | Kamath et al. | | 2007/0208246 A1 | 9/2007 | Brauker et al. |
| 2006/0036142 A1 | 2/2006 | Brister et al. | | 2007/0208247 A1 | 9/2007 | Say et al. |
| 2006/0036143 A1 | 2/2006 | Brister et al. | | 2007/0213610 A1 | 9/2007 | Say et al. |
| 2006/0036144 A1 | 2/2006 | Brister et al. | | 2007/0213611 A1 | 9/2007 | Simpson et al. |
| 2006/0036145 A1 | 2/2006 | Brister et al. | | 2007/0215491 A1 | 9/2007 | Heller et al. |
| 2006/0036187 A1 | 2/2006 | Vos et al. | | 2007/0218097 A1 | 9/2007 | Heller et al. |
| 2006/0040402 A1 | 2/2006 | Brauker et al. | | 2007/0232878 A1 | 10/2007 | Kovatchev et al. |
| 2006/0052679 A1 | 3/2006 | Kotulla et al. | | 2007/0235331 A1 | 10/2007 | Simpson et al. |
| 2006/0058602 A1 | 3/2006 | Kwiatkowski et al. | | 2007/0244380 A1 | 10/2007 | Say et al. |
| 2006/0063218 A1 | 3/2006 | Bartkowiak et al. | | 2007/0249919 A1 | 10/2007 | Say et al. |
| 2006/0068208 A1 | 3/2006 | Tapsak et al. | | 2007/0249920 A1 | 10/2007 | Say et al. |
| 2006/0074564 A1 | 4/2006 | Bartkowiak et al. | | 2007/0249922 A1 | 10/2007 | Peyser et al. |
| 2006/0086624 A1 | 4/2006 | Tapsak et al. | | 2008/0009692 A1 | 1/2008 | Stafford |
| 2006/0100588 A1 | 5/2006 | Brunnberg et al. | | 2008/0017522 A1 | 1/2008 | Heller et al. |
| 2006/0155180 A1 | 7/2006 | Brister et al. | | 2008/0021436 A1 | 1/2008 | Wolpert et al. |
| 2006/0166629 A1 | 7/2006 | Reggiardo | | 2008/0021666 A1 | 1/2008 | Goode, Jr. et al. |
| 2006/0173444 A1 | 8/2006 | Choy et al. | | 2008/0029391 A1 | 2/2008 | Mao et al. |

| | | |
|---|---|---|
| 2008/0033254 A1 | 2/2008 | Kamath et al. |
| 2008/0033271 A1 | 2/2008 | Say et al. |
| 2008/0039702 A1 | 2/2008 | Hayter et al. |
| 2008/0045824 A1 | 2/2008 | Tapsak et al. |
| 2008/0071156 A1 | 3/2008 | Brister et al. |
| 2008/0076997 A1 | 3/2008 | Peyser et al. |
| 2008/0083617 A1 | 4/2008 | Simpson et al. |
| 2008/0086039 A1 | 4/2008 | Heller et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0091096 A1 | 4/2008 | Say et al. |
| 2008/0108942 A1 | 5/2008 | Brister et al. |
| 2008/0154101 A1 | 6/2008 | Jain et al. |
| 2008/0167543 A1 | 7/2008 | Say et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214914 A1 | 9/2008 | Say et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262329 A1 | 10/2008 | Say et al. |
| 2008/0262469 A1 | 10/2008 | Brister et al. |
| 2008/0269672 A1 | 10/2008 | Say et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0319292 A1 | 12/2008 | Say et al. |
| 2009/0011449 A1 | 1/2009 | Karinka et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0030297 A1 | 1/2009 | Miller et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062634 A1 | 3/2009 | Say et al. |
| 2009/0062635 A1 | 3/2009 | Brauker et al. |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0089999 A1 | 4/2009 | Say et al. |
| 2009/0093696 A1 | 4/2009 | Say et al. |
| 2009/0099432 A1 | 4/2009 | Say et al. |
| 2009/0099435 A1 | 4/2009 | Say et al. |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163781 A1 | 6/2009 | Say et al. |
| 2009/0163788 A1 | 6/2009 | Say et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0171179 A1 | 7/2009 | Say et al. |
| 2009/0173628 A1 | 7/2009 | Say et al. |
| 2009/0177054 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0178459 A1 | 7/2009 | Li et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182217 A1 | 7/2009 | Li et al. |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0192366 A1 | 7/2009 | Mensinger et al. |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203978 A1 | 8/2009 | Say et al. |
| 2009/0203981 A1 | 8/2009 | Brauker et al. |
| 2009/0204341 A1 | 8/2009 | Brauker et al. |
| 2009/0209838 A1 | 8/2009 | Say et al. |
| 2009/0216100 A1 | 8/2009 | Ebner et al. |
| 2009/0216101 A1 | 8/2009 | Say et al. |

| | | | | | | |
|---|---|---|---|---|---|---|
| 2009/0216103 A1 | 8/2009 | Brister et al. | EP | 0561966 | 10/1994 | |
| 2009/0227940 A1 | 9/2009 | Say et al. | EP | 0286118 | 1/1995 | |
| 2009/0227941 A1 | 9/2009 | Say et al. | EP | 0776628 | 6/1997 | |
| 2009/0228214 A1 | 9/2009 | Say et al. | EP | 0800082 | 10/1997 | |
| 2009/0240120 A1 | 9/2009 | Mensinger et al. | EP | 0817809 | 1/1998 | |
| 2009/0240128 A1 | 9/2009 | Mensinger et al. | EP | 0838230 | 4/1998 | |
| 2009/0240193 A1 | 9/2009 | Mensinger et al. | EP | 0880936 | 12/1998 | |
| 2009/0242399 A1 | 10/2009 | Kamath et al. | EP | 0885932 | 12/1998 | |
| 2009/0242425 A1 | 10/2009 | Kamath et al. | EP | 0967788 | 12/1999 | |
| 2009/0247855 A1 | 10/2009 | Boock et al. | EP | 0970655 | 1/2000 | |
| 2009/0247856 A1 | 10/2009 | Boock et al. | EP | 1034734 | 9/2000 | |
| 2009/0281406 A1 | 11/2009 | McGarraugh et al. | EP | 1048264 | 11/2000 | |
| 2009/0287073 A1 | 11/2009 | Boock et al. | EP | 1077634 | 2/2001 | |
| 2009/0287074 A1 | 11/2009 | Shults et al. | EP | 1078258 | 2/2001 | |
| 2009/0299155 A1 | 12/2009 | Yang et al. | EP | 1355568 | 10/2003 | |
| 2009/0299156 A1 | 12/2009 | Simpson et al. | EP | 2187555 | 5/2010 | |
| 2009/0299162 A1 | 12/2009 | Brauker et al. | WO | WO-85/05119 | 11/1985 | |
| 2009/0299276 A1 | 12/2009 | Brauker et al. | WO | WO-86/00513 | 1/1986 | |
| 2010/0010324 A1 | 1/2010 | Brauker et al. | WO | WO-86/05339 | 9/1986 | |
| 2010/0010331 A1 | 1/2010 | Brauker et al. | WO | WO-87/00513 | 1/1987 | |
| 2010/0010332 A1 | 1/2010 | Brauker et al. | WO | WO-87/06040 | 10/1987 | |
| 2010/0016687 A1 | 1/2010 | Brauker et al. | WO | WO-89/02246 | 3/1989 | |
| 2010/0016698 A1 | 1/2010 | Rasdal et al. | WO | WO-89/02720 | 4/1989 | |
| 2010/0022855 A1 | 1/2010 | Brauker et al. | WO | WO-89/05119 | 6/1989 | |
| 2010/0030038 A1 | 2/2010 | Brauker et al. | WO | WO-89/08713 | 9/1989 | |
| 2010/0030053 A1 | 2/2010 | Goode, Jr. et al. | WO | WO-90/00367 | 1/1990 | |
| 2010/0030484 A1 | 2/2010 | Brauker et al. | WO | WO-90/00738 | 1/1990 | |
| 2010/0030485 A1 | 2/2010 | Brauker et al. | WO | WO-90/05300 | 5/1990 | |
| 2010/0036215 A1 | 2/2010 | Goode, Jr. et al. | WO | WO-90/05910 | 5/1990 | |
| 2010/0036216 A1 | 2/2010 | Goode, Jr. et al. | WO | WO-90/10861 | 9/1990 | |
| 2010/0036222 A1 | 2/2010 | Goode, Jr. et al. | WO | WO-90/13021 | 11/1990 | |
| 2010/0036223 A1 | 2/2010 | Goode, Jr. et al. | WO | WO-91/01680 | 2/1991 | |
| 2010/0036225 A1 | 2/2010 | Goode, Jr. et al. | WO | WO-91/04704 | 4/1991 | |
| 2010/0041971 A1 | 2/2010 | Goode, Jr. et al. | WO | WO-91/15993 | 10/1991 | |
| 2010/0045465 A1 | 2/2010 | Brauker et al. | WO | WO-92/04153 | 3/1992 | |
| 2010/0049024 A1 | 2/2010 | Saint et al. | WO | WO-92/07525 | 5/1992 | |
| 2010/0063373 A1 | 3/2010 | Kamath et al. | WO | WO-92/10584 | 6/1992 | |
| 2010/0076283 A1 | 3/2010 | Simpson et al. | WO | WO-92/13271 | 8/1992 | |
| 2010/0081908 A1 | 4/2010 | Dobbles et al. | WO | WO-93/05703 | 4/1993 | |
| 2010/0081910 A1 | 4/2010 | Brister et al. | WO | WO-93/14693 | 8/1993 | |
| 2010/0087724 A1 | 4/2010 | Brauker et al. | WO | WO-93/19701 | 10/1993 | |
| 2010/0096259 A1 | 4/2010 | Zhang et al. | WO | WO-94/20602 | 9/1994 | |
| 2010/0099970 A1 | 4/2010 | Shults et al. | WO | WO-94/22367 | 10/1994 | |
| 2010/0099971 A1 | 4/2010 | Shults et al. | WO | WO-94/27140 | 11/1994 | |
| 2010/0119693 A1 | 5/2010 | Tapsak et al. | WO | WO-95/06240 | 3/1995 | |
| 2010/0121169 A1 | 5/2010 | Petisce et al. | WO | WO-95/07109 | 3/1995 | |
| | | | WO | WO-96/01611 | 1/1996 | |
| FOREIGN PATENT DOCUMENTS | | | WO | WO-96/07908 | 3/1996 | |
| EP | 0010375 | 4/1980 | WO | WO-96/14026 | 5/1996 | |
| EP | 0026995 | 4/1981 | WO | WO-96/25089 | 8/1996 | |
| EP | 0048090 | 3/1982 | WO | WO-96/30431 | 10/1996 | |
| EP | 0078636 | 5/1983 | WO | WO-96/32076 | 10/1996 | |
| EP | 0080304 | 6/1983 | WO | WO-96/35370 | 11/1996 | |
| EP | 0098592 | 1/1984 | WO | WO-96/36296 | 11/1996 | |
| EP | 0107634 | 5/1984 | WO | WO-97/01986 | 1/1997 | |
| EP | 0125139 | 11/1984 | WO | WO-97/02847 | 1/1997 | |
| EP | 0127958 | 12/1984 | WO | WO-97/06727 | 2/1997 | |
| EP | 0136362 | 4/1985 | WO | WO-97/19344 | 5/1997 | |
| EP | 0170375 | 2/1986 | WO | WO-97/20207 | 6/1997 | |
| EP | 0177743 | 4/1986 | WO | WO-97/28737 | 8/1997 | |
| EP | 0184909 | 6/1986 | WO | WO-97/41421 | 11/1997 | |
| EP | 0206218 | 12/1986 | WO | WO-97/42882 | 11/1997 | |
| EP | 0230472 | 8/1987 | WO | WO-97/42883 | 11/1997 | |
| EP | 0241309 | 10/1987 | WO | WO-97/42886 | 11/1997 | |
| EP | 0245073 | 11/1987 | WO | WO-97/42888 | 11/1997 | |
| EP | 0255291 | 2/1988 | WO | WO-97/43962 | 11/1997 | |
| EP | 0278647 | 8/1988 | WO | WO-97/46868 | 12/1997 | |
| EP | 0320109 | 6/1989 | WO | WO-98/09167 | 3/1998 | |
| EP | 0353328 | 2/1990 | WO | WO-98/10699 | 3/1998 | |
| EP | 0359831 | 3/1990 | WO | WO-98/24358 | 6/1998 | |
| EP | 0368209 | 5/1990 | WO | WO-98/24366 | 6/1998 | |
| EP | 0368290 | 5/1990 | WO | WO-98/35053 | 8/1998 | |
| EP | 0390390 | 10/1990 | WO | WO-98/52045 | 11/1998 | |
| EP | 0396788 | 11/1990 | WO | WO-98/52293 | 11/1998 | |
| EP | 0400918 | 12/1990 | WO | WO-98/56293 | 12/1998 | |
| EP | 0453283 | 10/1991 | WO | WO-99/05966 | 2/1999 | |
| EP | 0512122 | 11/1992 | WO | WO-99/13574 | 3/1999 | |
| EP | 0535898 | 4/1993 | WO | WO-99/32883 | 7/1999 | |
| EP | 0539625 | 5/1993 | WO | WO-99/48419 | 9/1999 | |

| | | |
|---|---|---|
| WO | WO-99/56613 | 11/1999 |
| WO | WO-99/58051 | 11/1999 |
| WO | WO-99/58973 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/32098 | 6/2000 |
| WO | WO-00/33065 | 6/2000 |
| WO | WO-00/49940 | 8/2000 |
| WO | WO-00/59370 | 10/2000 |
| WO | WO-00/59373 | 10/2000 |
| WO | WO-00/62664 | 10/2000 |
| WO | WO-00/62665 | 10/2000 |
| WO | WO-00/74753 | 12/2000 |
| WO | WO-00/78210 | 12/2000 |
| WO | WO-00/78992 | 12/2000 |
| WO | WO-01/12158 | 2/2001 |
| WO | WO-01/20019 | 3/2001 |
| WO | WO-01/20334 | 3/2001 |
| WO | WO-01/24038 | 4/2001 |
| WO | WO-01/33216 | 5/2001 |
| WO | WO-01/43660 | 6/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/58348 | 8/2001 |
| WO | WO-01/67009 | 9/2001 |
| WO | WO-01/68901 | 9/2001 |
| WO | WO-01/69222 | 9/2001 |
| WO | WO-01/88524 | 11/2001 |
| WO | WO-01/88534 | 11/2001 |
| WO | WO-02/16905 | 2/2002 |
| WO | WO-02/17210 | 2/2002 |
| WO | WO-02/24065 | 3/2002 |
| WO | WO-02/058537 | 8/2002 |
| WO | WO-02/078512 | 10/2002 |
| WO | WO-02/082989 | 10/2002 |
| WO | WO-02/100266 | 12/2002 |
| WO | WO-03/072269 | 9/2003 |
| WO | WO-03/076893 | 9/2003 |
| WO | WO-03/082091 | 10/2003 |
| WO | WO-03/085372 | 10/2003 |
| WO | WO-03/101862 | 12/2003 |
| WO | WO-2004/061420 | 7/2004 |
| WO | WO-2005/041766 | 5/2005 |
| WO | WO-2005/089103 | 9/2005 |
| WO | WO-2005/026689 | 10/2005 |
| WO | WO-2005/119524 | 12/2005 |
| WO | WO-2006/024671 | 3/2006 |
| WO | WO-2006/079114 | 7/2006 |
| WO | WO-2006/086423 | 8/2006 |
| WO | WO-2006/105146 | 10/2006 |
| WO | WO-2006/118947 | 11/2006 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/051139 | 5/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2009/029662 | 3/2009 |

OTHER PUBLICATIONS

Choleau et al Calibration of a subcutaneous amperometric glucose sensor implanted for 7 days in diabetic patients Part 2. Superiority of the one-point calibration method.*

Kovatchev et al, "Evaluating the Accuracy of Continuous Gklucose Sensors. Contnuous glucose error grid analysis illustrated byTherasense Freestyle Navigator," Diabetes Care 27, pp. 1922-1928, 2004.*

U.S. Appl. No. 11/759,923, McGarraugh, et al.

U.S. Appl. No. 11/759,926, McGarraugh, et al.

U.S. Appl. No. 11/759,925, McGarraugh, et al.

International Preliminary Report on Patentability and Written Opinion of the International Searching Authority for PCT Application No. PCT/US2007/013582 filed Jun. 7, 2007, mailed Dec. 24, 2008.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Search Report and Written Opinion of the International Searchign Authority for PCT Application No. PCT/US2007/013582 filed Jun. 7, 2007 to Abbott Diabetes Care, Inc. mailed Jul. 8, 2008.

U.S. Appl. No. 11/759,923, Office Action mailed Apr. 1, 2010.
U.S. Appl. No. 11/759,923, Office Action mailed Feb. 25, 2009.
U.S. Appl. No. 11/759,923, Office Action mailed Jun. 3, 2008.
U.S. Appl. No. 11/759,926, Office Action mailed Jun. 2, 2008.
U.S. Appl. No. 11/759,926, Office Action mailed Nov. 27, 2009.
U.S. Appl. No. 11/759,926, Office Action mailed Jun. 24, 2010.
U.S. Appl. No. 11/759,925, Advisory Action mailed Aug. 25, 2009.
U.S. Appl. No. 11/759,925, Office Action mailed Mar. 12, 2009.
U.S. Appl. No. 11/759,925, Office Action mailed May 30, 2008.
U.S. Appl. No. 11/759,925, Office Action mailed Sep. 23, 2009.
U.S. Appl. No. 11/759,925, Office Action mailed Jun. 24, 2010.
U.S. Appl. No. 12/506,217, Office Action mailed Mar. 1, 2010.

Abel, P. U., et al., "Biosensors for in Vivo Glucose Measurement: Can We Cross the Experimental Stage", *Biosensors and Bioelectronics*, vol. 17, 2002, pp. 1059-1070.

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Asberg, P., et al., "Hydrogels of a Conducting Conjugated Polymer as 3-D Enzyme Electrode", *Biosensors & Bioelectronics*, vol. 19, 2003, pp. 199-207.

Atanasov, P., et al., "Biosensor for Continuous Glucose Monitoring", *Biotechnology and Bioengineering*, vol. 43, 1994, pp. 262-266.

Atanasov, P., et al., "Implantation of a Refillable Glucose Monitoring-Telemetry Device", *Biosensors & Bioelectronics*, vol. 12, No. 7, 1997, pp. 669-680.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp.1061-1071.

Baker, D. A., et al., "Dynamic Concentration Challenges for Biosensor Characterization", *Biosensors & Bioelectronics*, vol. 8, 1993, pp. 433-441.

Baker, D. A., et al., "Dynamic Delay and Maximal Dynamic Error in Continuous Biosensors", *Analytical Chemistry*, vol. 68, No. 8, 1996, pp. 1292-1297.

Bani Amer, M. M., "An Accurate Amperometric Glucose Sensor Based Glucometer with Eliminated Cross-Sensitivity", *Journal of Medical Engineering & Technology*, vol. 26, No. 5, 2002, pp. 208-213.

Bard, A. J., et al., *Electrochemical Methods*, 1980, pp. 173-175.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Beach, R. D., et al., "Subminiature Implantable Potentiostat and Modified Commercial Telemetry Device for Remote Glucose Monitoring", *IEEE Transactions on Instrumentation and Measurement*, vol. 28, No. 6, 1999, pp. 1239-1245.

Beech, W. A., "AX.25 Link Access Protocol for Amateur packet Radio", *Tucson Amateur Packet Radio Corporation*, 1998, pp. 1-133.

Bellucci, F., et al., "Electrochemical Behaviour of Graphite-Epoxy Composite Materials (GECM) in Aqueous Salt Solutions", *Journal of Applied Electrochemistry*, vol. 16, 1986, pp. 15-22.

Biermann, E., et al., "How Would Patients Behave if They Were Continually Informed of Their Blood Glucose Levels? A Simulation Study Using a 'Virtual' Patient", *Diabetes Technology & Therapeutics*, vol. 10, No. 3, 2008, pp. 178-187.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Bindra, D. S., et al., "Pulsed Amperometric Detection of Glucose in Biological Fluids at a Surface-Modified Gold Electrode", *Analytical Chemistry*, vol. 61, No. 22, 1989, pp. 2566-2570.

Bisenberger, M., et al., "A Triple-Step Potential Waveform at Enzyme Multisensors with Thick-Film Gold Electrodes for Detection of Glucose and Sucrose", *Sensors and Actuators B*, vol. 28, 1995, pp. 181-189.

Bland, J. M., et al., "A Note on the Use of the Intraclass Correlation Coefficient in the Evaluation of Agreement Between Two Methods of Measurement", *Computers in Biology and Medicine*, vol. 20, No. 5, 1990, pp. 337-340.

Bland, J. M., et al., "Statistical Methods for Assessing Agreement Between Two Methods of Clinical Measurement", *The Lancet*, 1986, pp. 307-310.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Bode, B. W., "Clinical Utility of the Continuous Glucose Monitoring System", *Diabetes Technology & Therapeutics*, vol. 2, Sup. 1, 2000, pp. S35-S41.

Bode, B. W., et al., "Continuous Glucose Monitoring Used to Adjust Diabetes Therapy Improves Glycosylated Hemoglobin: A Pilot Study", *Diabetes Research and Clinical Practice*, vol. 46, 1999, pp. 183-190.

Bode, B. W., et al., "Using the Continuous Glucose Monitoring System to Improve the Management of Type I Diabetes", *Diabetes Technology & Therapeutics*, vol. 2, Sup. 1, 2000, pp. S43-S48.

Boedeker Plastics, Inc., "Polyethylene Specifications", Web Page of Boedeker.com, 2007, pp. 1-3.

Bolinder, J., et al., "Microdialysis Measurement of the Absolute Glucose Concentration in Subcutaneous Adipose Tissue Allowing Glucose Monitoring in Diabetic Patients", *Diabetologia*, vol. 35, 1992, pp. 1177-1180.

Bolinder, J., et al., "Self-Monitoring of Blood Glucose in Type I Diabetic Patients: Comparison with Continuous Microdialysis Measurements of Glucose in Subcutaneous Adipose Tissue During Ordinary Life Conditions", *Diabetes Care*, vol. 20, No. 1, 1997, pp. 64-70.

Bott, A. W., "A Comparison of Cyclic Voltammetry and Cyclic Staircase Voltammetry", *Current Separations*, vol. 16, No. 1, 1997, pp. 23-26.

Bott, A. W., "Electrochemical Methods for the Determination of Glucose", *Current Separations*, vol. 17, No. 1, 1998, pp. 25-31.

Bowman, L., et al., "The Packaging of Implantable Integrated Sensors", *IEEE Transactions on Biomedical Engineering*, vol. 33, No. 2, 1986, pp. 248-255.

Brandt, J., et al., "Covalent Attachment of Proteins to Polysaccharide Carriers by Means of Benzoquinone", *Biochimica et Biophysica Acta*, vol. 386, 1975, pp. 196-202.

Brauker, J., et al., "Sustained Expression of High Levels of Human Factor IX from Human Cells Implanted Within an Immunoisolation Device into Athymic Rodents", *Human Gene Therapy*, vol. 9, No. 6, 1998, pp. 879-888.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Bremer, T., et al., "Is Blood Glucose Predictable from Previous Values?", *Diabetes*, vol. 48, 1999, pp. 445-451.

Brownlee, M., et al., "A Glucose-Controlled Insulin-Delivery System: Semisynthetic Insulin Bound to Lectin", *Science*, vol. 206, 1979, 1190-1191.

Cai, Q., et al., "A Wireless, Remove Query Glucose Biosensor Based on a pH-Sensitive Polymer", *Analytical Chemistry*, vol. 76, No. 14, 2004, pp. 4038-4043.

Candas, B., et al., "An Adaptive Plasma Glucose Controller Based on a Nonlinear Insulin/Glucose Model", *IEEE Transactions on Biomedical Engineering*, vol. 41, No. 2, 1994, pp. 116-124.

Cass, A. E., et al., "Ferricinum Ion As An Electron Acceptor for Oxido-Reductases", *Journal of ElectroAnalytical Chemistry*, vol. 190, 1985, pp. 117-127.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Chen, J. C., et al., "A Comparison of MAC Protocols for Wireless Local Networks Based on battery Power Consumption", *IEEE*, 1998, pp. 150-157.

Chen, T., et al., "Defining the Period of Recovery of the Glucose Concentration After Its Local Perturbation by the Implantation of a Miniature Sensor", *Clinical Chemistry and Laboratory Medicine*, vol. 40, No. 8, 2002, pp. 486-469.

Chia, C. W., et al., "Glucose Sensors: Toward Closed Loop Insulin Delivery", *Endocrinology and Metabolism Clinics of North America*, vol. 33, 2004, pp. 175-195.

Choleau, C., et al., "Calibration of a Subcutaneous Amperometric Glucose Sensor Part 1: Effect of Measurement Uncertainties on the Determination of Sensor Sensitivity and Background Current", *Biosensors and Bioelectronics*, vol. 17, 2002, pp. 641-646.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Cox, D. J., et al., "Accuracy of Perceiving Blood Glucose in IDDM", *Diabetes Care*, vol. 8, No. 6, 1985, pp. 529-536.

Csoregi, E., et al., "Amperometric Microbiosensors for Detection of Hydrogen Peroxide and Glucose Based on Peroxidase-Modified Carbon Fibers", *Electroanalysis*, vol. 6, 1994, pp. 925-933.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

D'Arrigo, G., et al., "Porous-Si Based Bio Reactors for Glucose Monitoring and Drugs Production", *Proceedings of SPIE: Microfluids, BioMEMS, and Medical Microsystems*, vol. 4982, 2003, pp. 178-184.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davies, M. L., et al., "Polymer Membranes in Clinical Sensor Applications", *Biomaterials*, vol. 13 No. 14, 1992, pp. 971-978.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Dixon, B. M., et al., "Characterization In Vitro and In Vivo of the Oxygen Dependence of an Enzyme/Polymer Biosensors for Monitoring Brain Glucose", *Journal of Neuroscience Methods*, vol. 119, 2002, pp. 135-142.

*Eighth Annual Diabetes Technology Meeting Abstracts*, Nov. 13-15, 2008, pp. A1-A182.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Ellis, C. D., et al., "Selectivity and Directed Charge Transfer through an Electroactive Metallopolymer Film", *Journal of the American Chemical Society*, vol. 103, No. 25, 1981, pp. 7480-7483.

El-Sa'Ad, L., et al., "Moisture Absorption by Epoxy Resins: The Reverse Thermal Effect", *Journal of Materials Science*, vol. 25, No. 8, 1990, pp. 3577-3582.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Ernst, H., et al., "Reliable Glucose Monitoring Through the Use of Microsystem Technology", *Analytical and Bioanalytical Chemistry*, vol. 373, 2002, pp. 758-761.

Fabietti, P. G., et al. "Clinical Validation of a New Control-Oriented Model of Insulin and Glucose Dynamics in Subjects with Type 1 Diabetes", *Diabetes Technology & Therapeutics*, vol. 9 No. 4, 2007, pp. 327-338.

Fare, T. L., et al., "Functional Characterization of a Conducting Polymer-Based Immunoassay System", *Biosensors & Bioelectronics*, vol. 13, No. 3-4, 1998, pp. 459-470.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al , "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Frohnauer, M. K., et al., "Graphical Human Insulin Time-Activity Profiles Using Standardized Definitions", *Diabetes Technology & Therapeutics*, vol. 3, No. 3, 2001, pp. 419-429.

Frost, M. C., et al., "Implantable Chemical Sensors for Real-Time Clinical Monitoring: Progress and Challenges", *Current Opinion in Chemical Biology*, vol. 6, 2002, pp. 633-641.

Garg, S. K., et al., "Correlation of Fingerstick Blood Glucose Measurements with GlucoWatch Biographer Glucose Results in Young Subjects with Type 1 Diabetes", *Diabetes Care*, vol. 22, No. 10, 1999, pp. 1708-1714.

Garg, S. K., et al., "Improved Glucose Excursions Using an Implantable Real-Time Continuous Glucose Sensor in Adults with Type 1 Diabetes", *Diabetes Care*, vol. 27, No. 3, 2004, pp. 734-738.

Geller, R. L., et al., "Use of an Immunoisolation Device for Cell Transplantation and Tumor Immunotherapy", *Annals of the New York Academy of Sciences*, vol. 831, 1997, pp. 438-451.

Gerritsen, M., "Problems Associated with Subcutaneously Implanted Glucose Sensors",. *Diabetes Care*, vol. 23, No. 2, 2000, pp. 143-145.

Gerritsen, M., et al., "Influence of Inflammatory Cells and Serum on the Performance of Implantable Glucose Sensors", *Journal of Biomedical materials Research*, vol. 54, 2001, pp. 69-75.

Gerritsen, M., et al., "Performance of Subcutaneously Implanted glucose Sensors for Continuous Monitoring", *The Netherlands Journal of Medicine*, vol. 54, 1999, pp. 167-179.

Gilligan, B. J., et al., "Evaluation of a Subcutaneous Glucose Sensor Out to 3 Months in a Dog Model", *Diabetes Care*, vol. 17, No. 8, 1994, pp. 882-887.

Gilligan, B. J., et al., "Feasibility of Continuous Long-Term Glucose Monitoring from a Subcutaneous Glucose Sensor in Humans", *Diabetes Technology & Therapeutics*, vol. 6, No. 3, 2004, pp. 378-386.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Gough, D. A., et al , "Immobilized Glucose Oxidase in Implantable Glucose Sensor Technology", *Diabetes Technology & Therapeutics*, vol. 2, No. 3, 2000, pp. 377-380.

Graham, N. B., "Poly(ethylene oxide) and Related Hydrogels," *Hydrogels in Medicine and Pharmacy, vol. II: Polymers*, Chapter 4, 1987, pp. 95-113.

Grant, R., et al., *Grant & Hackh's Chemical Dictionary*, 1987, pp. 88, 89, 389, 390, 398.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Gross, T. M., et al., "Efficacy and Reliability of the Continuous Glucose Monitoring System", *Diabetes Technology & Therapeutics*, vol. 2, Sup. 1, 2000, pp. S19-S26.

Gross, T. M., et al., "Performance Evaluation of the MiniMed® Continuous Glucose Monitoring System During Patient Home Use", *Diabetes Technology & Therapeutics*, vol. 2, No. 1, 2000, pp. 49-56.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Hall, S. B., et al., "Electrochemical Oxidation of Hydrogen Peroxide at Platinum Electrodes: Part I: An Absorption-Controlled Mechanism", *Electrochimica Acta*, vol. 43, No. 5-6, 1998, pp. 579-588.

Hall, S. B., et al., "Electrochemical Oxidation of Hydrogen Peroxide at Platinum Electrodes: Part II: Effect of Potential", *Electrochimica Acta*, vol. 43, No. 14-15, 1998, pp. 2015-2024.

Hall, S. B., et al., "Electrochemical Oxidation of Hydrogen Peroxide at Platinum Electrodes: Part III: Effect of Temperature", *Electrochimica Acta*, vol. 44, 1999, pp. 2455-2462.

Hall, S. B., et al., "Electrochemical Oxidation of Hydrogen Peroxide at Platinum Electrodes: Part IV: Phosphate Buffer Dependence", *Electrochimica Acta*, vol. 44, 1999, pp. 4573-4582.

Hall, S. B., et al., "Electrochemical Oxidation of Hydrogen Peroxide at Platinum Electrodes: Part V: Inhibition by Chloride", Electrochimica Acta, Vol. 45, 2000, pp. 3573-3579.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heise, T., et al., "Hypoglycemia Warning Signal and Glucose Sensors: Requirements and Concepts", *Diabetes Technology & Therapeutics*, vol. 5, No. 4, 2003, pp. 563-571.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., "Implanted Electrochemical Glucose Sensors for the Management of Diabetes", *Annual Review of Biomedical Engineering*, vol. 1, 1999, pp. 153-175.

Heller, A., "Plugging Metal Connectors into Enzymes", *Nature Biotechnology*, vol. 21, No. 6, 2003, pp. 631-632.

Heller, A., et al., "Amperometric Biosensors Based on Three-Dimensional Hydrogel-Forming Epoxy Networks", *Sensors and Actuators B*, vol. 13-14, 1993, pp. 180-183.

Hicks, J. M., "In Situ Monitoring", *Clinical Chemistry*, vol. 31, No. 12, 1985, pp. 1931-1935.

Hitchman, M. L., "Measurement of Dissolved Oxygen: Chapter 3: Principles of Voltammetry", *Chemical Analysis*, vol. 49, 1978, pp. 34-123.

Hrapovic, S., et al., "Picoamperometric Detection of Glucose at Ultrasmall Platinum-Based Biosensors: Preparation and Characterization", *Analytical Chemistry*, vol. 75, No. 14, 2003, pp. 3308-3315.

Hu, Y., et al., "A Needle-Type Enzyme-Based Lactate Sensor for In Vivo Monitoring", *Analytica Chimica Acta*, vol. 281, 1993, pp. 503-511.

Huang, C. J., et al., "Electrochemical Generation of Oxygen", *Electrochemistry Research laboratory*, 1972, pp. 1-115.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Ishikawa, M., et al., "Initial Evaluation of a 290-μm Diameter Subcutaneous Glucose Sensor: Glucose Monitoring with a Biocompatible, Flexible-Wire, Enzyme-Based Amperometric Microsensor in Diabetic and Nondiabetic Humans", *Journal of Diabetes and Its Complications*, vol. 12, 1998, pp. 295-301.

Jablecki, M., et al., "Simulations of the Frequency Response of Implantable Glucose Sensors", *Analytical Chemistry*, vol. 72, No. 8, 2000, pp. 1853-1859.

Jaremko, J., et al., "Advances Toward the Implantable Artificial Pancreas for Treatment of Diabetes", *Diabetes Care*, vol. 21, No. 3, 1998, pp. 444-450.

Jensen, M. B., et al., "Fast Wave Forms for Pulsed Electrochemical Detection of Glucose by Incorporation of Reductive Desorption of Oxidation Products", *Analytical Chemistry*, vol. 69, No. 9, 1997, pp. 1776-1781.

Jeutter, D. C., "A Transcutaneous Implanted Battery Recharging and Biotelemeter Power Switching System", *IEEE Transactions on Biomedical Engineering*, vol. 29, No. 5, 1982, pp. 314-321.

Jobst, G., et al., "Thin-Film Microbiosensors for Glucose-Lactate Monitoring", *Analytical Chemistry*, vol. 68, No. 18, 1996, pp. 3173-3179.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jovanovic, L., "The Role of Continuous Glucose Monitoring in Gestational Diabetes Mellitus", *Diabetes Technology & Therapeutics*, vol. 2, Sup. 1, 2000, pp. S67-S71.

Kamath, A., et al., "Calibration of a Continuous Glucose Monitor: Effect of Glucose Rate of Change", *Eighth Annual Diabetes Technology Meeting Abstracts*, Nov. 13-15, 2008, pp. A88.

Kang, S. K., et al., "In Vitro and Short-Term In Vivo Characteristics of a Kel-F Thin Film Modified Glucose Sensor", *Analytical Sciences*, vol. 19, 2003, pp. 1481-1486.

Kargol, M., et al., "Studies on the Structural Properties of Porous Membranes: Measurement of Linear Dimensions of Solutes", *Biophysical Chemistry*, vol. 91, 2001, pp. 263-271.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kaufman, F. R., "Role of the Continuous Glucose Monitoring System in Pediatric Patients", *Diabetes Technology & Therapeutics*, vol. 2, Sup. 1, 2000, pp. S49-S52.

Kawagoe, J. L., et al., "Enzyme-Modified Organic Conducting Salt Microelectrode", *Analytical Chemistry*, vol. 63, No. 24, 1991, pp. 2961-2965.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)$_2$Cl]$^{+/2+}$", *Journal of the Chemical Society, Faraday Transactions*, vol. 92, No. 20, 1996, pp. 4131-4136.

Kerner, W., "Implantable Glucose Sensors: Present Status and Future Developments", *Experimental and Clinical Endocrinology & Diabetes*, vol. 109, Supplement 2, 2001, pp. S341-S346.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koschinsky, T., et al., "New Approach to Technical and Clinical Evaluation of Devices for Self-Monitoring of Blood Glucose", *Diabetes Care*, vol. 11, No. 9, 1988, pp. 619-629.

Koschinsky, T., et al., "Sensors for Glucose Monitoring: Technical and Clinical Aspects" *Diabetes Metabolism Research and Reviews*, vol. 17, 2001, pp. 113-123.

Koudelka, M., et al., "In-Vivo Behaviour of Hypodermically Implanted Microfabricated Glucose Sensors", *Biosensors & Bioelectronics*, vol. 6, 1991, pp. 31-36.

Kraver, K. L., et al., "A Mixed-Signal Sensor Interface Microinstrument", *Sensors and Actuators A*, vol. 91, 2001, pp. 266-277.

Krouwer, J. S., "Setting Performance Goals and Evaluating Total Analytical error for Diagnostic Assays", *Clinical Chemistry*, vol. 48, No. 6, 2002, pp. 919-927.

Kruger, D., et al., "Psychological Motivation and Patient Education: A Role for Continuous Glucose Monitoring", *Diabetes Technology & Therapeutics*, vol. 2, Sup. 1, 2000, pp. S93-S97.

Kulys, J., et al., "Mediatorless Peroxidase Electrode and Preparation of Bienzyme Sensors", *Bioelectrochemistry and Bioenergetics*, vol. 24, 1990, pp. 305-311.

Kurnik, R. T., et al., "Application of the Mixtures of Experts Algorithm for Signal Processing in a Noninvasive Glucose Monitoring System" *Sensors and Actuators B*, vol. 60, 1990, pp. 19-26.

Kusano, H., "Glucose Enzyme Electrode with Percutaneous Interface Which Operates Independently of Dissolved Oxygen", *Clinical Physics and Physiological Measurement*, vol. 10, No. 1, 1989, pp. 1-9.

Lacourse, W. R., et al., "Optimization of Waveforms for Pulsed Amperometric Detection of Carbohydrates Based on Pulsed Voltammetry", *Analytical Chemistry*, vol. 65, No. 1, 1993, pp. 50-55.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lee, E., et al., "Effects of Pore Size, Void Volume, and Pore Connectivity on Tissue Responses to Porous Silicone Implants", *Transactions on the Twenty-Fifth Annual Meeting of the Society for Biomaterials*, vol. 22, 1999, pp. 171.

Lerner, H., et al., "An Implantable Electrochemical Glucose Sensor", *Annals of the New York Academy of Sciences*, vol. 428, 1984, pp. 263-278.

Lewis, R. J., ed., "2-hydroxyethyl methacrylate", *Hawley's Condensed Chemical Dictionary, Twelfth Edition*, 1993, pp. 596.

Leypoldt, J. K., et al., "Model of a Two-Substrate Enzyme Electrode for Glucose", *Analytical Chemistry*, vol. 56, No. 14, 1984, pp. 2896-2904.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Liu, W., et al., "A Neuro-Stimulus Chip with Telemetry Unit for Retinal Prosthetic Device", *IEEE Journal of Solid-State Circuits*, vol. 35, No. 10, 2000, pp. 1487-1497.

Lohn, A., et al., "A Knowledge-Based System for Real-Time Validation of Calibrations and Measurements", *Chemometrics and Intelligent Laboratory Systems*, vol. 46, 1999, pp. 57-66.

Luong, J. H. T., et al., "Solubilization of Multiwall Carbon Nanotubes by 3-Aminopropyltriethoxysilane Towards the Fabrication of Electrochemical Biosensors with Promoted Electron Transfer". *Electroanalysis*, vol. 16, No. 1-2, 2004, pp. 132-139.

Lynch, S. M., et al., "Estimation-Based Model Predictive Control of Blood Glucose in Type I Diabetics: A Simulation Study", *Proceedings of the IEEE 27th Annual Northeast Bioengineering Conference*, 2001, pp. 79-80.

Lynn, P. A., "Recursive Digital Filters for Biological Signals", *Medical and Biological Engineering*, vol. 9, 1971, pp. 37-43.

Maidan, R., et al., "Elimination of Electrooxidizable Interferant-Produced Currents in Amperometric Biosensors", *Analytical Chemistry*, vol. 64, No. 23, 1992, pp. 2889-2896.

Makale, M. T., et al., "Tissue Window Chamber System for Validation of Implanted Oxygen Sensors", *American Journal of Physiology: Heart and Circulatory Physiology*, vol. 284, 2003, pp. H2288-H2294.

Mancy, K. H., et al., "A Galvanic Cell Oxygen Analyzer", *Journal of Electroanalytical Chemistry*, vol. 4, 1962, pp. 65-92.

Maran, A., et al., "Continuous Glucose Monitoring in Diabetic Patients", *Diabetes Care*, vol. 25 No. 2, 2002, pp. 347-352.

March, W. F., "Dealing with the Delay", *Diabetes Technology & Therapeutics*, vol. 4, No. 1, 2002, pp. 49-50.

Marko-Varga, G., et al., "Enzyme-Based Biosensor as a Selective Detection Unit in Column Liquid Chromatography", *Journal of Chromatography A*, vol. 660, 1994, pp. 153-167.

Martin, R. F., "General Deming Regression for Estimating Systematic Bias and Its Confidence Interval in Method-Comparison Studies", *Clinical Chemistry*, vol. 46, No. 1, 2000, pp. 100-104.

Mastrotaro, J.J., "The MiniMed Continuous Glucose Monitoring System", *Diabetes Technology & Therapeutics*, vol 2, Sup. 1, 2000, pp. S13-S18.

Mastrototaro, J. J., et al., "An Electroenzymatic Glucose Sensor Fabricated on a Flexible Substrate", *Sensors and Actuators B*, vol. 5, 1991, pp. 139-144.

Mastrototaro, J. J., et al., "Reproducibility of the Continuous Glucose Monitoring System Matches Previous Reports and the Intended Use of the Product" and "Response to Mastrototaro and Gross", *Diabetes Care*, vol. 26, No. 1, 2003, pp. 256-257.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

Mazze, R. S., et al., "Characterizing Glucose Exposure for Individuals with Normal Glucose Tolerance Using Continuous Glucose Monitoring and Ambulatory Glucose Profile Analysis", *Diabetes Technology & Therapeutics*, vol. 10, No. 3, 2008, pp. 149-159.

McCartney, L. J., et al., "Near-Infrared Fluorescence Lifetime Assay for Serum Glucose Based on Allophycocyanin-Labeled Concanavalin A", *Analytical Biochemistry*, vol. 292, 2001, pp. 216-221.

McGarraugh, G., et al., "Glucose Measurements Using Blood Extracted from the Forearm and the Finger", *TheraSense, Inc.*, 16 Pages.

McGrath, M. J., et al., "The Use of Differential Measurements with a Glucose Biosensor for Interference Compensation During Glucose Determinations by Flow Injection Analysis", *Biosensors & Bioelectronics*, vol. 10, 1995, pp. 937-943.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Memoli, A., et al., "A Comparison Between Different Immobilized Glucoseoxidase-Based Electrodes", *Journal of Pharmaceutical and Biomedical Analysis*, vol. 29, 2002, pp. 1045-1052.

Metzger, M., et al., "Reproducibility of Glucose Measurements Using the Glucose Sensor", *Diabetes Care*, vol. 25, No. 6, 2002, pp. 1185-1191.

Miller, K. M., et al., "Generation of IL1-like Activity in Response to Biomedical Polymer Implants: A Comparison of In Vitro and In Vivo Models", *Journal of Biomedical Materials Research*, vol. 23, 1989, pp. 1007-1026.

Miller, K. M., et al., "Human Monocyte/Macrophage Activation and Interleukin 1 Generation by Biomedical Polymers", *Journal of Biomedical Materials Research*, vol. 22, 1988, pp. 713-731.

Miller, K. M., et al., "In Vitro Stimulation of Fibroblast Activity by Factors Generated from Human Monocytes Activated by Biomedical Polymers", *Journal of Biomedical Materials Research*, vol. 23, 1989, pp. 911-930.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1997, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-230.

Monsod, T. P., et al., "Do Sensor Glucose Levels Accurately Predict Plasma Glucose Concentrations During Hypoglycemia and Hyperinsulinemia?" *Diabetes Care*, vol. 25, No. 5, 2002, pp. 889-893.

Moussy, F., et al., "A Miniaturized Nation-Based Glucose Sensor: In Vitro and In Vivo Evaluation in Dogs", *The International Journal of Artificial Organs*, vol. 17, No. 2, 1994, pp. 88-94.

Mowery, K. A., et al., "Preparation and Characterization of Hydrophobic Polymeric Films that are Thromboresistant via Nitric Oxide Release", *Biomaterials*, vol. 21, 2000, pp. 9-21.

Murphy, S. M., et al., "Polymer Membranes in Clinical Sensor Applications", *Biomaterials*, vol. 13, No. 14, 1992, pp. 979-990.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Nam, Y. S., et al., "A Novel Fabrication Method of Macroporous Biodegradable Polymer Scaffolds Using Gas Foaming Salt as a Porogen Additive", *Journal of Biomedical Materials Research*, vol. 53, 2000, pp. 1-7.

Nappholz, T. A., "Programmers for Implants: A Need for Radical Change", 18th *Annual International Conference of the IEEE Engineering in Medicine and Biology Society, Amsterdam*, 1996, pp. 1274-1275.

Narasimham, K., et al., "p-Benzoquinone Activation of Metal Oxide Electrodes for Attachment of Enzymes", *Enzyme and Microbial Technology*, vol. 7, 1985, pp. 283-286.

Neuburger, G. G., et al., "Pulsed Amperometric Detection of Carbohydrates at Gold Electrodes with a Two-Step Potential Waveform", *Analytical Chemistry*, vol. 59, No. 1, 1987, pp. 150-154.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determinatiion of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Okuda, J., et al., "Mutarotase Effect on Micro Determinations of D-Glucose and Its Anomers with β-D-Glucose Oxidase", *Analytical Biochemistry*, vol. 43, 1971, pp. 312-315.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Palmisano, F., et al., "Simultaneous Monitoring of Glucose and Lactate by an Interference and Cross-Talk Free Dual Electrode Amperometric Biosensor Based on Electropolymerized Thin Films", *Biosensors & Bioelectronics*, vol. 15, 2000, pp. 531-539.

Pankratov, I., et al., "Sol-Gel Derived Renewable-Surface Biosensors", *Journal of ElectroAnalytical Chemistry*, vol. 393, 1995, pp. 35-41.

Panteleon, A. E., et al., "The Role of the Independent Variable to Glucose Sensor Calibration", *Diabetes Technology & Therapeutics*, vol. 5, No. 3, 2003, pp. 401-410.

Parker, R. S., et al., "A Model-Based Algorithm for Blood Glucose Control in Type I Diabetic Patients", *IEEE Transactions on Biomedical Engineering*, vol. 46, No. 2, 1999, pp. 148-157.

Patel, H., et al., "Amperometric Glucose Sensors Based on Ferrocene Containing Polymeric Electron Transfer Systems—A Preliminary Report", *Biosensors and Bioelectronics*, vol. 18, 2003, pp. 1073-1076.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Petrou, P. S., et al., "Microdevice with Integrated Dialysis Probe and Biosensor Array for Continuous Multi-Analyte Monitoring", *Biosensors & Bioelectronics*, vol. 18, 2003, pp. 613-619.

Pichert, J. W., et al., "Issues for the Coming Age of Continuous Glucose Monitoring", *The Diabetic Educator*, vol. 26, No. 6, 2000, pp. 969-980.

Pickup, J. C., et al., "Responses and Calibration of Amperometric Glucose Sensors Implanted in the Subcutaneous Tissue of Man", *Acta Diabetologica*, vol. 30, 1993, pp. 143-148.

Pickup, J., "Developing Glucose Sensors for In Vivo Use", *Tibtech*, vol. 11, 1993, pp. 285-291.

Pickup, J., et al., "Potentially-Implantable, Amperometric Glucose Sensors with Mediated Electron Transfer: Improving the Operating Stability", *Biosensors*, vol. 4, 1989, pp. 109-119.

Pitzer, K. R., et al., "Detection of Hypoglycemia with the GlucoWatch Biographer", *Diabetes Care*, vol. 24, No. 5, 2001, pp. 881-885.

Poirier, J. Y., et al., "Clinical and Statistical Evaluation of Self-Monitoring Blood Glucose Meters", *Diabetes Care*, vol. 21, No. 11, 1998, pp. 1919-1924.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Poscia, A., et al., "A Microdialysis Technique for Continuous Subcutaneous Glucose Monitoring in Diabetic Patients (Part 1)", *Biosensors & Bioelectronics*, vol. 18, 2003, pp. 891-898.

Postlethwaite, T. A., et al., "Interdigitated Array Electrode as an Alternative to the Rotated Ring—Disk Electrode for Determination of the Reaction Products of Dioxygen Reduction", *Analytical Chemistry*, vol. 68, No. 17, 1996, pp. 2951-2958.

Prabhu, V. G., et al., "Electrochemical Studies of Hydrogen Peroxide at a Platinum Disc Electrode", *Electrochimica Acta*, vol. 26, No. 6, 1981, pp. 725-729.

Quinn, C. A. P., et al., "Biocompatible, Glucose-Permeable Hydrogel for In Situ Coating of Implantable Biosensors", *Biomaterials*, vol. 18, No. 24, 1997, pp. 1665-1670.

Ratner, B. D., "Reducing Capsular Thickness and Enhancing Angeiogenesis Around Implant Drug Release Systems", *Journal of Controlled Release*, vol. 78, 2002, pp. 211-218.

Reach, G., "Which Threshold to Detect Hypoglycemia?", *Diabetes Care*, vol. 24, No. 5, 2001, pp. 803-804.

Reach, G., et al., "A Method of Evaluating In Vivo the Functional Characteristics of Glucose Sensors", *Biosensors 2*, 1986, pp. 211-220.

Reach, G., et al., "Can Continuous Glucose Monitoring Be Used for the Treatment of Diabetes?", *Analytical Chemistry*, vol. 64, No. 6, 1992, pp. 381-386.

Reach, G., et al., "Letters to the Editor: Re: Diabetes Technology & Therapeutics, 2000; 2:49-56", *Diabetes Technology & Therapeutics*, vol. 3, No. 1, 2001, pp. 129-131.

Rebrin, K., et al., "Automated Feedback Control of Subcutaneous Glucose Concentration in Diabetic Dogs", *Diabetologia*, vol. 32, 1989, pp. 573-576.

Rebrin, K., et al., "Subcutaneous Glucose Predicts Plasma Glucode Independent of Insulin: Implications for Continuous Monitoring", *The American Physiological Society*, 1999, pp. E561-E571.

Reusch, W., "Other Topics: Group Organometallic Chemistry: Organometallic Compounds: Main Group Organometallic Compounds," *Virtual Textbook of Organic Chemistry*, 1999, Rev. 2007, 25 pages.

Rhodes, R. K., et al., "Prediction of Pocket-Portable and Implantable Glucose Enzyme Electrode Performance from Combined Species Permeability and Digital Simulation Analysis", *Analytical Chemistry*, vol. 66, No. 9, 1994, pp. 1520-1529.

Rigla, M, et al., "Real-Time Continuous Glucose Monitoring Together with Telemedical Assistance Improves Glycemic Control and Glucose Stability in Pump-Treated Patients", *Diabetes Technology & Therapeutics*, vol. 10, No. 3, 2008, pp. 194-199.

Rinken, T., et al., "Calibration of Glucose Biosensors By Using Pre-Study State Kinetic Data", *Biosensors & Bioelectronics*, vol. 13, 1998, pp. 801-807.

Sacks (Ed), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Samuels, G. J., et al., "An Electrode-Supported Oxidation Catalyst Based on Ruthenium (IV). pH 'Encapsulation' in a Polymer Film", *Journal of the American Chemistry Society*, vol. 103, No. 2, 1981, pp. 307-312.

Sansen, W., et al., "A Smart Sensor for the Voltammetric Measurement of Oxygen or Glucose Concentrations", *Sensors and Actuators B1*, 1990, pp. 298-302.

Sansen, W., et al., "Chapter 12: Glucose Sensor with Telemetry System", *Implantable Sensors for Closed-Loop Prosthetic Systems*, 1985, pp. 167-175.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidt, F. J., et al., "Glucose Concentration in Subcutaneous Extracellular Space", *Diabetes Care*, vol. 16, No. 5, 1996, pp. 695-700.

Schmidtke, D. W., et al., "Accuracy of the One-Point In Vivo Calibration of 'Wired' Glucose Oxidase Electrodes Implanted in Jugular Veins of Rats in Periods of Rapid Rise and Decline of the Glucose Concentration", *Analytical Chemistry*, vol. 70, No. 10, 1998, pp. 2149-2155.

Schoemaker, M., et al., "The SCHM1 System: Subcutaneous Continuous Glucose Montoring Based on Microdialysis Technique", *Diabetes Technology & Therapeutics*, vol. 5, No. 4, 2003, pp. 599-608.

Schwarz, M., et al., "Micro Implantable Visual Prostheses", $1^{st}$ *Annual International IEEE EMBS Special Topic Conference on Microtechnologies in Medicine & Biology, Lyon, France*, 2000, pp. 461-465.

Selam, J. L., "Management of Diabetes with Glucose Sensors and Implantable Insulin Pumps: From the Dream of the 60s to the Realities of the 90s", *American Society for Artificial Internal Organs Journal*, 1997, pp. 137-142.

Service, F. J., et al., "Mean Amplitude of Glycemic Excursions, a Measure of Diabetic Instability", *Diabetes*, vol. 19, No. 9, 1970, pp. 644-655.

Service, R. F., "Can Sensors Make a Home in the Body?", *Science*, vol. 297, 2002, pp. 962-963.

Sieminski, A. L., et al., "Biomaterial-Microvasculature Interactions", *Biomaterials*, vol. 21, 2000, pp. 2233-2241.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Skyler, J. S., "The Economic Burden of Diabetes and the Benefits of Improved Glycemic Control: The Potential Role of a Continuous Glucose Monitoring Systems", *Diabetes Technology & Therapeutics*, vol. 2, Sup. 1, 2000, pp. S7-S12.

Soegijoko, S., et al., "External Artificial Pancreas: A New Control Unit Using Microprocessor", *Hormone and Metabolic Research Supplement Series*, vol. 12, 1982, pp. 165-169.

Sokol, L., et al , "Immobilized-Enzyme Rate-Determination Method for Glucose Analysis", *Clinical Chemistry*, vol. 26, No. 1, 1980, pp. 89-92.

Sokolov, S., et al., "Metrological Opportunities of the Dynamic Mode of Operating an Enzyme Amperometric Biosensor", *Medical Engineering and Physics*, vol. 17, No. 6, 1995, pp. 471-476.

Sproule, B. A., et al., "Fuzzy Pharmacology: Theory and Applications", *Trends in Pharmacological Sciences* vol. 23, No. 9, 2002, pp. 412-417.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sriyudthsak, M., et al., "Enzyme-Epoxy Membrane Based Glucose Analyzing System and Medical Applications", *Biosensors & Bioelectronics*, vol. 11, No. 8, 1996, pp. 735-742.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, F., et al., "Does Fall In Tissue Glucose Precede Fall In Blood Glucose?" *Diabetologia*, vol. 29, 1996, pp. 609-612.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Street, J. O., et al., "A Note on Computing Robust Regression Estimates Via Interactively Reweighted Least Squares", *The American Statistician*, vol. 42, No. 2, 1988, pp. 152-154.

Suaning, G. J., et al., "CMOS Neurostimulation ASIC with 100 Channels, Scaleable Output, and Bidirectional Radio-Frequency Telemetry" *IEEE Transactions on Biomedical Engineering*, vol. 48, No. 2, 2001, pp. 248-260.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tamura, T., et al., "Preliminary Technique Study of Continuous Glucose Monitoring with a Microdialysis Technique and a Null Method—a Numerical Analysis", *Frontiers Medical and Biological Engineering*, vol. 10, No. 2, 2000, pp. 147-156.

Tanenberg, R. J., et al., "Continuous Glucose Monitoring System: A New Approach to the Diagnosis of Diabetic Gastroparesis", *Diabetes Technology & Therapeutics*, vol. 2, Sup. 1, 2000, pp. S73-S80.

Tang, L, et al., "Fibrin(ogen) Mediates Acute Inflammatory Responses to Biomaterials", *Journal of Experimental Medicine*, vol. 178, 1993, pp. 2147-2156.

Tang, L., et al., "Inflammatory Responses to Biomaterials", *American Journal of Clinical Pathology*, vol. 103, No. 4, 1995, pp. 466-471.

Tang, L., et al., "Mast Cells Mediate Acute Inflammatory Responses to Implanted Biomaterials", *Proceedings of the National Academy of Sciences USA*, vol. 95, 1998, pp. 8841-8846.

Tang, L., et al., "Molecular Determinants of Acute Inflammatory Responses to Biomaterials", *Journal of Clinical Investigation*, vol. 97, No. 5, 1996, pp. 1329-1334.

Tang, Z., et al., "Data Transmission from an Implatable Biotelemeter by Load-Shift Keying Using Circuit Configuration Modulator", *IEEE Transcations on Biomedical Engineering*, vol. 42, No. 5, 1995, pp. 524-528.

Tarasevich, M. R., "Bioelectrocatalysis", *Comprehensive Treatise of Electrochemistry*, vol. 10, 1985, pp. 231-295.

Tatsuma, T., et al., "Enzyme Monolayer - and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with $[(Os-4,4'-dimethoxy-2,2'-bipyridine)Cl]^{+/2+}$", *Journal of ElectroAnalytical Chemistry*, vol. 396, 1995, pp. 511-515.

Thome-Duret, V., et al., "Continuous Glucose Monitoring in the Free-Moving Rat", *Metabolism*, vol. 47, No. 7, 1998, pp. 799-803.

Thome-Duret, V., et al., "Modification of the Sensitivity of Glucose Sensor Implanted into Subcutaneous Tissue", *Diabetes & Metabolism*, vol. 22, No. 3, 1996, pp. 174-178.

Tibell, A., et al., "Survival of Macroencapsulated Allogeneic Parathyriod Tissue One Year After Transplantation in Nonimmunosuppressed Humans", *Cell Transplantation*, vol. 10, No. 7, 2001, pp. 591-599.

Tierney, M. J., "The GlucoWatch® Biographer: A Frequent, Automatic and Noninvasive Glucose Monitor", *Annals of Medicine*, vol. 32, 2000, pp. 632-641.

Tierney, M. J., et al., "Effect of Acetaminophen on the Accuracy of Glucose Measurements Obtained with the GlucoWatch Biographer", *Diabetes Technology & Therapeutics*, vol. 2, No. 2, 2000, pp. 199-207.

Tilbury, J. B., et al., "Receiver Operating Characteristic Analysis for Intelligent Medical Systems—A New Approach for Finding Confidence Intervals", *IEEE Transactions on Biomedical Engineering*, vol. 47, No. 7, 2000, pp. 952-963.

Trajanoski, Z., et al., "Neural Predictive Controller for Insulin Delivery Using the Subcutaneous Route", *IEEE Transactions on Biomedical Engineering*, vol. 45, No. 9, 1998, pp. 1122-1134.

Trecroci, D., "A Glimpse Into the Future: Continuous Monitoring of Glucose with a Microfiber", *Diabetes Interview*, 2002, pp. 42-43.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Department of Health and Human Services, "Off-The-Shelf-Software Use in Medical Devices", *Guidance for Industry, FDA Reviewers and Compliance on*, 1999, pp. 1-26.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "A Subcutaneous Glucose Sensor with Improved Longevity, Dynamic Range, and Stability of Calibration", *Diabetes Care*, vol. 23. No. 2, 2000, pp. 208-214.

Updike, S. J., et al., "Continuous Glucose Monitor Based on an Immobilized Enzyme Electrode Detector", *The Journal of Laboratory and Clinical Medicine*, vol. 93, No. 4, 1979, pp. 518-527.

Updike, S. J., et al., "Enzymatic Glucose Sensors: Improved Long-Term Performance In Vitro and In Vivo", *American Society for Artificial Internal Organs Journal*, 1994, pp. 157-163.

Updike, S. J., et al., "Implanting the Glucose Enzyme Electrode: Problems, Progress, and Alternative Solutions", *Diabetes Care*, vol. 5, No. 3, 1982, pp. 207-212.

Updike, S. J., et al., "The Enzyme Electrode", *Nature*, vol. 214, 1967, pp. 986-988.

Urban, G., et al., "Miniaturized Thin-Film Biosensors Using Covalently Immobilized Glucose Oxidase", *Biosensors & Bioelectronics*, vol. 6, 1991, pp. 555-562.

Valdes, T. I., et al., "In Vitro and In Vivo Degradation of Glucose Oxidase Enzyme Used for an Implantable Glucose Biosensor", *Diabetes Technology & Therapeutics*, vol. 2, No. 3, 2000, pp. 367-376.

Varalli, M., et al., "A Microdialysis Technique for Continuous Subcutaneous Glucose Monitoring in Diabetic Patients (Part 2)", *Biosensors & Bioelectronics*, vol. 18, 2003, pp. 899-905.

Velho, G., et al., "In Vitro and In Vivo Stability of Electrode Potentials in Needle-Type Glucose Sensors", *Diabetes*, vol. 38, No. 2, 1989, pp. 164-171.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wade Jr., L. G., "Chapter 17: Reactions of Aromatic Compounds", *Organic Chemistry, Sixth Edition*, 2006, pp. 762-763.

Wagner, J. G., et al., "Continuous Chimpanzee Amperometric Monitoring of Glucose in a Brittle Diabetic Chimpanzee with a Miniature Subcutaneous Electrode", *Proceedings of the National Academy of Sciences USA*, 1998, pp. 6379-9382.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Highly Selective Membrane-Free, Mediator-Free Glucose Biosensor", *Analytical Chemistry*, vol. 66, No. 21, 1994, pp. 3600-3606.

Wang, J., et al., "Screen-Printable Sol-Gel Enzyme-Containing Carbpm Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Wang, X., et al., "Improved Ruggedness for Membrane-Based Amperometric Sensors Using a Pulsed Amperometric Method", *Analytical Chemistry*, vol. 69, No. 21, 1997, pp. 4482-4489.

Ward, W. K., et al., "A New Amperometric Glucose Microsensor: In Vitro and Short-Term In Vivo Evaluation", *Biosensors & Bioelectronics*, vol. 17, 2002, pp. 181-189.

Ward, W. K., et al., "Assessment of Chronically Implanted Subcutaneous Glucose Sensors in Dogs: The Effect of Surrounding Fluid Masses", *American Society for Artificial Internal Organs Journal*, 1999, pp. 555-561.

Ward, W. K., et al., "Rise in Background Current Over Time in a Subcutaneous Glucose Sensor in the Rabbit: Relevance to Calibration and Accuracy", *Biosensors & Bioelectronics*, vol. 15, 2000, pp. 53-61.

Ward, W. K., et al., "Understanding Spontaneous Output Fluctuations of an Amperometric Glucose Sensor: Effect of Inhalation Anesthesia and Use of a Nonenzyme Containing Electrode", *American Society for Artificial Internal Organs Journal*, 2000, pp. 540-546.

Wientjes, K. J. C., *Development of a Glucose Sensor for Diabetic Patients*, 2000, pp. vii-xiii.

Wilkins, E., et al., "Glucose Monitoring: State of the Art and Future Possibilities", *Medical Engineering and Physics*, vol. 18, No. 4, 1995, pp. 273-288.

Wilkins, E., et al., "Integrated Implantable Device for Long-Term Glucose Monitoring", *Biosensors & Bioelectronics*, vol. 10, 1995, pp. 485-494.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Enzyme-Based Biosensors for In Vivo Measurements", *Chemical Reviews*, vol. 100, No. 7, 2000, pp. 2693-2704.

Wood, W. D., et al., "Hermetic Sealing with Epoxy", *Mechanical Engineering*, 1990, pp. 46-48.

Wu, H., et al., "In Situ Electrochemical Oxygen Generation with an Immunoisolation Device", *Annals of the new York Academy of Sciences*, vol. 875, 1999, pp. 105-125.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yang, Q., et al., "Development of Needle-Type Glucose with High Selectivity", *Sensors and Actuators B*, vol. 46, 1998, pp. 249-256

Yang, S., et al., "A Glucose Biosensor Based on an Oxygen Electrode: In-Vitro Performances in Model Buffer Solution and in Blood Plasma", *Biomedical Instrumentation & Technology*, vol. 30, No. 1, 1996, pp. 55-61.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zavalkoff, S. R., et al., "Evaluation of Conventional Blood Glucose Monitoring as an Indicator of Integrated Glucose Values Using a Continuous Subcutaneous Sensor", *Diabetes Care*, vol. 25, No. 9, 2002, pp. 1603-1606.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

Zhu, J., et al., "Planar Amperometric Glucose Sensor Based on Glucose Oxidase Immobilized by Chitosan Film on Prussian Blue Layer", *Sensors*, vol. 2, 2002, pp. 127-136.

U.S. Appl. No. 12/506,217, Office Action mailed Oct. 20, 2010.

* cited by examiner

ANALYTE MONITORING SYSTEM AND METHOD

RELATED APPLICATIONS

This application claims priority under 35 USC §119 to Provisional Application No. 60/804,170 filed Jun. 7, 2006 entitled "Analyte Monitoring", and to Provisional Application No. 60/804,169 filed Jun. 7, 2006 entitled "Analyte Monitoring System" the disclosure of each of which are incorporated in their entirety by reference for all purposes

BACKGROUND OF THE INVENTION

The association of chronic hyperglycemia and the devastating long-term complications of diabetes was clearly established by the Diabetes Control and Complication Trial (DCCT) (The Diabetes Control and Complications Trial Research Group. "The effect of intensive treatment of diabetes on the development and progression of long-term complications of insulin-dependent diabetes mellitus" N Engl J Med 329: 978-986, 1993; Santiago J V "Lessons from the Diabetes Control and Complications Trial" Diabetes 1993, 42: 1549-1554).

The DCCT found that in patients receiving intensive insulin therapy, there was a reduced risk of 76% for diabetic retinopathy, 50% for diabetic nephropathy and 60% for diabetic neuropathy. The long-term benefits of tight glycemic control have been further substantiated by the Epidemiology of Diabetes Interventions and Complications study which found over a 50% reduced risk of macrovascular disease as a result of intensive insulin therapy (The Diabetes Control and Complications Trial/Epidemiology of Diabetes Intervention and Complication (DCCT/EDIC) Study Group, "Intensive diabetes treatment and cardiovascular disease in patients with type 1 diabetes", 353, 2643-2653, 2005).

However, the DCCT found that patients receiving intensive insulin therapy were at a threefold increased risk of severe hypoglycemia. Patients adhering to intensive insulin therapy regimens were found to have lowered thresholds for activation of neurogenic warning systems and consequently were at increased risk for more severe hypoglycemic events. (Amiel S A, Tamborlane W V, Simonson D C, Sherwin R S., "Defective glucose counterregulation after strict glycemic control of insulin-dependent diabetes mellitus." N Engl J. Med. 1987 28; 316(22):1376-83).

The increased risk of hypoglycemia and the fear associated with patients' perception of that risk has been cited as the leading obstacle for patients to achieve the targeted glycemic levels (Cryer P E. "Hypoglycaemia: The limiting factor in the glycemic management of type I and type II diabetes" Diabetologia, 2002, 45: 937-948). In addition to the problem of chronic hyperglycemia contributing to long-term complications and the problem of acute iatrogenic hypoglycemia contributing to short-term complications, recent research suggests that transient episodes of hyperglycemia can lead to a wide range of serious medical problems besides previously identified microvascular complications as well as macrovascular complications such as increased risk for heart disease. (Haffner S "The importance of postprandial hyperglycemia in development of cardiovascular disease in people with diabetes" International Journal of Clinical Practice, 2001, Supplement 123: 24-26; Hanefeld M: "Postprandial hyperglycemia: noxious effects on the vessel wall" *International Journal of Clinical Practice,* 2002, Supplement 129: 45-50).

Additional research has found that glycemic variation and the associated oxidative stress may be implicated in the pathogenesis of diabetic complications (Hirsh I B, Brownlee M "Should minimal blood glucose variability become the gold standard of glycemic control?" J of Diabetes and Its Complications, 2005, 19: 178-181; Monnier, L., Mas, E., Ginet, C., Michel, F., Villon L, Cristol J-P, and Collette C, "Activation of oxidative stress by acute glucose fluctuations compared with sustained chronic hyperglycemia in patients with type 2 diabetes". JAMA 2006, 295, 1681-1687). Glycemic variation has also been identified as a possible explanation for the increased prevalence of depression in both type 1 and type 2 diabetes (Van der Does F E. De Neeling J N, Snoek F J, Kostense P J, Grootenhuis P A, Bouter L M, and R J Heine: Symptoms and well-being in relation to glycemic control in type II diabetes Diabetes Care, 1996, 19: 204-210; De Sonnaville J J. Snoek F J. Colly L P. Deville W. Wijkel D. Heine R J: "Well-being and symptoms in relation to insulin therapy in type 2 diabetes" Diabetes Care, 1998, 21:919-24; Cox D J, Gonder-Frederick L A, McCall A, et al. "The effects of glucose fluctuation on cognitive function and QOL: the functional costs of hypoglycaemia and hyperglycaemia among adults with type 1 or type 2 diabetes" International Journal of Clinical Practice, 2002, Supplement 129: 20-26).

The potential benefits of continuous glucose monitoring have been recognized by numerous researchers in the field (Skyler J S "The economic burden of diabetes and the benefits of improved glycemic control: the potential role of a continuous glucose monitoring system" Diabetes Technol Ther 2 (Suppl 1): S7-S12, 2000; Tansey M J, Beck R W, Buckingham B A, Mauras N, Fiallo-Scharer R, Xing D, Kollman C, Tamborlane W V, Ruedy K J, "Accuracy of the modified Continuous Glucose Monitoring System (CGMS) sensor in an outpatient setting: results from a diabetes research in children network (DirecNet) study." Diab. Tech. Ther. 7(1):109-14, 2005; Klonoff, D C: "Continuous glucose monitoring: Roadmap for 21st century diabetes therapy" Diabetes Care, 2005, 28: 1231:1239). Accurate and reliable real-time continuous glucose monitoring devices have the ability to alert patients of high or low blood sugars that might otherwise be undetected by episodic capillary blood glucose measurements.

Continuous glucose monitors have the potential to permit more successful adherence to intensive insulin therapy regimens and also to enable patients to reduce the frequency and extent of glycemic fluctuations. However, the development of this technology has proceeded more slowly than anticipated. For example, two recent comprehensive reviews of decades of research in the field cited the lack of accuracy and reliability as the major factor limiting the acceptance of this new technology as well as the development of an artificial pancreas (Chia, C. W. and Saudek, C. D., "Glucose sensors: toward closed loop insulin delivery" Endocrinol. Metab. Clin. N. Am., 33, 174-195, 2004; Hovorka, R. "Continuous glucose monitoring and closed-loop systems" Diabet. Med. 23, 1-12, 2006).

As continuous analyte monitoring becomes more prevalent, of use are continuous analyte sensors and systems that are accurate to such a high degree that confirmatory analyte measurement are not needed to verify the continuous sensing measurements, e.g., prior to a user relying on the continuous measurements. Also of interest are such sensors that work in concert with a drug delivery device.

SUMMARY OF THE INVENTION

Generally, the present disclosure relates to methods and devices for monitoring of the level of an analyte using a continuous and/or automatic in vivo monitoring analyte sensor. Embodiments include sensors in which at least a portion of the sensor is adapted to be positioned beneath the skin of a user and which are adapted for providing clinically accurate analyte data, i.e., data with accuracy sufficient so that a user may confidently rely on the sensor results, e.g., to manage a disease condition and/or make a healthcare decision based thereon. Accordingly, sensors capable of providing clinically accurate (i.e., clinically relevant) analyte information to a user are provided.

Embodiments include continuous analyte monitoring systems that do not require additional analyte information obtained by a second system and/or sensor to confirm the results reported by the continuous sensing system.

Embodiments also include high accuracy continuous analyte sensors and systems with drug delivery systems e.g., insulin pumps, or the like. A communication link (e.g., by cable or wirelessly such as by infrared (IR) or RF link or the like) may be provided for transfer of data from the sensor to the drug delivery device. The drug delivery device may include a processor to determine the amount of drug to be delivered using sensor data, and may deliver such drug automatically or after user direction to do so.

Also provided are methods of analyte monitoring using highly accurate continuous analyte sensors.

These and other objects, features and advantages of the present disclosure will become more fully apparent from the following detailed description of the embodiments, the appended claims and the accompanying drawings.

BRIEF DESCRIPTIONS OF THE DRAWINGS

The figures shown herein are not necessarily drawn to scale, with some components and features being exaggerated for clarity. Each of the figures diagrammatically illustrates aspects of the present disclosure. Of these:

DETAILED DESCRIPTION

Figure 1:
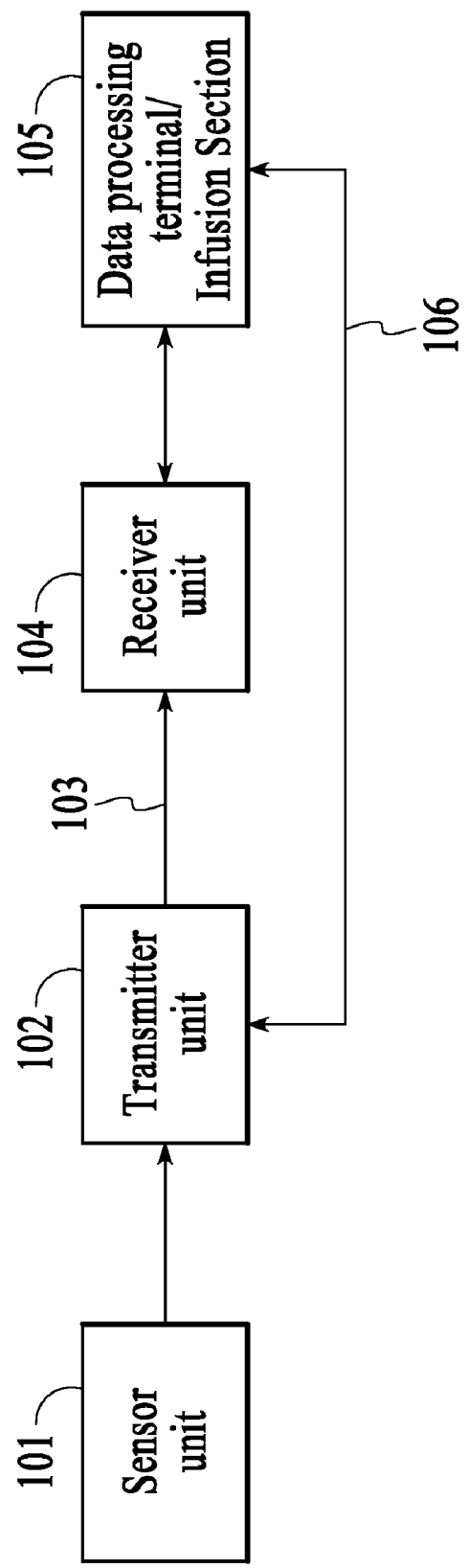
FIG. 1 is a block diagram of one embodiment of a highly accurate continuous glucose monitoring system such as Freestyle Navigator® system using a subcutaneously implantable analyte sensor, according to one embodiment of the present disclosure.

Before the various embodiments of the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges is also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which this present disclosure belongs. Although any methods and materials similar or equivalent to those described herein can also be used in the practice or testing of various embodiments of the present disclosure, exemplary methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The present disclosure is applicable to analyte monitoring systems using a sensor—at least a portion of which is positioned beneath the skin of the user, for the in vivo determination of a concentration of an analyte, such as glucose, lactate, and the like, in a body fluid. The sensor may be, for example, subcutaneously positioned in a patient for the continuous or periodic monitoring an analyte in a patient's interstitial fluid. This may be used to infer the glucose level in the patient's bloodstream. The sensors of the subject disclosure also include in vivo analyte sensors for insertion into a vein, artery, or other portion of the body containing fluid. A sensor of the subject disclosure may be configured for monitoring the level of the analyte over a time period which may range from hours, days, weeks, or longer, as described in greater detail below.

More specifically, FIG. 1 illustrates a data monitoring and management system such as, for example, analyte (e.g., glucose) monitoring system 100, in accordance with one embodiment of the present disclosure. The subject disclosure is further described primarily with respect to a glucose monitoring system for convenience and such description is in no way intended to limit the scope of the present disclosure. It is to be understood that the analyte monitoring system may be configured to monitor a variety of analytes. Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin, and the like. The concentration of drugs, such as, for example, antibiotics (e.g., gentamicin, vancomycin, and the like), digitoxin, digoxin, drugs of abuse, theophylline, and warfarin, and the like, may also be monitored.

The analyte monitoring system 100 includes a highly accurate sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104. Moreover, the data processing terminal in one embodiment may be configured to receive data directly from the transmitter unit 102 via a communication link 106 which may optionally be configured for bi-directional communication. Some or all of the various components may be separate components, or some or all may be integrated into a single unit.

Only one sensor 101, transmitter unit 102, receiver unit 104, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, receiver unit 104, communication link 103, and data processing terminal 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to, e.g., mounted on, the sensor 101 so that both devices are positioned on the user's body. The transmitter unit 102 performs data processing such as filtering and encoding on data signals, each of which corresponds to a sampled analyte level of the user, for transmission to the receiver unit 104 via the communication link 103.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In certain embodiments, in operation, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the receiver unit 104 and the data processing terminal 105 may each be configured for bi-directional wireless communication such that each of the transmitter unit 102, the receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bi-directional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Continuous Glucose Monitoring Sensors and Systems

As described above, the various embodiments of the present disclosure relate to continuous analyte sensors and systems having a high degree of accuracy, e.g., as demonstrated by a Clark Error Grid, Parks Error Grid, Continuous Glucose Error Grid, MARD analysis, and the like. The high degree of accuracy permits a user to rely on the results of the sensor without the need to confirm sensor results. In certain embodiments, the sensors have at least about 80% of its paired data points within zone A of one or more of the Clark Error Grid, the Consensus Error Grid, or the Continuous Glucose Error Grid Analysis, e.g., at least about 85% of its paired data points within zone A of one or more of the Clark Error Grid, the Consensus Error Grid, or the Continuous Glucose Error Grid Analysis, e.g., at least about 90% of its paired data points within zone A of one or more of the Clark Error Grid, the Consensus Error Grid, or the Continuous Glucose Error Grid Analysis, e.g., at least about 95% of its paired data points within zone A of one or more of the Clark Error Grid, the Consensus Error Grid, or the Continuous Glucose Error Grid Analysis.

In certain embodiments, a sensor may have about 80% or greater, e.g., 85% or greater, e.g., 90% or greater of its paired data points within zone A of the Clark Error Grid, and 80% or greater, e.g., 85% or greater, e.g., 90% or greater, of its paired data points within zone A of the Consensus Error Grid.

The sensors are continuous analyte monitoring sensors. The sensors are adapted to continuously or periodically monitor analyte levels for a period of time, e.g., usually at least about 24 hours, e.g., about 1 day to about 30 days, e.g., about 3 days to about 7 days, e.g., a 5 day sensor or 7 day sensor.

Embodiments of the clinically accurate continuous glucose monitoring systems of the present disclosure include four components: a small, miniaturized analyte sensor element (which may be an electrochemical or optical sensor) for placement in the subcutaneous adipose tissue in the arm or abdomen (or elsewhere); a disposable sensor delivery unit containing a spring-loaded sharp for mechanical insertion of the sensor into the tissue and a sensor support mount; a transmitter (e.g., wireless transmitter) which connects to the sensor support mount on the skin surface and to the inserted electrochemical sensor; and a hand-held receiver device for communication (e.g., wireless) with the transmitter and for the communication (e.g., audio and/or visual display) of the continuous glucose values to the user. The system may also include a data management system in which information from the receiver (and/or transmitter) is forwarded (e.g., wirelessly or otherwise) to a data management system such as a personal computer ("PC"), personal digital assistant ("PDA"), telephone, facsimile machine, drug delivery device (e.g., internal or external insulin pump) or the like.

Embodiments of the sensors of the present disclosure vary, but in all embodiments have a high degree of accuracy. In other words, the sensors' accuracy enables a user of the system to solely and confidently rely on the sensors' results that are reportable to the user, e.g., to manage a disease state such as diabetes or the like, make healthcare decisions (e.g., insulin delivery, meals, exercise, etc.). In this manner, adjunctive measurements are not required to confirm the readings of the highly accurate sensors of the present disclosure, thereby eliminating burdensome and painful fingersticks required for testing analyte using conventional blood analyte monitoring systems such as blood glucose test strips and the like, used for such confirmations.

In certain embodiments a sensor is adapted to be wholly or partially positioned beneath the skin surface of a user. A sensor may be a transcutaneous sensor in which a portion of the sensor is configured to be positioned beneath a skin surface and portion is configured to be positioned above the skin surface. In many embodiments at least a portion of the sensor is configured to be inserted into the subcutaneous adipose tissue. Sensors may vary in size, where in certain embodiments a sensor may be about 5.5 mm long, about 600 microns wide and about 250 microns thick. Sensors having different lengths and/or widths and/or thicknesses are also encompassed by the present disclosure. The sensors are configured to accurately measure an analyte, e.g., glucose concentration in the interstitial fluid, which has correlates with blood glucose. The sensor is typically provided to a user as a sterile, single-use disposable element.

The sensors may be configured to continuously monitor analyte levels of a user for a period of time. In certain embodiments, the period of time ranges from about 1 day to about 30 days, e.g., from about 3 days to about 7 days, where in certain embodiments a sensor may configured for up to about five days of continuous use. A system may include two or more sensors, which may be temporally overlapped for a certain period of usage time, thereby extending the amount of time of continuous sensing and/or doing away with any time gaps that may result from removing a first sensor and inserting a second. Furthermore, a sensor may be calibrated from a previous sensor in certain embodiments.

The glucose measurement is made using sensing chemistry. Sensing chemistry may include an enzyme and may include a mediator. In certain embodiments, the sensing chemistry is a modified glucose oxidase polymeric matrix with an osmium dopant in the supporting polymer matrix. The sensing chemistry (also referred to as the "transduction chemistry") used in the sensors of the present disclosure permits detection of signal, e.g., a nanoampere electrical current from the reaction with an applied potential, such as of only about 40 mV.

More specifically, in one embodiment, the sensor includes at least one working electrode formed on a substrate. The sensor may also include at least one counter electrode (or counter/reference electrode) and/or at least one reference electrode. The counter electrode and/or reference electrode may be formed on the substrate or may be separate units. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient.

The working electrode or electrodes are formed using conductive traces disposed on the substrate. The counter electrode and/or reference electrode, as well as other optional portions of the sensor, such as a temperature probe, may also be formed using conductive traces disposed on the substrate. These conductive traces may be formed over a smooth surface of the substrate or within channels formed by, for example, embossing, indenting or otherwise creating a depression in the substrate.

A sensing layer is often formed proximate to or on at least one of the working electrodes to facilitate the electrochemical detection of the analyte and the determination of its level in the sample fluid, particularly if the analyte can not be electrolyzed at a desired rate and/or with a desired specificity on a bare electrode. The sensing layer may include an electron transfer agent to transfer electrons directly or indirectly between the analyte and the working electrode. The sensing layer may also contain a catalyst to catalyze a reaction of the analyte. The components of the sensing layer may be in a fluid or gel that is proximate to or in contact with the working electrode. Alternatively, the components of the sensing layer may be disposed in a polymeric or sol-gel matrix that is proximate to or on the working electrode. In one aspect, the components of the sensing layer are non-leachably disposed within the sensor. Further, the components of the sensor are immobilized within the sensor.

In addition to the electrodes and the sensing layer, the sensor may also include a temperature probe, a mass transport limiting layer, a biocompatible layer, and/or other optional components, as described below. Each of these items enhances the functioning of and/or results from the sensor, as discussed below.

The Substrate

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. In other embodiments, the sensors are made using a relatively rigid substrate to, for example, provide structural support against bending or breaking.

Conductive Traces

At least one conductive trace is formed on the substrate for use in constructing a working electrode. In addition, other conductive traces may be formed on the substrate for use as electrodes (e.g., additional working electrodes, as well as counter, counter/reference, and/or reference electrodes) and other components, such as a temperature probe. The conductive traces may be formed on the substrate by a variety of techniques, including, for example, photolithography, screen printing, or other impact or non-impact printing techniques. The conductive traces may also be formed by carbonizing conductive traces in an organic (e.g., polymeric or plastic) substrate using a laser.

The conductive traces are typically formed using a conductive material 56 such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting.

In addition to the particles of carbon, metal, alloy, or metallic compound, the conductive ink may also contain a binder. The binder may optionally be cured to further bind the conductive material within the channel and/or on the substrate.

Suitable redox couples for binding to the conductive material of the reference electrode include, for example, redox polymers (e.g., polymers having multiple redox centers.). In one aspect, the reference electrode surface may be non-corroding so that an erroneous potential is not measured. Examples of conductive materials include less corrosive metals, such as gold and palladium, and may include non-corrosive materials including non-metallic conductors, such as carbon and conducting polymers. A redox polymer can be adsorbed on or covalently bound to the conductive material of the reference electrode, such as a carbon surface of a conductive trace. Non-polymeric redox couples can be similarly bound to carbon or gold surfaces.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking.

Another method for immobilizing the redox polymer includes the functionalization of the electrode surface and then the chemical bonding, often covalently, of the redox polymer to the functional groups on the electrode surface.

Sensing Layer

Some analytes, such as oxygen, can be directly electrooxidized or electroreduced on the working electrode. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode. For these analytes, each working electrode has a sensing layer formed proximate to or on a working surface of the working electrode. Typically, the sensing layer is formed near or on only a small portion of the working electrode, often near a tip of the sensor. This limits the amount of material needed to form the sensor and places the sensing layer 64 in the best position for contact with the analyte-containing fluid (e.g., a body fluid, sample fluid, or carrier fluid).

Electron Transfer Agent

In many embodiments, the sensing layer contains one or more electron transfer agents in contact with the conductive material of the working electrode. In some embodiments of the present disclosure, there is little or no leaching of the electron transfer agent away from the working electrode during the period in which the sensor is implanted in the patient. A diffusing or leachable (i.e., releasable) electron transfer agent often diffuses into the analyte-containing fluid, thereby reducing the effectiveness of the electrode by reducing the sensitivity of the sensor over time.

In some embodiments of the present disclosure, to prevent leaching, the electron transfer agents are bound or otherwise immobilized on the working electrode or between or within one or more membranes or films disposed over the working electrode. The electron transfer agent may be immobilized on the working electrode using, for example, a polymeric or sol-gel immobilization technique. Alternatively, the electron transfer agent may be chemically (e.g., ionically, covalently, or coordinatively) bound to the working electrode, either directly or indirectly through another molecule, such as a polymer, that is in turn bound to the working electrode.

In general, electron transfer agents may be electroreducible and electrooxidizable ions or molecules having redox potentials that are a few hundred millivolts above or below the redox potential of the standard calomel electrode (SCE). Further, the electron transfer agents are not more reducing than about −150 mV and not more oxidizing than about +400 mV versus SCE.

Catalyst

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. In one aspect, the catalyst is non-leachably disposed on the sensor, whether the catalyst is part of a solid sensing layer in the sensor or solvated in a fluid within the sensing layer. In a further aspect, the catalyst is immobilized within the sensor (e.g., on the electrode and/or within or between a membrane or film) to prevent unwanted leaching of the catalyst away from the working electrode and into the patient. This may be accomplished, for example, by attaching the catalyst to a polymer, cross linking the catalyst with another electron transfer agent (which can be polymeric), and/or providing one or more barrier membranes or films with pore sizes smaller than the catalyst.

Biocompatible Layer

An optional film layer is formed over at least that portion of the sensor which is subcutaneously inserted into the patient. This optional film layer may serve one or more functions. The film layer prevents the penetration of large biomolecules into the electrodes. This is accomplished by using a film layer having a pore size that is smaller than the biomolecules that are to be excluded. Such biomolecules may foul the electrodes and/or the sensing layer thereby reducing the effectiveness of the sensor and altering the expected signal amplitude for a given analyte concentration. The fouling of the working electrodes may also decrease the effective life of the sensor. The biocompatible layer may also prevent protein adhesion to the sensor, formation of blood clots, and other undesirable interactions between the sensor and body.

Interferent-Eliminating Layer

An interferent-eliminating layer may be included in the sensor. The interferent-eliminating layer may be incorporated in the biocompatible layer or in the mass transport limiting layer (described below) or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrodes. In one aspect, this type of interferent-eliminating layer is much less permeable to one or more of the interferents than to the analyte.

Mass Transport Limiting Layer

A mass transport limiting layer may be included with the sensor to act as a diffusion-limiting barrier to reduce the rate of mass transport of the analyte, for example, glucose or lactate, into the region around the working electrodes. By limiting the diffusion of the analyte, the steady state concentration of the analyte in the proximity of the working electrode (which is proportional to the concentration of the analyte in the body or sample fluid) can be reduced. This extends the upper range of analyte concentrations that can still be accurately measured and may also expand the range in which the current increases approximately linearly with the level of the analyte. Particularly useful materials for the film layer are membranes that do not swell in the analyte-containing fluid that the sensor tests.

Suitable membranes include 3 to 20,000 nm diameter pores. Membranes having 5 to 500 nm diameter pores with well-defined, uniform pore sizes and high aspect ratios may be used. In one embodiment, the aspect ratio of the pores may be two or greater, or in one aspect five or greater.

Embodiments of the system include a receiver that includes both the signal processing algorithms and the user interface system for operation of the system and display of the results—although one or both may be incorporated wholly or partially into the transmitter of the system. In operation, the glucose display on the main screen of the receiver is updated during a predetermined time period, e.g., about once a minute or the like, and gives the instantaneous continuous glucose value. Also provided may be the direction and/or rate of change averaged over a predetermined period of time, e.g., the preceding fifteen minutes, or the like. The direction may be communicated using any suitable audio and/or visual indicator(s). For example, direction may be displayed with trend arrows that give quantitative ranges of the rate of change in units of about 1 mg/dL/min from about −2 mg/dL/min to about +2 mg/dL/min. The receiver may also include threshold and/or projected warnings—audible and/or visual warnings. These may be settable at the factory and/or by the user to different glucose levels to provide warnings of actual and impending hypo- or hyperglycemia. Other warnings may also be included, e.g., battery level, and the like. Time-to-calibrate indicators may also be included.

The system may also include a blood glucose ("BG") meter for use with glucose test strips which may be used for calibration of the continuous glucose sensor, but as noted above, is not needed to confirm the continuous sensor results. The BG meter may be a separate, though connectable component, or may be integrated into the receiver as a single unitary device. For example, the receiver may include a test strip port and a processor to process a reading from the test strip. The built-in blood glucose meter eliminates the possibility of transcription errors during sensor calibration and also provides the user with a backup glucose meter system.

The continuous glucose systems of the present disclosure may be calibrated according to a predetermined calibration schedule. In certain embodiments, this schedule may be limited to factory-only calibration. However in certain embodiments, the calibration schedule may include calibrations by the user. For example, over the period of use of the system, it may be calibrated from about 0 to about 10 times, e.g., from about 1 to about 5 times, e.g., about 4 times. An exemplary calibration schedule may include calibration 4 times over a 5 day period, e.g., at 10, 12, 24 and 72 hours after sensor insertion. In certain embodiments, the system may be configured for single point calibration, e.g., as described in U.S. Pat. No. 6,121,009 and elsewhere. In other embodiments, exemplary calibration schedule may include calibration 1-2 times over a 5-7 day period. The system may be configured to accept calibration values that fall within a certain range or are at least meet a threshold value. For example, calibration values may be accepted for blood glucose input between about 60 and about 300 mg/dL and when the absolute rate of change of glucose is estimated to be less than about 2 mg/dL/min. These constraints on the acceptance of calibration input values are designed to limit the potential adverse effects of the intrinsic physiological lag between interstitial fluid glucose and blood glucose.

In the embodiments in which at least one calibration by the user is required, the system may be configured so that it does not display (i.e., does not report to the user) real-time glucose values from the continuous monitor until the first calibration, e.g., at about ten hours after sensor insertion in certain instances. This delay after insertion is designed so that the initial system calibration is performed after the sensor has reached a stable equilibrium with the surrounding tissue.

Moreover, in one embodiment, the use of fingerstick calibration in response to the Freestyle Navigator® system hypoglycemic alarm may increase the overall system accuracy.

An exemplary, analyte sensor and sensing system having the high accuracy described herein is the Freestyle Navigator® continuous glucose monitoring system from Abbott Diabetes Care, Inc., of Alameda, Calif.

Kits

Finally, kits are also provided. Embodiments of the subject kits may include one or more highly accurate sensors as described herein. Embodiments may also include a sensor insertion device and/or transmitter and/or receiver. Embodiments may also include a drug delivery device such as an insulin pump.

In certain embodiments, a kit may include a blood glucose meter to be used with the continuous sensing system, e.g., for calibration. The meter may be a separate component from continuous sensing components (in which case a communication link for transferring data from the meter to the sensing system (such as to the receiver) may be included) or may be integrated therein, e.g., the receiver may include a blood glucose meter.

The subject kits may also include written instructions for using a sensor. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the one or more sensors and additional reagents (e.g., control solutions), if present, until use.

EXPERIMENTAL

The accuracy of a highly accurate continuous monitoring system such as the Freestyle Navigator® continuous glucose monitoring system measuring glucose in the interstitial fluid is studied, in comparison with a laboratory reference method over five days of sensor wear.

Study Design and Methods

Fifty-eight subjects with Type 1 diabetes ranging in age from 18-64 were enrolled in a multi-center, prospective, single-arm study. Each subject wore two sensors simultaneously—one on the arm and the other on the abdomen. All the FreeStyle Navigator® devices were calibrated with separate capillary fingerstick measurements at 10, 12, 24 and 72 hours after sensor insertion. Data from the continuous glucose monitor was collected at one-minute intervals for the entire study. Measurements from the FreeStyle Navigator® system were compared with reference venous sample measurements taken in an in-patient clinical research center once every fifteen minutes over a fifty hour time period covering a distribution over the entire 120 hour wear period for the Freestyle Navigator® sensor.

The subjects were admitted to a healthcare facility either in the evening or in the morning for sensor insertion. The sensors were inserted by a health care professional on both the lateral or posterior upper arm and the right or left lower abdominal quadrant using the disposable sensor delivery unit. The subjects returned to the clinic approximately nine hours later for the placement of the venous access line and for the calibration of the sensor using the built-in FreeStyle® blood glucose meter. Calibration of the FreeStyle Navigator® device in this study was deliberately scheduled to occur at different times of day as well as both pre- and post-prandially. During two separate periods in which the subjects were in the clinic and venous samples were being taken, each subject was administered intravenous insulin or a 75 gram fast-acting glucose drink, such as Glucola, in order to obtain data for evaluation of the sensor performance during deliberately-induced periods of rapidly-falling and rapidly-rising glucose. Data from the sensor and transmitter were stored in the receiver with a one minute frequency, but were not displayed to the subjects or the clinic staff. Throughout the study, all the subjects continued with their previously established diabetes management regimen. The high frequency and volume of the venous blood samples, 2.5 mL once every fifteen minutes, required a limitation of 50 hours of intensive testing in order to maintain the total volume of blood drawn from each subject within accepted safety limits. Subjects were assigned to different study schedules so as to provide an optimal distribution of the fifty hours of laboratory reference data over the total five day duration of the sensor life.

Figure 2:
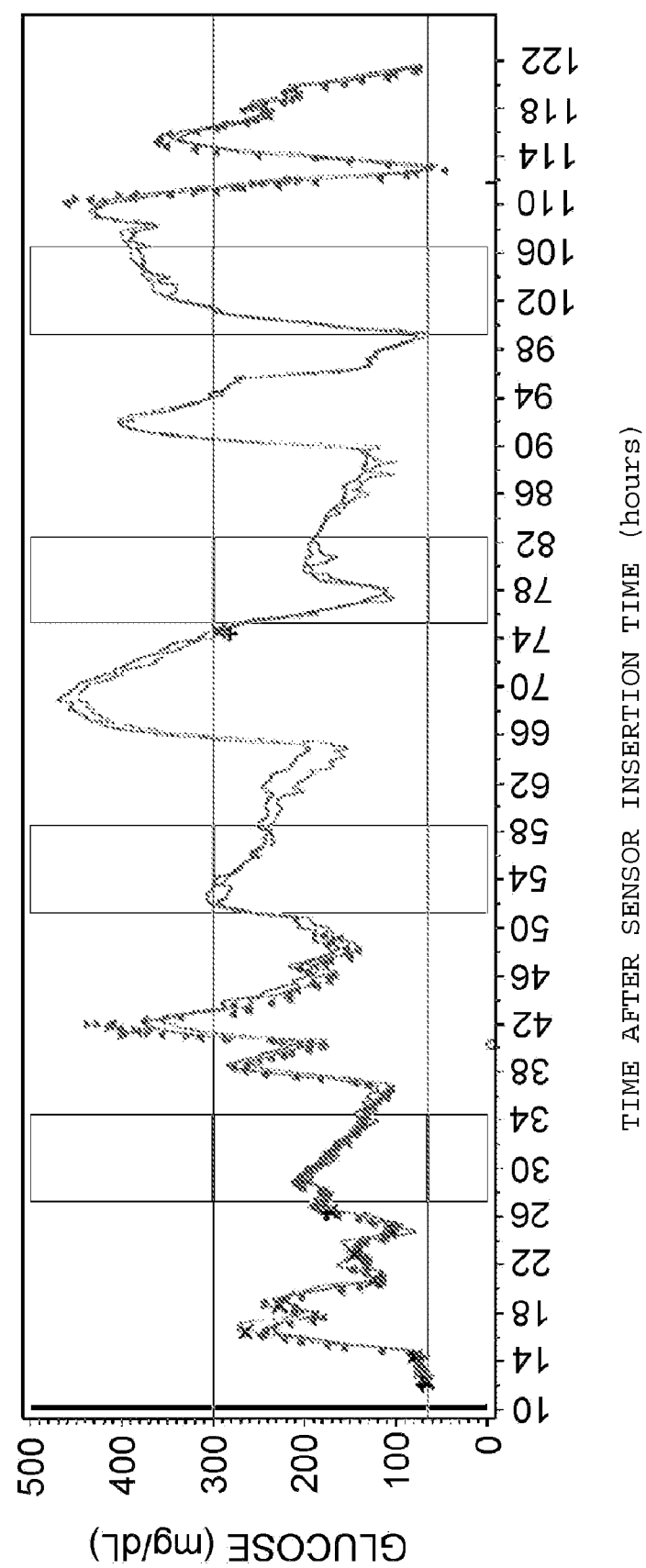
FIG. 2 shows five day accuracy data for the monitoring system of FIG. 1 (arm and abdomen) and 50 hours of YSI venous sampling in one embodiment.

FIG. 2 illustrates five-day data from the Freestyle Navigator® continuous glucose monitor (arm and abdomen) and 50 hours of YSI venous sampling taken two separate in-patient admissions from one subject. The timing of the glucose and insulin challenges is also shown. The shaded blocks are night time. The black solid line is the Freestyle Navigator® sensor in the arm, the dashed line is the sensor in the abdomen. YSI measurements are shown in white triangles. The plus and cross symbols are the Freestyle Navigator® system blood glucose calibrations for the arm and abdominal sensors, respectively.

Referring to FIG. 2, a typical profile plot for the five-days of the study with one-minute data from the arm and abdominal sensors as well as the fifteen minute venous samples taken over three separate periods during the five days. The glucose concentration from the venous sample was measured using a YSI 2300 STAT Plus™ Glucose & Lactate Analyzer YSI analyzer (YSI Life Sciences, Yellow Springs, Ohio). All YSI measurements were made in duplicate from a single blood sample. YSI measurements were multiplied by 1.12 to obtain plasma equivalent value.

Results

A number of separate metrics were used to evaluate the accuracy and performance of the FreeStyle Navigator® system compared with the venous blood samples measured with the laboratory reference method. These metrics included the Clarke error grid, the Consensus error grid, the mean and median absolute relative difference as well as cross-correlation statistics for comparison of abdominal and upper arm sensors. The sensor performance was evaluated for the entire five days, for each day individually as well as diurnally and nocturnally. Characteristic physiological lag times were derived from analysis of the data. The data was also analyzed using the Continuous Glucose Error Grid Analysis (CG-EGA) (Kovatchev, 2004). Finally, the accuracy of the FreeStyle Navigator® system compared to the venous reference samples was analyzed as a function of the measured rates of change in the underlying blood glucose.

Comparison of the FreeStyle Navigator® continuous glucose measurements with the laboratory reference method (n=20,362) gave a mean absolute relative difference of 12.8% and a median absolute relative difference of 9.3%. The percentage in the clinically-accurate Clarke Error Grid zone A was 81.7% and 16.7% in the clinically-acceptable B zone. This included periods of high rates of change of blood glucose during intravenous glucose and insulin challenges. The precision of the matched Freestyle Navigator® sensors worn on the arm and abdomen had a coefficient of variation of 10% (n=312,953). The accuracy remained unchanged over the five days with the percent of data in the Clarke Error Grid Zone A equal to 82.5% on the first day and 80.9% on the fifth day.

Clinical Accuracy Overall

Figure 3:
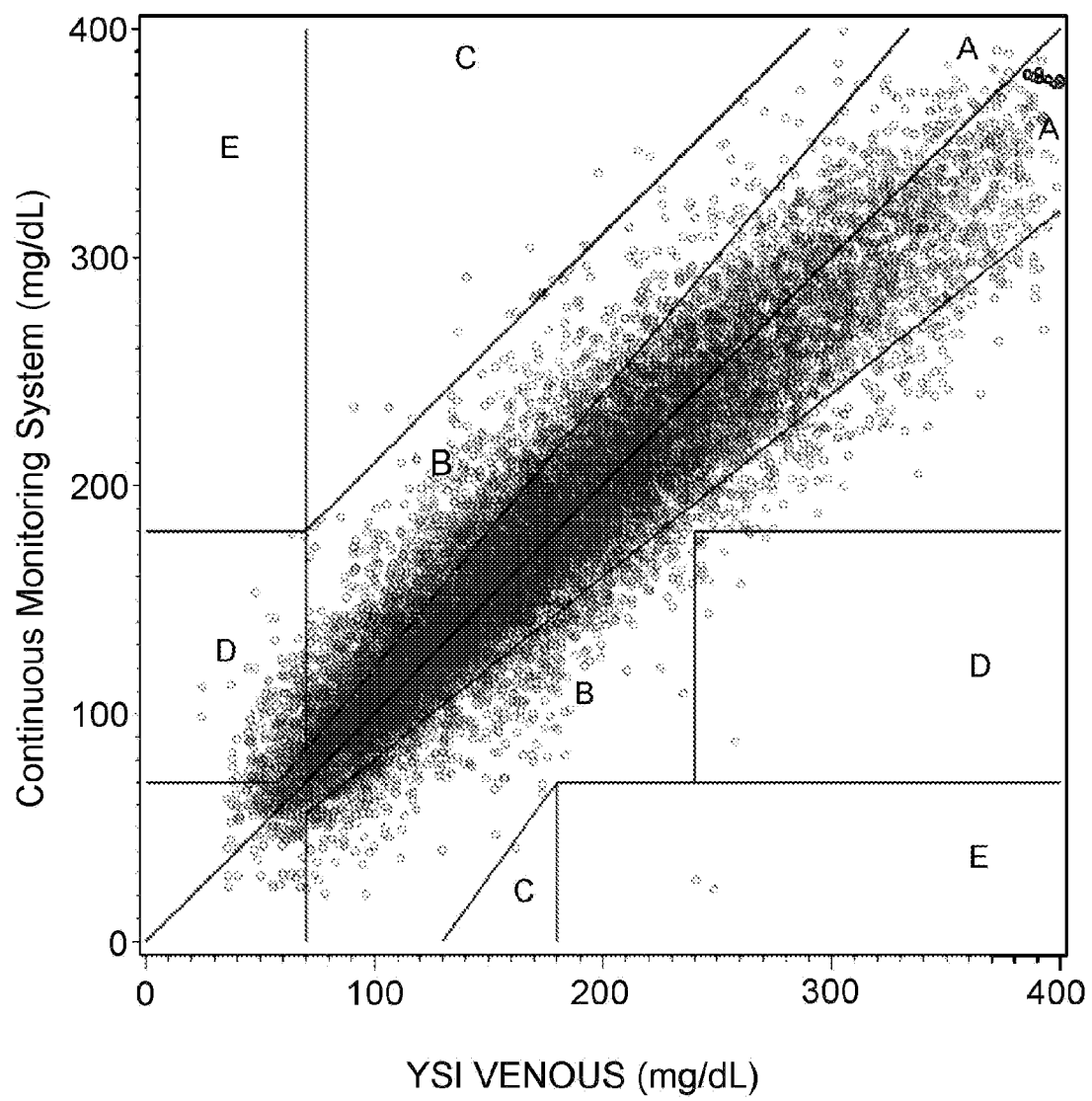
FIG. 3 shows a Clarke error grid for the continuous monitoring system of FIG. 1 in one embodiment.

FIG. 3 shows the Clarke error grid for the study reported herein. More specifically, FIG. 3 illustrates an overall Clarke error grid showing 81.7% in the clinically-accurate A zone, 16.7% of the paired points in the clinically-acceptable or benign error zone B and only 1.7% outside of the A and B zones The Clarke error grid was developed to assess the clinical implications of new glucose monitoring technology relative to accepted reference methods (Cox D J, Clarke W L, Gonder-Frederick L A, Pohl S, Hoover C, Snyder A, "Accuracy of perceiving blood glucose in IDDM", *Diabetes Care*, 8(6): 529-36, 1985; Clarke W L, Cox D, Gonder-Frederick L A, Carter W and Pohl S L. "Evaluating clinical accuracy of systems for self-monitoring of blood glucose" *Diabetes Care*, 10, 622-628, 1987). There were a total of 20,362 paired points for all 58 subjects with YSI venous measurements and Freestyle Navigator® system interstitial fluid glucose measurements. 81.7% of the paired points fell in the Clarke error grid zone A indicating a high level of clinical accuracy. There were 16.7% of the paired points in the clinically-acceptable (benign error) zone "B", 0.1% in the overtreatment error zone "C", 1.9% in the failure to detect error zone "D" and 0.01% in the clinically inaccurate and dangerous error zone "E".

The Consensus error grid has been proposed as an alternative to the original error grid zone demarcations, specifically to eliminate the physical proximity of the clinically-unacceptable D zone with the clinically-accurate A zone in the lower left portion of the grid. The results of the Clarke error grid and the Consensus error grid are summarized in the Table (1) below. The Consensus error grid was also defined with five distinct risk levels, but the definitions were specified in terms of effect on clinical action by the patient. Zone A has no effect. Zone B has little or no effect. Zone C has altered clinical action. Zone D has altered clinical action with significant medical risk. Zone E has altered clinical action with potentially dangerous consequences.

On the Clarke error grid, there were 316 individual points in the D zone. Ninety-five percent of these points were in the lower left quadrant of the error grid.

TABLE (1)

Summary statistics of Clarke and Consensus Error Grid

| Zone | Clarke Error Grid % | N = 20362 | Consensus Error Grid % | N = 20362 |
|---|---|---|---|---|
| A | 81.7 | 16627 | 85.5 | 17419 |
| B | 16.7 | 3398 | 13.6 | 2776 |
| C | 0.1 | 19 | 0.8 | 161 |
| D | 1.6 | 316 | 0.03 | 6 |
| E | 0.0 | 2 | 0.0 | 0 |

On the Consensus error grid, by contrast, the number of points in the significant medical risk D zone is reduced to 6. In addition to the reduction in D zone points, the Consensus error grid shows a higher percentage in the clinically-accurate A zone, a slightly lower percentage in the clinically-acceptable B zone, a slightly higher percentage in the altered clinical action C zone and no points in the dangerous consequence E zone.

The performance of the Freestyle Navigator® system was also assessed using the mean and median absolute relative difference between the sensor interstitial glucose measurements and the YSI venous sample measurements. The mean absolute relative difference was 12.8% and the median absolute relative difference was 9.3%. A comparison of accuracy and performance by day shows that the system's performance on the fifth day is equivalent to the performance of the first or second day. Table (2) contains data with the error grid statistics as well as the mean and median absolute relative difference from the study separated by day.

TABLE (2)

Clarke Error Grid, mean and median absolute relative difference by day

| Zone | Day 1 N | Day 1 % | Day 2 N | Day 2 % | Day 3 N | Day 3 % | Day 4 N | Day 4 % | Day 5 N | Day 5 % |
|---|---|---|---|---|---|---|---|---|---|---|
| A | 4354 | 82.5 | 3215 | 82.4 | 2903 | 79.4 | 1688 | 84.0 | 4467 | 80.9 |
| B | 865 | 16.4 | 646 | 16.6 | 668 | 18.3 | 285 | 14.2 | 934 | 16.9 |
| C | 12 | 0.2 | 4 | 0.1 | 1 | 0.0 | 0 | 0.0 | 2 | 0.0 |
| D | 47 | 0.9 | 34 | 0.9 | 82 | 2.2 | 37 | 1.8 | 116 | 2.1 |
| E | 0 | 0.0 | 2 | 0.1 | 0 | 0.0 | 0 | 0.0 | 0 | 0.0 |
| Mean ARD | | 12.6 | | 12.3 | | 14.1 | | 11.9 | | 13.0 |
| Median ARD | | 9.4 | | 9.3 | | 9.9 | | 7.8 | | 9.5 |
| Total | 5278 | 100.0 | 3901 | 100.0 | 3654 | 100.0 | 2010 | 100.0 | 5519 | 100.0 |

Additional analysis was done comparing the accuracy and performance of the Freestyle Navigator® system nocturnally and diurnally. The percentage of points in the Clarke error grid A zone was 87.1% at night and 80.6% during the day. The difference in accuracy during the day may be associated with the higher rates of change during the daytime, when all of the glucose and insulin challenges were conducted.

The data from the present study has also been analyzed using the Continuous Glucose Error Grid Analysis (CG-EGA), designed to incorporate the extra temporal dimension of data provided by continuous glucose monitoring systems (Kovatchev et al.). The rate analysis using the CG-EGA gave a 81.1% in the rate error grid A zone, 14.4% in the rate error grid B zone, 1.5% in the rate error grid C zone, 2.3% in the rate error grid D zone, and 0.7% in the rate error grid E zone. The point analysis using the CG-EGA gave a 83.6% in point error grid A zone, 15.0% in point error grid B zone, 0.1% in point error grid C zone, 1.3% in point error grid D zone, and 0% in point error grid E zone. The CG-EGA analysis combining rate and point information revealed that accuracy, measured as a percentage of accurate readings plus benign errors, was 97.5% (94.2% accurate, 3.4% benign). The CG-EGA accuracy stratified by glycemic state gave 60.4% in hypoglycemia (53.1% accurate, 7.3% benign), 99.3% in euglycemia (95.7% accurate, 3.6% benign) and 98.2% in hyperglycemia (95.4% accurate, 2.8% benign). The difference in accuracy between the hypoglycemic, euglycemic, and hyperglycemic ranges may be related to the high rate of change often associated with the descent into hypoglycemia. Standard egression analysis and Deming regression analysis both gave small, but significant offsets 24.9 and 14.3 mg/dL) that could contribute to the slight decrease in accuracy in hypoglycemia.

Figure 4A:
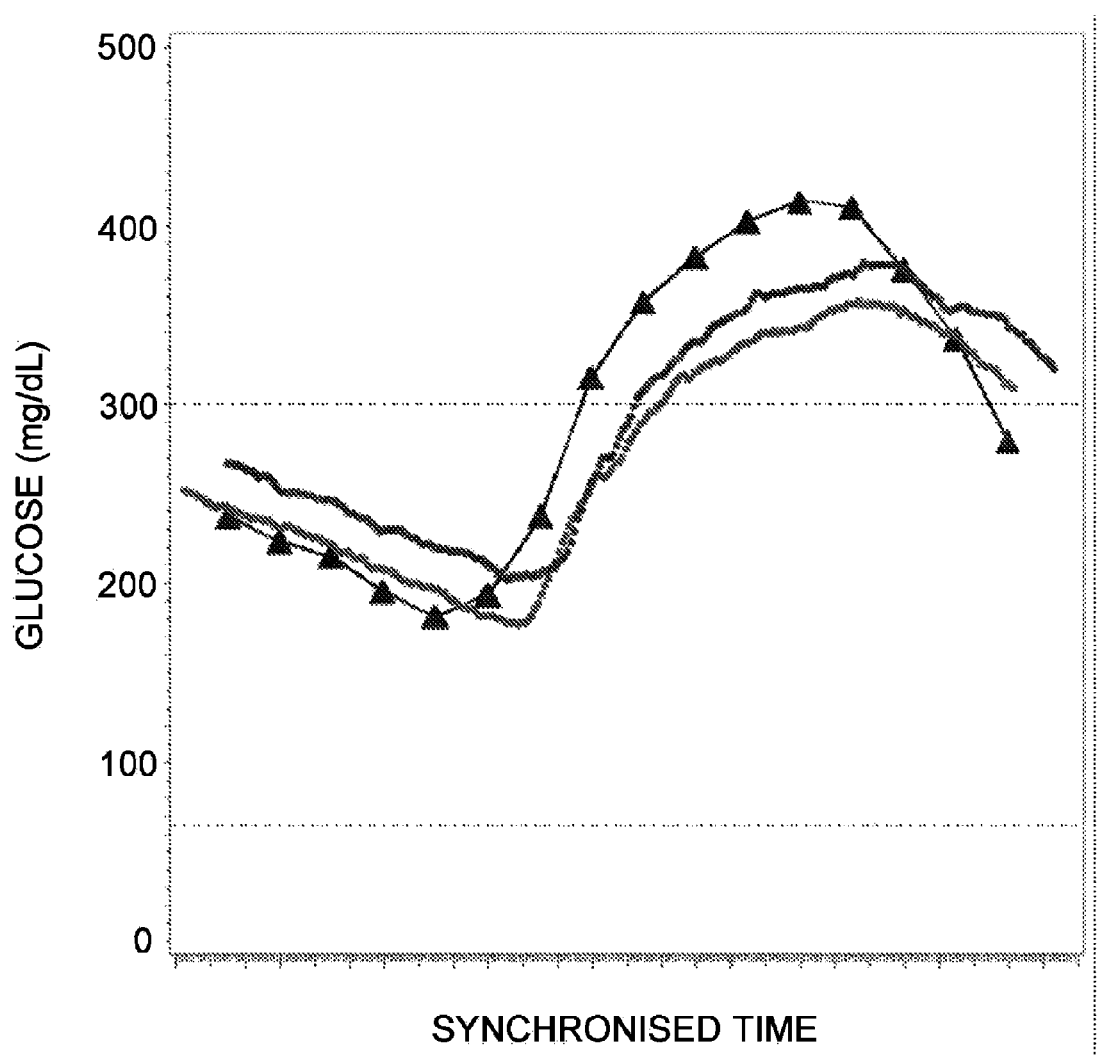
FIG. 4A shows a view (four hour duration) of profile plot centered glucose challenge.
Figure 4B:
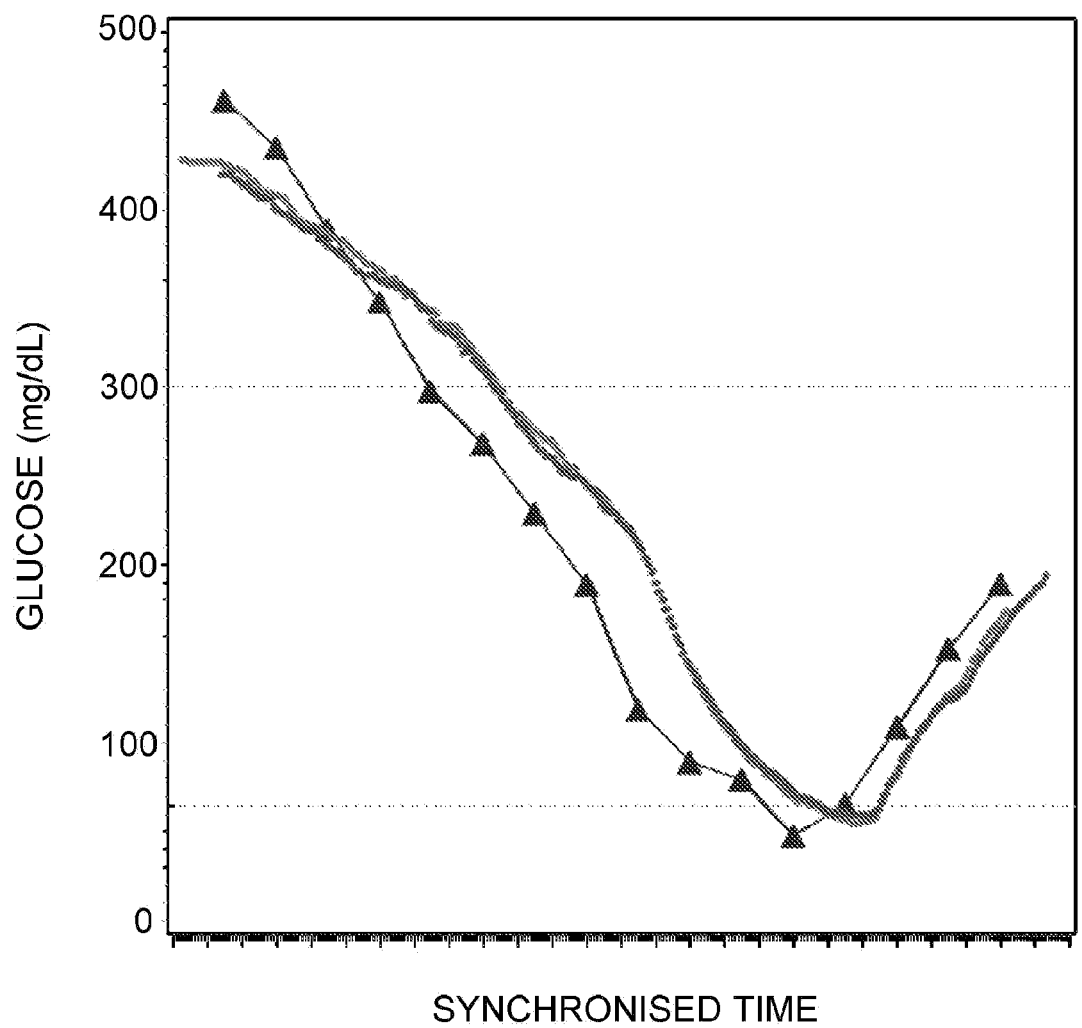
FIG. 4B shows a view (four hour duration) of profile plot centered insulin challenge.

FIGS. 4A and 4B give an expanded view of the data from FIG. 2 on a four-hour time axis and centered about the glucose challenge and the insulin challenge, respectively. More specifically, FIG. 4A illustrates a zoomed in view (four hour duration) of Freestyle Navigator®™ sensor data and YSI measurements during the glucose challenge. Referring to FIG. 4A, the continuous glucose sensor data in one minute intervals are shown in the two solid curves (solid from the arm, dashed from the abdomen). The 15 minute YSI venous sample data are shown in the triangles. The time between the nadir of the YSI data and the Freestyle Navigator® system is approximately 24 minutes. The time between the peak of the YSI data and the Freestyle Navigator® system data is approximately 19 minutes.

Additionally, FIG. 4B shows data from two Freestyle Navigator® sensors, compared with fifteen minutes venous samples measured with the YSI from the insulin challenge in one patient in the study. Referring to FIG. 4B, the Freestyle Navigator® projected alarm, would have alerted the subject to an impending hypoglycemic event 26 minutes before the blood sugar crossed the 70 mg/dL hypoglycemic threshold. At the time of the alarm, the Freestyle Navigator® system glucose was approximately 175 mg/dL and the YSI reading was approximately 90 mg/dL and the rate of change was −3.5 mg/dL/min.

Both FIGS. 4A and 4B show the temporal tracking of the FreeStyle Navigator® system compared against the venous reference samples. The expanded temporal axis used in FIGS. 4A and 4B also permits more direct visualization of the time lag between the Freestyle Navigator® system interstitial fluid glucose measurement and the venous reference sample measurements. The temporal offset between the FreeStyle® Navigator system and the venous reference measurements was also analyzed by applying a time shift in order to minimize the mean absolute relative difference.

After correction for the calibration bias, this resulted in an average 12.8 minute lag between the glucose values measured in the interstitial fluid and in the venous samples. This is consistent with previously published studies on the physiological lag between interstitial fluid glucose and blood glucose (see for example: Rebrin K, Steil G M, van Antwerp W P, Mastrotoraro J J, "Subcutaneous glucose predicts plasma glucose independent of insulin: implications for continuous monitoring", $Am\ J\ Physiol.$, 277(3 Pt 1):E561-71, 1999; Steil G M, Rebrin K, Mastrototaro J, Bernaba B, Saad M F, "Determination of plasma glucose during rapid glucose excursions with a subcutaneous glucose sensor", $Diab.\ Tech.\ Ther,$ 5:27-31, 2003; Thennadil S N, Rennert J L, Wenzel B J, Hazen K H, Ruchti T L, Block M B, "Comparison of glucose concentration in interstitial fluid, and capillary and venous blood during rapid changes in blood glucose levels", $Diab.\ Tech.\ Ther.,$ 3(3):357-65, 2001).

The performance of the arm and abdominal sensors was comparable with equivalent Clarke error grid statistics and mean absolute relative difference. The precision of the matched Freestyle Navigator® sensors worn on the arm and abdominal had a coefficient of variation of 10% (n=312, 953).

There was no difference in performance of the sensor as a function of age, gender or ethnicity. However, there were small but measurable differences in the accuracy of the sensor depending on the subject's BMI and also on the years since diagnosis. Subjects with BMI less than 25.0 had 78.8% in the Clarke error grid A zone (N=4844), whereas subjects with BMI between 25.0 and 30.0 had 82.2% in the Clarke error grid A zone (N=7855) and subjects with BMI greater than 30.0 had 84.4% in the Clarke error grid A zone (N=3928). Similarly, there were small but measurable differences in accuracy depending on the years since diagnosis of type 1 diabetes. The highest accuracy, 88.5% in the Clarke error grid A zone, was found in subjects who had been diagnosed with diabetes for five years or less (N=2066) and 81.3% for subjects diagnosed between 5 and 25 years (N=9133). Subjects diagnosed with type 1 diabetes for over 25 years had 79.9% in the Clarke error grid A zone (N=5448).

Clinical Accuracy Under Special Circumstances

The evaluation of the overall accuracy and performance of the FreeStyle Navigator® continuous glucose monitor included periods of deliberately-induced rapidly rising and rapidly falling blood glucose, i.e. in response to the glucose and insulin challenges. There were significant differences in the accuracy compared with the laboratory reference measurements depending on the different rates of change of the underlying blood glucose. Table (3) gives the Clarke error grid statistics and the median absolute relative difference percentage as a function of the rate of change of blood glucose as determined by the YSI measurements. The effect of the physiological lag on the accuracy of the sensor values compared to venous reference samples is more pronounced at the high rates of change, particularly during when the absolute rate of change exceeds 2 mg/dL/min.

TABLE (3)

Rate of change and Clarke error grid statistics and median ARD

| Rate of Change (mg/dL/min) | N | Clarke Error Grid Region | | | | | Median ARD % |
|---|---|---|---|---|---|---|---|
| | | A | B | C | D | E | |
| <−2 | 601 | 54.6 | 42.3 | 1.3 | 1.8 | 0.0 | 17.4 |
| −2 to −1 | 1728 | 71.7 | 26.2 | 0.3 | 1.8 | 0.0 | 11.8 |
| −1 to 1 | 14653 | 84.9 | 13.5 | 0.0 | 1.5 | 0.0 | 8.5 |
| 1 to 2 | 1954 | 79.8 | 18.9 | 0.0 | 1.3 | 0.0 | 11.0 |
| >2 | 691 | 63.5 | 34.7 | 0.0 | 1.7 | 0.0 | 16.9 |

Figure 5:
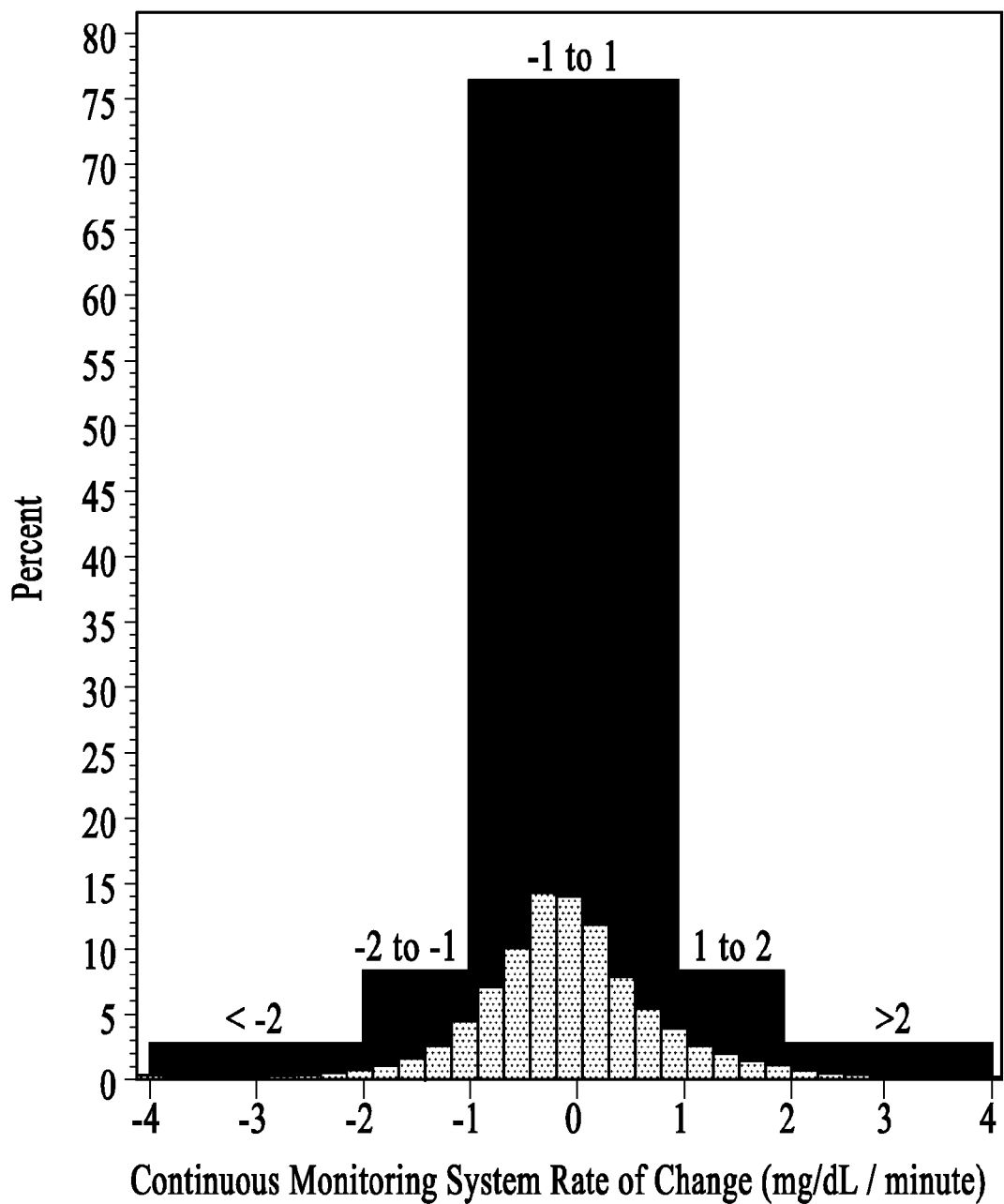
FIG. 5 shows rate of change histogram showing underlying rate of change at high resolution (in units of 0.25 mg/dL/min) and in units of the continuous monitoring system of FIG. 1 receiver trend arrows (1.0 mg/dL/min)

FIG. 5 illustrates the rate of change histogram showing underlying rate of change at high resolution (in units of 0.25 mg/dL/min) and in units of the Navigator receiver trend arrows (1.0 mg/dL/min). The rate of change of glucose as measured by the sensor was between −1 and +1 mg/dL/min 74.6% of the time. Referring to FIG. 5, there is a slight difference in the measured occurrence of absolute rates of change less than 1 mg/dL/min due to the different sampling frequency and temporal extent of the Freestyle Navigator® system and YSI measurements.

The Freestyle Navigator® trend arrows would have been in the horizontal position indicating an absolute rate of change less than 1 mg/dL/min 74.1% of the time for which the YSI data revealed 71.9% of all readings in this range. Both values are consistent with previously reported results (see for example: Dunn T C, Eastman R C, Tamada J A, "Rates of glucose change measured by blood glucose meter and the GlucoWatch Biographer during day, night, and around mealtimes", Diabetes Care 27: 2161-2165, 2004; Kovatchev, B. P., Clarke, W. L., Breton, M., Brayman, K. and McCall, A.

"Quantifying Temporal Glucose Variability in Diabetes via Continuous Glucose Monitoring: Mathematical Methods and Clinical Application" *Diab. Technol. Thera.*, 7, 849-862, 2005).

Figure 6:
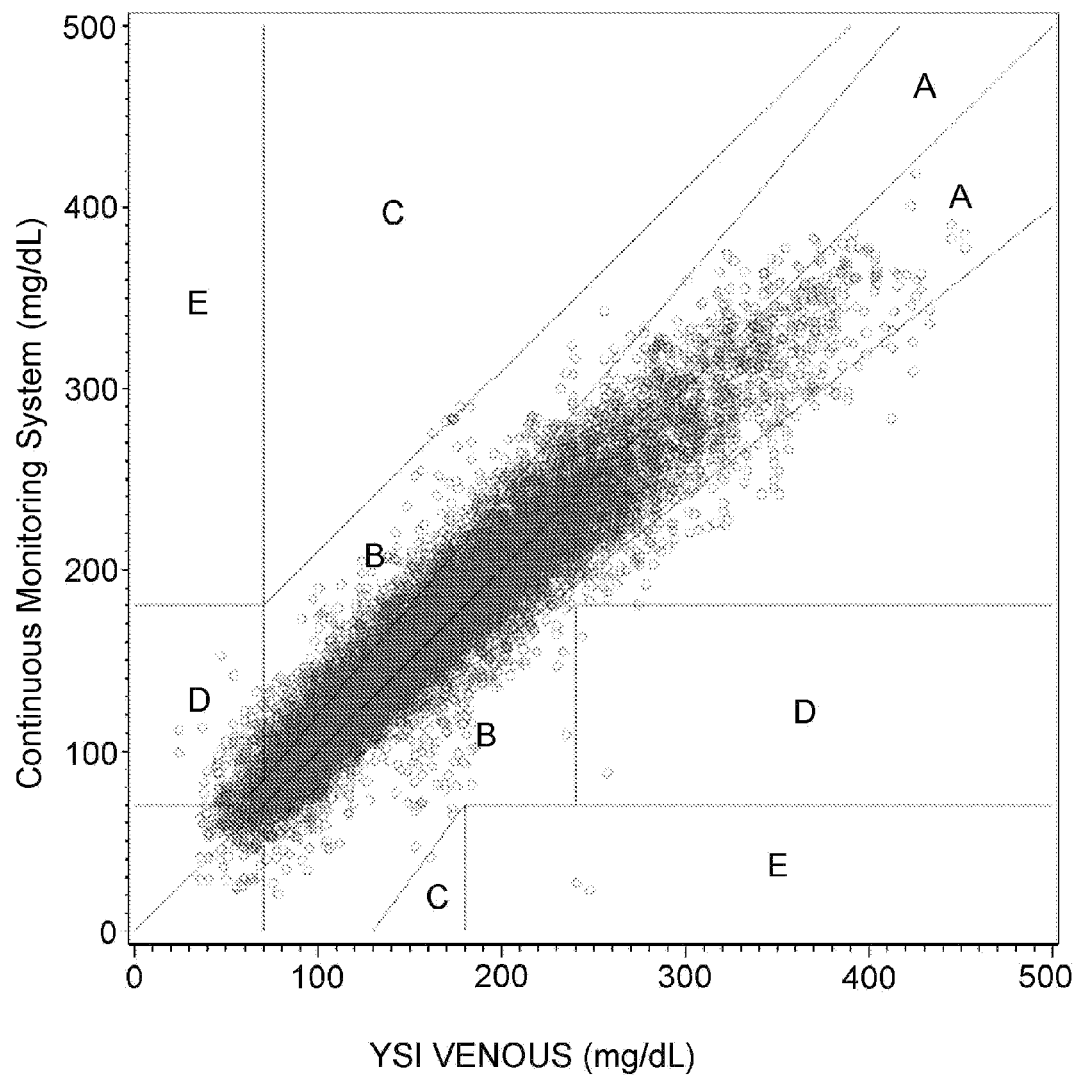
FIG. 6 shows a Clarke error grid for YSI rates of change between −1 to 1 mg/dL/min.

FIG. 6 illustrates Clarke error grid for YSI rates of change between −1 to 1 mg/dL/min showing increase in accuracy during modest rates of change. Referring to FIG. 6, whereas the overall percentage of paired points in the Clarke error grid A zone was 81.7%, the percentage in the A zone for rates of change between −1 mg/dL/min and +1 mg/dL/min was significantly higher at 84.9%. Similarly, the mean and median absolute relative differences at these times were 11.4% and 8.5% respectively.

The accuracy of the Freestyle Navigator® continuous glucose monitor was evaluated in comparison to a standard laboratory reference method using venous blood samples. The overall mean and median absolute relative difference of the sensor in the current study of 12.8% and 9.3% represent a significantly higher level of accuracy than previously published results from other continuous glucose monitoring systems (see for example, Diabetes Research in Children Network (DirecNet) Study Group: "The Accuracy of the CGMS in Children with Type 1 Diabetes: Results of the Diabetes Research in Children Network (DirecNet) Accuracy Study". *Diabetes Technol Ther* 5(5):781-789, 2003; Diabetes Research in Children Network (DirecNet) Study Group: "The Accuracy of the GlucoWatch G2 Biographer in Children with Type 1 Diabetes: Results of the Diabetes Research in Children Network (DirecNet) Accuracy Study". *Diabetes Technol Ther* 5(5):791-800, 2003; Tansey M J, Beck R W, Buckingham B A, Mauras N, Fiallo-Scharer R, Xing D, Kollman C, Tamborlane W V, Ruedy K J, "Accuracy of the modified Continuous Glucose Monitoring System (CGMS) sensor in an outpatient setting: results from a diabetes research in children network (DirecNet) study." *Diab. Tech. Ther.* 7(1):109-14, 2005; Garg S., Zisser H., Schwartz S., Bailey T., Kaplan R., Ellis S. and Jovanovic L, "Improvement in glycemic excursions with a transcutaneous, real-time continuous glucose sensor", *Diabetes Care*, 29, 44-50, 2006).

The high accuracy of the system as measured by the percentage in the Clarke error grid A zone and the mean and median absolute relative differences remained high over the entire five days. There was a small, but measurable improvement in the Clarke error grid statistics and the absolute relative difference values on the fourth day. This is due principally to the fact that there were no glucose challenges administered on the fourth day of the study resulting in fewer rates of change on that day less than 2 mg/dL/min than on other days. In addition, there may be a small increase in accuracy on the fourth day associated with the final system calibration at 72 hours after sensor insertion. Similarly, the slight decrease in accuracy observed on the third and fifth days of the sensor wear may be associated with the fact that these days had a greater number of glucose and insulin challenges than other days in the study, resulting in more absolute rates of change on those days in excess of 2 mg/dL/min.

A significant portion of the apparent discrepant points between the Freestyle Navigator® and the venous reference samples are likely due to the physiological lag alone. An example of the effect of physiological lag on accuracy is the point at the nadir of the curves in FIG. 4B, which is categorized in the Clarke error grid analysis as a clinically unacceptable D zone point. In this case, although the point-wise comparison of the Freestyle Navigator® sensor value and the venous reference sample value suggests a failure to detect a hypoglycemic event, it is clear from the data that the Freestyle Navigator® system is correctly tracking the fall of the subject's glucose level.

In the case shown in FIG. 4B, with the projected alarm capability enabled and the detection threshold set at 70 mg/dL, the device would have alerted the user to a predicted change in clinical state from euglycemia to hypoglycemia when the Freestyle Navigator® glucose value was approximately 175 mg/dL and the measured rate of glucose decrease was in excess of −3.5 mg/dL/min. At that moment, the trend arrow was in the downward vertical direction, indicating a rate of glucose decrease of greater than 2 mg/dL/min, and the device's alarm would have used predictive algorithm to identify that the subject would be hypoglycemic in thirty minutes.

At the time when the projected alarm would have alerted the subject to an impending hypoglycemic event, the YSI reading was approximately 90 mg/dL. An interpolation of the YSI data indicates that the subject's blood sugar crossed the 70 mg/dL threshold for hypoglycemia approximately twenty-six minutes later. Although the paired YSI and Freestyle Navigator® system points at the nadir of the curve result in a D zone point on the Clarke error grid, it is clear from a detailed analysis that the projected alarm would have alerted the subject to an impending hypoglycemic event in a timely manner.

Another important measure of the clinical accuracy, and ultimately the clinical utility, of the Freestyle Navigator®system is the percentage of points in the clinically-accurate Clarke error grid A zone. A recent numerical simulation study evaluated the effect of sensor inaccuracy on the statistics associated with glucose monitoring error grid analysis using data from a clinical trial of a continuous glucose monitoring system in type 1 children and adolescents (Kollman et al., 2005). In the numerical study, paired points from the actual continuous glucose monitoring system and a laboratory reference method were randomly "shuffled" to simulate a high degree of sensor inaccuracy. The study found that 78% of the randomly shuffled paired points were still in the combined A and B zones of the Clarke error grid. A more useful measure of the clinical accuracy and utility of new glucose monitoring technology may be the percentage of points in the clinically-accurate Clarke error grid A zone alone. (Kollman C, Wilson D M, Wysocki T, Tamborlane W V, Beck R W, "Limitations of the Statistical measures of Error in Assessing the Accuracy of continuous Glucose Sensors", *Diab. Tech. Ther.*, 7(5):665-672, 2005). An alternative to the more commonly-used metric of combined A and B zone percentage is to rely instead on the total percentage in the A zone alone. The results of the present study showing the Freestyle Navigator® system achieving 81.7% in the A zone alone represent a new level of performance for continuous glucose monitoring systems.

The high accuracy and performance of the Freestyle Navigator® system at night is also in contrast with previous reports of continuous glucose monitoring systems that exhibited sustained periods of anomalous nocturnal hypoglycemia (see for example: McGowan K. Thomas W, Moran A. "Spurious reporting of nocturnal hypoglycemia by CGMS in patients with tightly controlled type I diabetes" Diabetes Care 2002; 25: 1499-1503; Metzger My Leibowitz G, Wainstein J, Glaser B, Raz I. "Reproducibility of glucose measurements using the glucose sensor" *Diabetes Care* 2002; 25: 1185-1191; Mauras N, Beck R W, Ruedy K J, Koliman C, Tamborlane W V, Chase H P "Lack of accuracy of continuous glucose sensors in hialthy nondiabetic children: results of the Diabetes Research in Children Network (DirecNet) accuracy study" *J Pediatr* 2004; 144:770-775).

The difference in accuracy as a function of BMI may be related to the length of the Freestyle Navigator® sensor and the thickness of the subcutaneous adipose tissue layer in subjects with BMI less than 25. Anthropometric data strongly suggests that the insertion of the Freestyle Navigator® sensor in the upper arm or abdomen will result in the sensor being placed as intended in the subcutaneous adipose tissue layer in most individuals (Horejsi, R., Moller, R., Pieber, T R, Wallner, S., Sudi, K, Reibnegger, G. and Tafeit "Differences of subcutaneous adipose tissue topography between type 2 diabetic men and healthy controls" *Exp. Biol. Med.*, 227, 794-798, 2002). However, in some individuals with low BMI, the data indicate that the subcutaneous adipose tissue layer thickness on the posterior arm upper arm or even the lower abdominal quadrant may be only slightly greater than the required 6 mm thickness needed to properly accommodate the sensor. Although the overall sensor performance in subjects with BMI less than 25 is still excellent (78.8% in the clinically-accurate Clarke error grid A zone), there is a small but measurable difference when compared with subjects with BMI greater than 30 (84.4% in the clinically-accurate Clarke error grid A zone). In the low BMI subjects with reduced subcutaneous adipose tissue layer thickness, the proximity of skeletal muscle tissue to the sensor in the adipose tissue could increase the effect reported by Moberg et al. in which tissue glucose nadirs were not only delayed relative to plasma, but also reduced especially during insulin-induced hypoglycemia (Moberg E, Hagstrom-Toft E, Amer P. and Bolinder J. "Protracted glucose fall in subcutaneous adipose tissue and skeletal muscle compared with blood during insulin-induced hypoglycaemia" *Diabetologia* 40, 1320-1326, 1997).

In the present study, the apparent difference in accuracy as a function of years since diagnosis is most likely also a result of the weak dependence of accuracy on BMI. The 6 subjects with a diagnosis of diabetes less than five years, for whom there was the highest percentage in the Clarke error grid A zone and the lowest median absolute relative difference, also by chance had the highest mean BMI (29.8). Similarly, the 18 subjects with lowest BMI (<24.9) in the study happened to also have the highest mean years since diagnosis of diabetes (30.1 years).

Insulin Adjustment Procedure—Clinical Decision Analyses

Insulin Adjustment Analysis

The Insulin Adjustment Analysis evaluates the difference between insulin dosing based on Freestyle Navigator® Continuous Glucose Monitoring System (CM) readings and that based on reference readings. The interpretation of the analysis is best understood considering a hypothetical patient with a glucose target level of 90-120 mg/dL and an insulin sensitivity of 30 mg/dL/unit. The glucose target level represents aggressive therapy where the therapeutic goal is to keep glucose squarely in the normal range. The analysis is targeted to meet the requirements of intensive insulin therapy. The choice of insulin sensitivity was made to simplify interpretation—the treatment differences between Navigator CM and YSI are calculated in whole number differences in the units of insulin. This seemingly arbitrary choice of the hypothetical patient has no influence on the results of the Insulin Adjustment Analysis—the choice was based on the goals of intensive insulin therapy and the ease of interpretation of the results.

The Insulin Adjustment Analysis data is reported as differences in units of insulin. (see Table 4). This is an intermediate result that allows a more detailed characterization of the data than the final summary (see Table 5). Decisions with Navigator CM were rated Correct 89.3% (1180/1322) of the time and Acceptable 7.6% (100/1322) of the time. Since the Acceptable rating translates to a glucose adjustment to within the normal glucose range, accurate adjustments are the sum of Correct and Acceptable categories, 96.8% (1280/1322).

TABLE 4

Treatment Difference for the Hypothetical Patient with Insulin Sensitivity = 30 mg/dL/unit and Glucose Target = 90-120 mg/dL

| Navigator CM-YSI Treatment Difference (Units of insulin) | Glucose <200 mg/dL | | | Glucose ≥200 mg/dL | | |
|---|---|---|---|---|---|---|
| | N | % | Category | N | % | Category |
| −4 | 0 | 0 | Hyperglycemia 2 | 4 | 0.6 | Hyperglycemia 2 |
| −3 | 1 | 0.1 | Hyperglycemia 1 | 13 | 2.0 | Hyperglycemia 1 |
| −2 | 11 | 1.6 | Acceptable | 78 | 12.1 | Acceptable |
| −1 | 120 | 17.7 | Correct | 215 | 33.4 | Correct |
| 0 | 353 | 52.0 | Correct | 240 | 37.3 | Correct |
| 1 | 173 | 25.5 | Correct | 79 | 12.3 | Correct |
| 2 | 18 | 2.7 | Possible Error | 11 | 1.7 | Acceptable |
| 3 | 2 | 0.3 | Error | 3 | 0.5 | Possible Error |
| 4 | 1 | 0.1 | Error | 0 | 0 | Error |
| Total | 679 | 100 | | 643 | 100 | |

TABLE 5

Insulin Adjustment Analysis Summary

| Category | Effect on Blood Glucose | N | % |
|---|---|---|---|
| Correct | Within ±30 mg/dL of target glucose | 1180 | 89.3 |
| Acceptable | Within normal glucose range | 100 | 7.6 |
| Possible Error (hypo) | 60 mg/dL below target glucose | 21 | 1.6 |
| Error (hypo) | ≥90 mg/dl below target glucose | 3 | 0.2 |
| Hyperglycemia 1 | 90 mg/dL above target glucose | 14 | 1.1 |
| Hyperglycemia 2 | ≥120 mg/dl above target glucose | 4 | 0.3 |
| Total | | 1322 | 100 |

In summary, this analysis describes 3 occurrences of "Error (hypo)" and 4 occurrences of "hyperglycemia 2" being potentially indicated from 1322 decision points analyzed.

Glucose Peak

Continuous glucose monitoring provides the ability to identify and quantify the maximum glucose excursions after meals and during the night. The quantification of glucose peaks was clinically accurate 88.1% of the time and clinically useful 97.6% of the time (see Table 6).

TABLE 6

Glucose Peak Analysis

| Difference | Clinical Assessment | N | % |
|---|---|---|---|
| ±15 mg/dL | Accurate | 263 | 41.5 |
| ±45 mg/dL | Accurate | 295 | 46.6 |
| ±75 mg/dL | Useful | 60 | 9.5 |
| ±105 mg/dL | Misclassification | 14 | 2.2 |
| ±135 mg/dL | Misclassification | 1 | 0.2 |
| Total | | 633 | 100.0 |

Insulin Adjustment Analysis

The Insulin Adjustment Analysis evaluates the hypothetical difference between insulin dosing based on Navigator CM readings to that based on a blood glucose meter such as Freestyle Blood Glucose (BG) readings. The interpretation of the analysis is best understood considering a hypothetical patient with a glucose target level of 90-120 mg/dL and an insulin sensitivity of 30 mg/dL/unit. The glucose target level represents aggressive therapy where the therapeutic goal is to keep glucose squarely in the normal range. The analysis is targeted to meet the requirements of intensive insulin therapy. The choice of insulin sensitivity was made to simplify interpretation—the treatment differences between Navigator CM and Freestyle BG YSI (see Table 7) are calculated in whole number differences in the units of insulin. This seemingly arbitrary choice of the hypothetical patient has no influence on the results of the Insulin Adjustment Analysis—the choice was based the goals of intensive insulin therapy and the ease of interpretation of the results.

The Insulin Adjustment Analysis data is reported as differences in units of insulin (see Table 7). There were 6,040 paired (Navigator CM-Freestyle BG) glucose readings available at times of subject-reported insulin dosing or bedtime in the Home Use Study. The analysis is summarized in Table 8 with 86.5% (5226/6040) of the readings correct and 94.3% (5696/6040) accurate or acceptable. These results provide approximately 89.3% (1180/1322) correct and 96.8% (1280/1322) accurate or acceptable.

TABLE 7

Treatment Difference for the Hypothetical Patient with Insulin Sensitivity = 30 mg/dL/unit and Glucose Target = 90-120 mg/dL

| Difference in Insulin Dose (Units) | Glucose < 200 mg/dL | | Glucose ≥ 200 mg/dL | |
|---|---|---|---|---|
| | N | (%) | N | (%) |
| 4 | 0 | 0 | 1 | 0.0 |
| 3 | 11 | 0.3 | 2 | 0.1 |
| 2 | 84 | 2.1 | 14 | 0.7 |
| 1 | 810 | 20.1 | 162 | 8.1 |
| 0 | 2362 | 58.5 | 530 | 26.5 |
| −1 | 675 | 16.7 | 687 | 34.3 |
| −2 | 89 | 2.2 | 367 | 18.3 |
| −3 | 8 | 0.2 | 163 | 8.1 |
| −4 | 0 | 0 | 75 | 3.7 |
| Total | 4039 | — | 2001 | — |

TABLE 8

Insulin Adjustment Analysis Summary

| Category | Effect on Blood Glucose | N | % |
|---|---|---|---|
| Correct | Within ±30 mg/dL of target glucose | 5226 | 86.5 |
| Acceptable | Within normal glucose range | 470 | 7.8 |
| Possible Error (hypo) | 60 mg/dL below target glucose | 86 | 1.4 |
| Error (hypo) | ≧90 mg/dl below target glucose | 12 | 0.2 |
| Hyperglycemia 1 | 90 mg/dL above target glucose | 171 | 2.8 |
| Hyperglycemia 2 | ≧120 mg/dl above target glucose | 75 | 1.2 |
| Total | | 6040 | 100 |

Insulin dosing or bedtime was not indicated for 5,447 of the 11,487 Freestyle BG duplicate points. The Insulin Adjustment Analysis was also conducted using the 5,447 Freestyle BG duplicate points for which there was no indication of insulin injection to determine if there was a substantive difference between the two populations. The Insulin Adjustment Analysis data is reported as differences in units of insulin (See Table 9). The results are slightly better for the points where insulin injections were not indicated (See Table 10) with 89.4% (4868/5447) correct and 95.5 (5203/5447) correct or acceptable.

TABLE 9

Treatment Difference for the Hypothetical Patient with Insulin Sensitivity = 30 mg/dL/unit and Glucose Target = 90-120 mg/dL - Non-insulin Injection Points

| Difference in Insulin Dose (Units) | Glucose < 200 mg/dL | | Glucose ≥ 200 mg/dL | |
|---|---|---|---|---|
| | N | (%) | N | (%) |
| 4 | 2 | 0.0 | 0 | 0 |
| 3 | 11 | 0.3 | 1 | 0.1 |
| 2 | 95 | 2.3 | 26 | 2.0 |
| 1 | 876 | 21.2 | 132 | 10.0 |
| 0 | 2473 | 59.9 | 388 | 29.5 |
| −1 | 588 | 14.2 | 411 | 31.2 |
| −2 | 81 | 2.0 | 228 | 17.3 |
| −3 | 5 | 0.1 | 88 | 6.7 |
| −4 | 0 | 0 | 42 | 3.2 |
| Total | 4131 | — | 1316 | — |

TABLE 10

Insulin Adjustment Analysis Summary Non-insulin Injection Points

| Category | Effect on Blood Glucose | N | % |
|---|---|---|---|
| Correct | Within ±30 mg/dL of target glucose | 4868 | 89.4 |
| Acceptable | Within normal glucose range | 335 | 6.2 |
| Possible Error (hypo) | 60 mg/dL below target glucose | 96 | 1.8 |
| Error (hypo) | ≧90 mg/dl below target glucose | 13 | 0.2 |
| Hyperglycemia 1 | 90 mg/dL above target glucose | 93 | 1.7 |
| Hyperglycemia 2 | ≧120 mg/dl above target glucose | 42 | 0.8 |
| Total | | 5447 | 100 |

When a patient adjusts an insulin dose using a blood glucose meter such as Freestyle Blood Glucose monitor, there is no indication if glucose is changing. If glucose is rising at the time of glucose dosing, there is insufficient insulin to stabilize blood glucose and the predicted insulin dose will be too small. Likewise, if glucose is descending, there is already insulin in the blood, and the predicted insulin dose will be too large. The rate of glucose change indicated by Navigator CM at the time of insulin dosing (see Table 11) indicates glucose changes >±2 mg/dL/minute 4.0% of the time, and >±1 mg/dL/minute 18.3% of the time. The agreement of static the blood glucose meter readings with static reference readings is excellent, but the interpretation of this agreement to suggest accurate insulin dosing with the blood glucose meter is not correct. When insulin is dosed with no knowledge of changing glucose levels, the dosing will be incorrect a significant fraction of the time. The determination of 94.3% Navigator CM dosing accuracy in this study and 96.8% Navigator CM dosing accuracy in a previous study provide realistic estimations when the rate of glucose change is also known.

TABLE 11

Navigator CM Rate Indication at the Time of Insulin Dosing

| Navigator CM Rate of Change (mg/dL/minute) | N | (%) |
|---|---|---|
| >2.0 | 330 | 3.3 |
| 1.0 to 2.0 | 897 | 9.0 |
| −1.0 to 1.0 | 8140 | 81.7 |
| −2.0 to −1.0 | 526 | 5.3 |
| <−2.0 | 72 | 0.7 |

The description below details a further user study results from a highly accurate continuous glucose monitoring system such as, for example, Freestyle Navigator® system. Of the 137 subjects enrolled in the investigation, 123 completed the 40-day monitoring period. The other 14 subjects withdrew from the study due to non-compliance with protocol demands (n=8) or difficulties handling the device (n=6). None of the discontinued subjects participated in the unblinded portion of the study. The glucose data available for the discontinued subjects was included in the paired point analysis.

The performance of the Freestyle Navigator® was assessed using the absolute relative difference between the sensor interstitial glucose measurements and the blood glucose measurements. Data from 961 sensors with 11,487 paired FreeStyle BG reference values were evaluated. The mean absolute relative difference was 14.4% and the median absolute relative difference was 11.1%. The mean absolute relative difference indicates that, on average, the CM reading was 14.4% higher or lower than the corresponding BG reading. The median absolute relative difference indicates that the CM reading was equally as likely to be within 11.1% of the BG reading, either higher or lower, as it was to be outside of that range.

The equation for the Deming regression had a slope of 0.83, an intercept of 21.8 mg/dL and correlation coefficient of 0.92. These results demonstrate a strong correlation between CM and BG readings.

Figure 7:
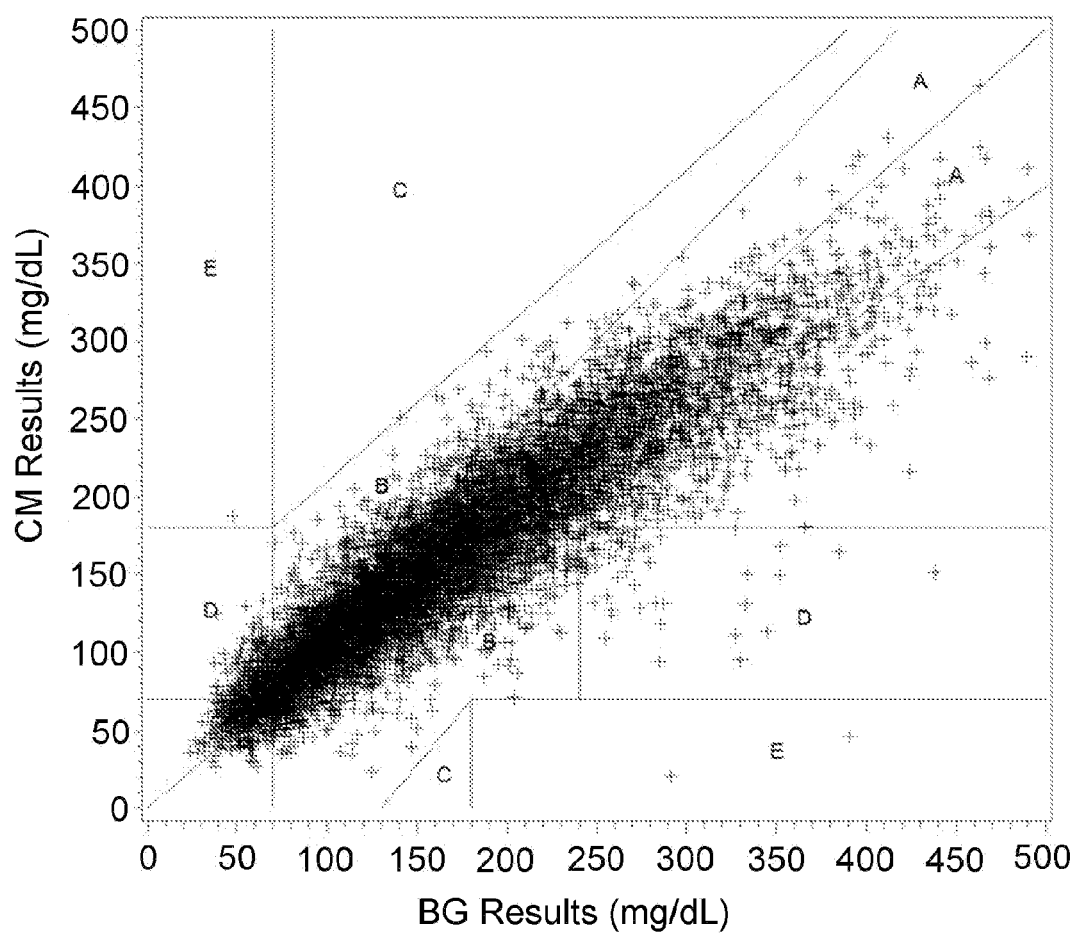
FIG. 7 shows the Clarke error grid from a high accurate continuous glucose monitoring system user study.

FIG. 7 shows the Clarke error grid for the study. There were a total of 11,487 paired points with averaged duplicate BG reference values and interpolated CM values, from 131 subjects. No paired points were available from six subjects. Of the 11,487 paired points, 77.2% fell in the Clarke error grid zone A, indicating a high level of correspondence between the reference blood glucose measurements and the CM results. There were 19.6% of the paired points in zone B and only 3.2% outside the A and B zones. Results for all the Clarke error grid zones are shown in Table 12 below. The results of the Consensus error grid are also included in Table 12.

TABLE 12

Summary statistics of Clarke and Consensus Error Grid

| | Clarke Error Grid | | Consensus Error Grid | |
|---|---|---|---|---|
| Zone | N | (%) | N | (%) |
| A | 8863 | 77.2 | 9180 | 79.9 |
| B | 2255 | 19.6 | 2194 | 19.1 |
| C | 1 | 0.0 | 109 | 0.9 |
| D | 365 | 3.2 | 4 | 0.0 |
| E | 3 | 0.0 | 0 | 0.0 |
| N paired points | 11487 | | 11487 | |

On the Clarke error grid, there were 365 individual points in the D zone. On the Consensus error grid, by contrast, the number of points in the D zone is reduced to four. In addition, the Consensus error grid shows 79.9% in the A zone, 99.0% in the A and B zones, less than 1% in the C and D zones and no points in the E zone.

A comparison of accuracy and performance by day of sensor wear shows that the system's performance on the fifth day is nearly equivalent to the performance on the first or second day. Table 13 contains data with the error grid statistics as well as the mean absolute relative difference from the study separated by day.

TABLE 13

Clarke Error Grid, absolute relative difference by day

| Zone | Day 1 N/(%) | Day 2 N/(%) | Day 3 N/(%) | Day 4 N/(%) | Day 5 N/(%) |
|---|---|---|---|---|---|
| Clarke A | 1061 (77.8) | 2182 (77.4) | 2110 (77.7) | 1884 (79.3) | 1626 (73.5) |
| Clarke B | 266 (19.5) | 551 (19.6) | 516 (19.0) | 427 (18.0) | 495 (22.4) |
| Clarke C | 0 (0.0) | 0 (0.0) | 0 (0.0) | 0 (0.0) | 1 (0.0) |
| Clarke D | 36 (2.6) | 84 (3.0) | 91 (3.3) | 63 (2.7) | 91 (4.1) |
| Clarke E | 1 (0.1) | 1 (0.0) | 0 (0.0) | 1 (0.0) | 0 (0.0) |
| N paired points | 1364 | 2818 | 2717 | 2375 | 2213 |
| Consensus A | | | | | |
| Consensus B | | | | | |
| Consensus C | | | | | |
| Consensus D | | | | | |
| Consensus E | | | | | |
| N paired points | 1364 | 2818 | 2717 | 2375 | 2213 |

TABLE 13-continued

Clarke Error Grid, absolute relative difference by day

| Zone | Day 1 N/(%) | Day 2 N/(%) | Day 3 N/(%) | Day 4 N/(%) | Day 5 N/(%) |
|---|---|---|---|---|---|
| Mean ARD | 14.8 | 14.3 | 14.0 | 13.9 | 15.3 |
| Median ARD | | | | | |

Table 14 shows that the CM readings are optimal when blood glucose is relatively stable (i.e., when the rate is within +/−1 mg/dL/min). As expected the bias increases somewhat as the magnitude of the rate of glucose change increases. However, the displayed rate arrow provides the necessary information to properly interpret the glucose result in these situations. The mean bias for glucose <100 mg/dL and the mean percent bias for glucose ≧100 mg/dL become increasingly positive as the rate decreases from +2 mg/dL/minute to −2 mg/dL/minute. Lag in the interstitial readings versus capillary blood glucose readings is the explanation for this result. When glucose levels were rising, the CM values were low, on average, versus BG with the difference versus BG lower for rising glucose (>1 mg/dL/minute) than for stable glucose (±1 mg/dL/minute). When glucose levels were falling CM was high, on average, versus BG with the difference versus BG higher for falling glucose (<1 mg/dL/minute) than for stable glucose (±1 mg/dL/minute).

TABLE 14

Difference measures vs. glucose rate of change

| Navigator CM Rate of Change (mg/dL per minute) | Mean | Median | N |
|---|---|---|---|
| Difference (mg/dL) for glucose <100 mg/dL | | | |
| >2.0 | 3.7 | −1.2 | 3 |
| 1.0 to 2.0 | 4.7 | 5.5 | 33 |
| −1.0 to 1.0 | 7.6 | 7.1 | 2028 |
| −2.0 to −1.0 | 17.9 | 18.7 | 261 |
| <−2.0 | 26.5 | 24.4 | 50 |

TABLE 14-continued

Difference measures vs. glucose rate of change

| Navigator CM Rate of Change (mg/dL per minute) | Mean | Median | N |
|---|---|---|---|
| Absolute difference (mg/dL) for glucose <100 mg/dL | | | |
| >2.0 | 11.0 | 9.8 | 3 |
| 1.0 to 2.0 | 12.5 | 9.9 | 33 |
| −1.0 to 1.0 | 13.3 | 10.8 | 2028 |
| −2.0 to −1.0 | 21.5 | 19.4 | 261 |
| <−2.0 | 32.4 | 27.0 | 50 |
| Percent difference % for glucose ≧=100 mg/dL | | | |
| >2.0 | −13.7 | −14.3 | 152 |
| 1.0 to 2.0 | −10.9 | −10.7 | 581 |
| −1.0 to 1.0 | −3.5 | −3.7 | 7245 |
| −2.0 to −1.0 | 6.9 | 6.8 | 432 |
| <−2.0 | 7.5 | 9.1 | 69 |
| Absolute % difference % for glucose ≧=100 mg/dL | | | |
| >2.0 | 17.0 | 16.1 | 152 |
| 1.0 to 2.0 | 14.8 | 12.6 | 581 |
| −1.0 to 1.0 | 12.2 | 9.8 | 7274 |
| −2.0 to −1.0 | 15.9 | 12.6 | 432 |
| <−2.0 | 18.3 | 14.5 | 69 |

The Clarke EGA as a function of Navigator rate (Table 15) exhibits the expected behavior. When glucose is descending by at least −2 mg/dL/min, there is a higher likelihood that a reading would fall into the left Zone D than when the glucose is stable or rising. When glucose is rising, there is a higher likelihood that a reading would fall into the right Zone D. The rate arrow provides the valuable information to properly interpret the glucose result (i.e. when glucose is rapidly descending Navigator CM tends to be higher than Navigator BG and when glucose is rapidly ascending Navigator CM tends to be lower than Navigator BG).

TABLE 15

Clarke EGA vs. glucose rate of change

| Zone | <−2.0 | % | −2.0 to −1.0 | % | −1.0 to 1.0 | % | 1.0 to 2.0 | % | >2.0 | % |
|---|---|---|---|---|---|---|---|---|---|---|
| A | 61 | 51.3 | 425 | 61.3 | 7372 | 79.3 | 455 | 74.1 | 101 | 65.2 |
| B | 45 | 37.8 | 194 | 28.0 | 1688 | 18.1 | 149 | 24.3 | 48 | 31.0 |
| C | 0 | 0.0 | 1 | 0.1 | 0 | 0.0 | 0 | 0.0 | 0 | 0.0 |
| D | 12 | 10.1 | 73 | 10.5 | 240 | 2.6 | 10 | 1.6 | 6 | 3.9 |
| E | 1 | 0.8 | 0 | 0.0 | 2 | 0.0 | 0 | 0.0 | 0 | 0.0 |
| Total | 119 | | 692 | | 9302 | | 614 | | 155 | |

Sensor Success Measures

The rate of successful sensor insertions was evaluated from reported results of each sensor insertion attempt, as well as the electronic records stored by the Receiver. The electronic records were used to determine whether each sensor was detected by the Receiver, and whether the user followed the steps in the labeling. The percentage of insertions that were successful, when used as directed, was similar for the blinded (96.0%) and unblinded (96.8%) phases of the study (96.4% overall). The percentage of successful insertions was similar for the arm (95.7%) and abdomen (97.4%) insertion sites. Abdomen insertions may have been more successful because it is easier to see the entire insertion process at the abdomen site when inserting a sensor on oneself.

The success rate for the initial Sensor Calibration process was evaluated from results recorded in the receiver log data for each successful sensor insertion attempt. The time required to complete the first sensor calibration was evaluated in addition to the overall success or failure. The percentage of sensors that were successfully calibrated and produced glucose results within the first 12 hours was calculated. Sensor calibration is not allowed within the first 10 hours. Sensors that could not be calibrated because conditions were out of range were excluded, e.g., if the glucose was changing too rapidly for calibration. The percentage of sensors that were successfully calibrated within 12 hours, when used as directed, was similar for the blinded (90.5%) and unblinded (92.6%) phases of the study (91.5% overall).

Sensor duration was evaluated as the time duration from sensor insertion to the last CM glucose result reported for the sensor. Some sensors were removed early by user error or discretion, or because of protocol logistics such as the end of the trial. These sensors are excluded from analysis, unless the sensor reached the nominal 5-day sensor life (>108 hours). The median sensor life was similar for the blinded (119.9 hours) and unblinded (120.0 hours) phases of the study. The percentage of sensors, used as directed, that produced glucose results for 108 hours or more was similar for the blinded (83.5%) and unblinded (83.0%) phases of the study. Sensors on the arm tended to have slightly longer duration (86.2% for >108 hours) than those on the abdomen (79.4%), because there is somewhat less flexing and folding of the skin at the posterior arm insertion site than on the abdomen, improving the effectiveness of the skin adhesive that holds the sensor in place.

Glycemic Analysis

The change in glycemic status between the blinded and unblinded phases of the study was stratified by type 1 and type 2 diabetes. During the unblinded phase when alarms were set, subjects were instructed to perform a BG test when alarms were triggered. Some important differences in controlling glucose concentration with insulin administration between the two types of diabetes are the following:

Subjects with type 2 diabetes are less likely to induce hypoglycemia with insulin because they are insensitive to insulin. Type 1 subjects, with normal insulin sensitivity are much more likely to induce hypoglycemia.

Subjects with type 2 diabetes can reduce hyperglycemia by reducing carbohydrate ingestion and allowing endogenous insulin to reduce blood glucose. Patients with type 1 diabetes produce no endogenous insulin, so a reduction of carbohydrates is not a viable strategy for controlling glucose. Controlling glucose with injected insulin is much more difficult than control with endogenous insulin.

Figure 8:
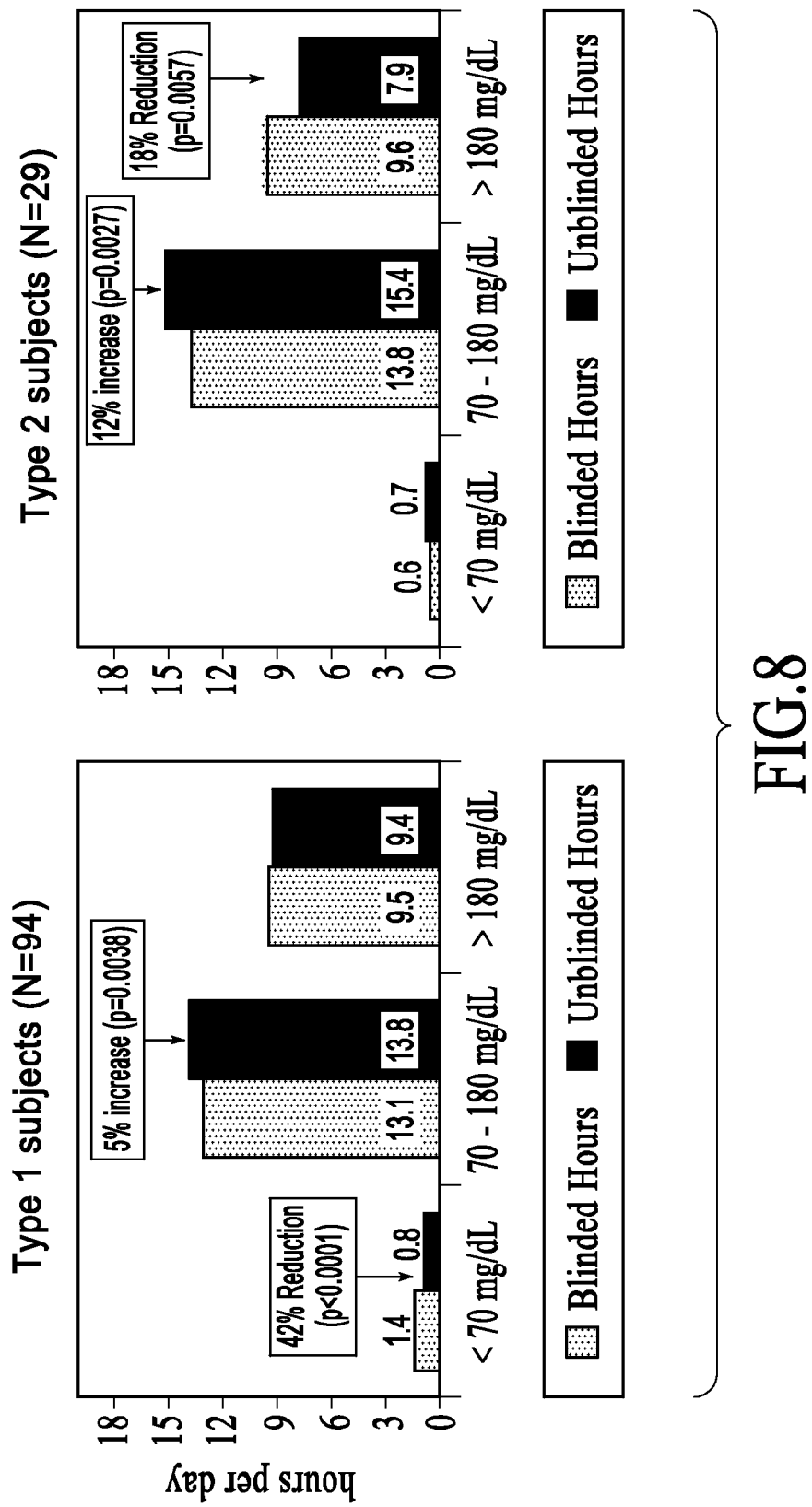
FIG. 8 illustrates the time spent in hypoglycemic, euglycemic, and hyperglycemic ranges for type 1 and 2 subjects in the blinded and unblinded phases of the study described in conjunction with FIG. 7.

The time spent in hypoglycemic (<70 mg/dL), euglycemic (70-180 mg/dL) and hyperglycemic ranges is illustrated in FIG. 8 for type 1 and 2 subjects in the blinded and unblinded phases of the study.

The type 1 subjects improved in the unblinded phase by reducing time in hypoglycemia. The time spent below the 70 mg/dL threshold for hypoglycemia was reduced by 42% from 1.4 hours to 0.8 hours (p<0.0001). The time spent in hyperglycemia (>180 mg/dL) did not change.

For type 2 subjects, the duration of hyperglycemia improved in the unblinded phase. The time spent in the euglycemic range increased by 12% (p=0.0027) and the time spent >180 mg/dL decreased by 18% (p=0.0057). As anticipated, the measures of hypoglycemia for type 2 subjects, which were low in the blinded phase, were largely unchanged in the unblinded phase.

Accordingly, a continuous analyte monitoring system in one embodiment includes an analyte sensor having at least about 80% of its paired data points within zone A and at least about 95% of its paired data points within zone A and zone B of the Clarke Error Grid, a transmitter capable of receiving information from the sensor, and a receiver capable of receiving information from the transmitter.

In one aspect, analyte sensor has at least about 85% of its paired data points within zone A of the Clarke Error Grid.

In a further aspect, the analyte sensor has at least about 90% of its paired data points within zone A of the Clarke Error Grid.

In still a further aspect, the analyte sensor has more than approximately 90% of its paired data points within zone A of the Clarke Error Grid.

Additionally, in another aspect, the analyte sensor has at least about 85% of its paired data points within zone A of the Consensus Error Grid, and further, where the analyte sensor has at least about 90% of its paired data points within zone A of the Continuous Glucose Error Grid Analysis.

The analyte sensor may be a glucose sensor.

In yet another aspect, the system may not require confirmation of analyte data obtained by the system.

The system may include a drug delivery device, where one or more of the transmitter and the receiver may be adapted to transmit analyte information to the drug delivery device.

In another aspect, the analyte sensor may be calibrated using single point calibration.

A continuous analyte monitoring system in accordance with another embodiment includes an analyte sensor having at least about 85% of its paired data points within zone A and at least about 95% of its paired data points within zone A and zone B of the Consensus Error Grid, a transmitter capable of receiving information from the sensor, and a receiver capable of receiving information from the transmitter.

The analyte sensor may have at least about 85% of its paired data points within zone A of the Consensus Error Grid.

The analyte sensor may have at least about 90% of its paired data points within zone A of the Consensus Error Grid.

The analyte sensor may have more than approximately 90% of its paired data points within zone A of the Consensus Error Grid.

In another aspect, the system may not require confirmation of analyte data obtained by the system.

The system may include a drug delivery device, where one or more of the transmitter and the receiver may be adapted to transmit analyte information to the drug delivery device.

Also, the analyte sensor may be calibrated using single point calibration.

A method of monitoring glucose levels in accordance with still another embodiment includes determining glucose concentration using a first transcutaneously positioned analyte sensor, reporting glucose concentration to a user, where a second sensor is not used to confirm the accuracy of the first transcutaneously positioned analyte sensor.

In one aspect, determining may include over a period of time ranging from about 1 day to about 7 days.

The first transcutaneously positioned analyte sensor may have at least about 85% of its paired data points within zone A of the Clarke Error Grid.

The first transcutaneously positioned analyte sensor may have at least about 90% of its paired data points within zone A of the Clarke Error Grid.

The first transcutaneously positioned analyte sensor may have more than about 90% of its paired data points within zone A of the Clarke Error Grid.

The first transcutaneously positioned analyte sensor may be a glucose sensor.

The method in a further aspect may include determining health related information based on the reported glucose concentration, where the health related information may include a bolus amount, or one or more of a food intake, medication dosage level, or activity level.

Also, the medication dosage level may include insulin dosage level.

In a further aspect, the method may include transmitting the reported glucose concentration, and where transmitting may include one or more of a wired transmission or a wireless transmission.

In still another aspect, the method may include calibrating the first transcutaneously positioned analyte sensor using single point calibration.

The first transcutaneously positioned analyte sensor may have at least about 95% of its paired data points within zone A and zone B of the Clarke Error Grid.

The first sensor may have at least about 85% of its paired data points within zone A.

A method of monitoring glucose levels in accordance with yet another embodiment includes determining glucose concentration using a first transcutaneously positioned analyte sensor, reporting glucose concentration to a user, where accuracy of the first transcutaneously positioned analyte sensor is established other than with a second sensor.

In one aspect, the first transcutaneously positioned analyte sensor has at least about 85% of its paired data points within zone A of the Clarke Error Grid.

In another aspect, the first transcutaneously positioned analyte sensor has at least about 90% of its paired data points within zone A of the Clarke Error Grid.

In still another aspect, the first transcutaneously positioned analyte sensor has more than about 90% of its paired data points within zone A of the Clarke Error Grid.

The first transcutaneously positioned analyte sensor may be a glucose sensor.

A method of monitoring glucose levels using a single glucose sensor in accordance with still yet a further embodiment includes transcutaneously positioning a glucose sensor in a patient for a period of time, determining glucose concentration of the patient using the transcutaneously positioned glucose sensor, and using one or more additional devices during the period of time only to calibrate the glucose sensor but not to confirm the accuracy of the transcutaneously positioned glucose sensor.

The glucose sensor in one embodiment has at least about 85% of its paired data points within zone A and at least about 95% of its paired data points within zone A and zone B of the Clarke Error Grid.

The glucose concentration may be determined over a period of time ranging from about 1 day to about 7 days.

In a further aspect, the glucose sensor has at least about 85% of its paired data points within zone A of the Clarke Error Grid.

In yet another aspect, the glucose sensor has at least about 90% of its paired data points within zone A of the Clarke Error Grid.

The glucose sensor in still another aspect has more than approximately 90% of its paired data points within zone A of the Clarke Error Grid.

In still a further aspect, the method may include determining a health related information based on the determined glucose concentration, where the health related information includes one or more of a food intake, medication dosage level, or activity level, and further, where medication dosage level includes insulin dosage level.

The method may include transmitting data associated with the determined glucose concentration, where transmitting may include one or more of a wired transmission or a wireless transmission.

Also, calibration of the glucose sensor may include performing single point calibration.

An analyte monitoring system in accordance with still yet another embodiment includes an analyte sensor configured to detect one or more analyte levels of a patient, a transmitter unit operatively coupled to the analyte sensor, the transmitter unit configured to transmit one or more signals associated with the detected one or more analyte levels, and a receiver unit configured to receive the transmitted one or more signals associated with the detected one or more analyte levels, where the accuracy of the detected one or more analyte levels relied upon to make a clinically relevant decision is established without using a blood glucose measurement.

In one aspect, the clinically relevant decision may include healthcare decision.

The clinically relevant decision may include a bolus amount determination.

The blood glucose measurement may include a confirmatory blood glucose measurement.

The detected one or more analyte level may be calibrated, for example, using single point calibration.

The transmitter unit may be configured to wirelessly transmit the one or more signals to the receiver unit.

The analyte sensor in one embodiment has at least about 85% of its paired data points within zone A and at least about 95% of its paired data points within zone A and zone B of the Clarke Error Grid.

An analyte monitoring device in accordance with still yet a further embodiment includes a receiver unit for receiving one or more signals related to an analyte level detected by an electrochemical sensor, the receiver unit including a display to display an indication of the analyte level, where the electrochemical sensor has at least about 85% of its paired data points within zone A and at least about 95% of its paired data points within zone A and zone B of the Clarke Error Grid.

The electrochemical sensor may have at least about 85% of its paired data points within zone A of the Clarke Error Grid.

The electrochemical sensor may have at least about 90% of its paired data points within zone A of the Clarke Error Grid.

The electrochemical sensor may have more than approximately 90% of its paired data points within zone A of the Consensus Error Grid.

The receiver unit may be configured to calibrate the one or more signals related to the analyte level, and further, where the receiver unit may be configured to display the calibrated one or more signals related to the analyte level without a confirmatory blood glucose measurement.

In another aspect, the receiver unit may be configured to calibrate the one or more signals related to the analyte level using single point calibration.

The receiver unit may be configured to display the one or more signals related to the analyte level without a confirmatory blood glucose measurement.

The receiver unit in one embodiment may include one of an rf receiver or an rf transceiver.

The receiver unit in still a further aspect may be configured to calibrate the one or more signals related to the analyte level using a calibration value of less that about one microliter of body fluid, where the body fluid includes blood.

The receiver unit may include an alarm configured to indicate when the analyte level is at or near a threshold level.

The threshold level may include one of hypoglycemia, impending hypoglycemia, hyperglycemia, or impending hyperglycemia.

The alarm may include one or more of an audible signal, a visual display, or a vibratory signal.

The alarm may be configured to automatically deactivate after a predetermined time period.

The receiver unit in one aspect may be a portable handheld unit.

The receiver unit may be configured for wearing on or under an article of clothing.

The receiver unit may include an rf transceiver configured to receive or transmit the one or more signals related to an analyte level.

In still another aspect, the display may be configured to display one or more of analyte level trend information, rate of change information associated with the analyte level, basal profile information, bolus amount information, or therapy related information.

In a further aspect, the receiver may include a blood glucose meter.

The display may be configured to display the indication of the analyte level at least one or more of once per minute, once per five minutes, once per ten minutes, or over a predetermined time period, where the predetermined time period may include one or more of less than 24 hour period, one day, three days, seven days, fourteen days, twenty one days, twenty eight days, less than thirty days, or greater than thirty days.

A monitoring device in a further embodiment includes a portable housing, an rf receiver coupled to the portable housing, the rf receiver configured to wirelessly receive one or more signals related to an analyte level of a patient detected by an electrochemical sensor, a processing unit coupled to the portable housing and to the rf receiver, the processing unit configured to process the one or more signal received by the rf receiver, and a display unit coupled to the portable housing and the processing unit, the display unit configured to display an indication associated with the one or more signals related to the analyte level of the patient, where the electrochemical sensor has at least about 85% of its paired data points within zone A and at least about 95% of its paired data points within zone A and zone B of the Consensus Error Grid.

The electrochemical sensor may have at least about 85% of its paired data points within zone A of the Consensus Error Grid.

The electrochemical sensor may have at least about 90% of its paired data points within zone A of the Consensus Error Grid.

An analyte monitoring device in accordance with still another embodiment includes a receiver unit for receiving one or more signals related to an analyte level detected by an electrochemical sensor, the receiver unit including a display to display an indication of the analyte level, and the receiver unit further configured to process one or more signals related to analyte related therapy for communication with a drug administration system, where the electrochemical sensor has at least about 85% of its paired data points within zone A and at least about 95% of its paired data points within zone A and zone B of the Clarke Error Grid.

In one aspect, the electrochemical sensor has at least about 90% of its paired data points within zone A of the Clarke Error Grid.

Various other modifications and alterations in the structure and method of operation of this disclosure will be apparent to those skilled in the art without departing from the scope and spirit of the present disclosure. Although the present disclosure has been described in connection with specific embodiments, it should be understood that the embodiments of the present disclosure as claimed should not be unduly limited to such specific embodiments. It is intended that the following claims define the scope of the present disclosure and that structures and methods within the scope of these claims and their equivalents be covered thereby.

What is claimed is:

1. An analyte monitoring device, comprising:
   a receiver unit for receiving one or more signals related to an analyte level detected by an electrochemical sensor, the receiver unit including a display to display an indication of the analyte level,
   wherein the electrochemical sensor includes a portion transcutaneously positioned under a skin surface and in fluid contact with an interstitial fluid to continuously monitor the analyte level over a predetermined time period and to detect the one or more signals related to the analyte level; and further
   wherein the receiver unit includes a signal processing algorithm to process the received one or more signals and to display the indication of the analyte level over the predetermined time period without confirming the accuracy level of the received one or more signals detected by the electrochemical sensor using an adjunctive measurement, wherein the received one or more signals from the electrochemical sensor has a Clarke Error Grid accuracy and a Consensus Error Grid accuracy of at least 80% within zone A and zone B.

2. The device of claim 1, wherein the accuracy level of the received one or more signals detected by the electrochemical sensor is determined to be clinically accurate based on the Clarke Error Grid.

3. The device of claim 1, wherein the accuracy level of the received one or more signals detected by the electrochemical sensor is determined to be clinically accurate based on the Consensus Error Grid.

4. The device of claim 1 wherein the receiver unit is configured to calibrate the one or more signals related to the analyte level.

5. The device of claim 4 wherein the receiver unit is configured to display the calibrated one or more signals related to the analyte level without a confirmatory blood glucose measurement.

6. The device of claim 1 wherein the receiver unit is configured to calibrate the one or more signals related to the analyte level using single point calibration.

7. The device of claim 1 wherein the receiver unit is configured to display the one or more signals related to the analyte level without a confirmatory blood glucose measurement.

8. The device of claim 1 wherein the receiver unit includes one of an rf receiver or an rf transceiver.

9. The device of claim 1 wherein the receiver unit is configured to calibrate the one or more signals related to the analyte level using a calibration value of less that about one microliter of body fluid.

10. The device of claim 9 wherein the body fluid includes blood.

11. The device of claim 1 wherein the receiver unit includes an alarm configured to indicate when the analyte level is at or near a threshold level.

12. The device of claim 11 wherein the threshold level includes one of hypoglycemia, impending hypoglycemia, hyperglycemia, or impending hyperglycemia.

13. The device of claim 11 wherein the alarm includes one or more of an audible signal, a visual display, or a vibratory signal.

14. The device of claim 11 wherein the alarm is configured to automatically deactivate after a predetermined time period.

15. The device of claim 1 wherein the receiver unit is a portable handheld unit.

16. The device of claim 15 wherein the receiver unit is configured for wearing on or under an article of clothing.

17. The device of claim 1 wherein the receiver unit includes an rf transceiver configured to receive or transmit the one or more signals related to an analyte level.

18. The device of claim 1 wherein the display is configured to display one or more of analyte level trend information, rate of change information associated with the analyte level, basal profile information, bolus amount information, or therapy related information.

19. The device of claim 1 including a blood glucose meter.

20. The device of claim 1 wherein the display is configured to display the indication of the analyte level at least one or more of once per minute, once per five minutes, once per ten minutes, or over a predetermined time period.

21. The device of claim 20 wherein the predetermined time period includes one or more of less than 24 hour period, one day, three days, seven days, fourteen days, twenty one days, twenty eight days, less than thirty days, or greater than thirty days.

22. An analyte monitoring device, comprising:
a receiver unit for receiving one or more signals related to an analyte level detected by an electrochemical sensor, the receiver unit including a display to display an indication of the analyte level, and the receiver unit further configured to process one or more signals related to analyte related therapy for communication with a drug administration system;
wherein the electrochemical sensor includes a portion transcutaneously positioned under a skin surface and in fluid contact with an interstitial fluid to continuously monitor the analyte level over a predetermined time period and to detect the one or more signals related to the analyte level; and further
wherein the receiver unit includes a signal processing algorithm to process the received one or more signals and to display the indication of the analyte level over the predetermined time period without confirming the accuracy level of the received one or more signals detected by the electrochemical sensor using an adjunctive measurement, wherein the received one or more signals from the electrochemical sensor has a Clarke Error Grid accuracy and a Consensus Error Grid accuracy of at least 80% within zone A and zone B.

23. The device of claim 22, wherein the accuracy level of the received one or more signals detected by the electrochemical sensor is determined to be clinically accurate based on the Clarke Error Grid.

* * * * *